(12) United States Patent  
Sher

(10) Patent No.: US 8,204,729 B2  
(45) Date of Patent: Jun. 19, 2012

(54) DEVICE FOR PREDICTING AND MANAGING BLOOD GLUCOSE BY ANALYZING THE EFFECT OF, AND CONTROLLING, PHARMACODYNAMIC INSULIN EQUIVALENTS

(76) Inventor: Philip Michael Sher, Plainsboro, NJ (US)

( * ) Notice: Subject to any disclaimer, the term of this patent is extended or adjusted under 35 U.S.C. 154(b) by 1126 days.

(21) Appl. No.: 12/063,665

(22) PCT Filed: Nov. 1, 2007

(86) PCT No.: PCT/US2007/083342  
§ 371 (c)(1),  
(2), (4) Date: Feb. 12, 2008

(87) PCT Pub. No.: WO2008/073609  
PCT Pub. Date: Jun. 19, 2008

(65) Prior Publication Data  
US 2010/0138197 A1 Jun. 3, 2010

Related U.S. Application Data

(60) Provisional application No. 60/855,878, filed on Nov. 1, 2006.

(51) Int. Cl.  
*G06G 7/58* (2006.01)

(52) U.S. Cl. .......................................................... 703/11

(58) Field of Classification Search ..................... 703/11  
See application file for complete search history.

(56) References Cited

U.S. PATENT DOCUMENTS

| 5,822,715 | A | 10/1998 | Worthington et al. |
| 6,835,175 | B1 | 12/2004 | Porumbescu |
| 6,925,393 | B1 | 8/2005 | Kalatz et al. |
| 2003/0028089 | A1 | 2/2003 | Galley |
| 2004/0193025 | A1 | 9/2004 | Steil |
| 2004/0220517 | A1 | 11/2004 | Starkweather |
| 2006/0031094 | A1 | 2/2006 | Cohen et al. |
| 2006/0137695 | A1 | 6/2006 | Hellwig |
| 2006/0173406 | A1 | 8/2006 | Hayes |

FOREIGN PATENT DOCUMENTS

| CA | 2555749 A1 | 9/2005 |
| EP | 1102194 A2 | 5/2001 |

OTHER PUBLICATIONS

International Search Report dated Sep. 1, 2009.

*Primary Examiner* — Hugh Jones  
(74) *Attorney, Agent, or Firm* — Altimatia, LLC; David M. Gange

(57) ABSTRACT

Embodiments of the invention are devices for assisting users in the management of blood glucose concentration levels in patients. Devices of the invention provide users with detailed information related to the pharmacodynamic behavior of insulin in a patient. By displaying and accepting information concerning time-dependent rates and amounts of pharmacodynamic insulin unit equivalents, the devices of the invention empower the user to make effective decisions regarding insulin dosing.

11 Claims, 1 Drawing Sheet

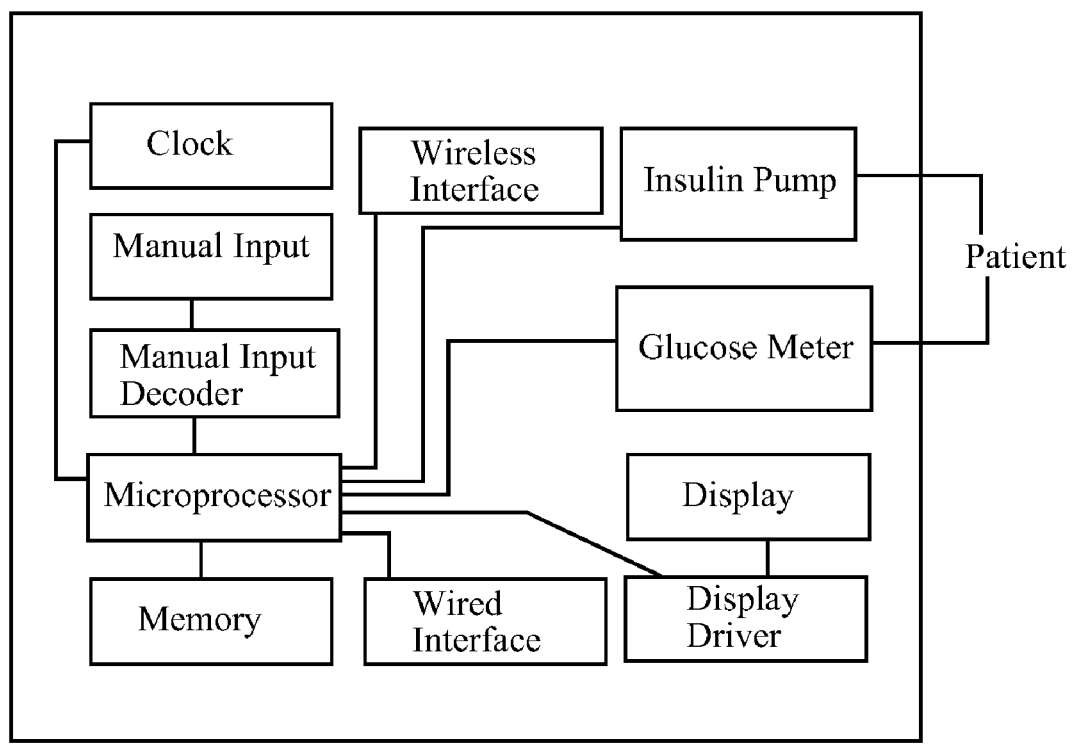

DEVICE FOR PREDICTING AND MANAGING BLOOD GLUCOSE BY ANALYZING THE EFFECT OF, AND CONTROLLING, PHARMACODYNAMIC INSULIN EQUIVALENTS

CROSS REFERENCE TO RELATED APPLICATIONS

This application claims the benefit of U.S. Provisional Patent Application Ser. No. 60/855,878, filed Nov. 1, 2006.

FIELD OF THE INVENTION

Embodiments of the invention relate to insulin delivery systems and methods for using insulin delivery systems, such as insulin pumps.

BACKGROUND OF THE INVENTION

For many people with diabetes, especially those with Type I diabetes, insulin pump therapy, also known as continuous subcutaneous insulin infusion, is preferable to injection therapy because greater flexibility and better blood glucose control are possible with an insulin pump. Insulin pumps offer their users the means to conveniently infuse insulin in an essentially continuous manner to satisfy basal insulin needs and also in various bolus modes to satisfy meal-related insulin needs and to correct hyperglycemia at any time.

Convenience is a considerable advantage that contributes to the superior flexibility and blood glucose control that insulin pump therapy enables. For example, insulin pump convenience manifests itself as an advantage when the user has incomplete knowledge of the content and timing of a meal before it begins. The barrier to dosing additional insulin with an insulin pump is lower than with injection therapy because all that is required to infuse more insulin is a few button presses. Shortly before the start of a poorly defined meal, an insulin pump user can infuse a minimum amount of insulin in time to prevent a rapid rise in blood glucose concentration (BGC), and then he can conveniently infuse more insulin if needed, and as needed as many times as he likes, as his understanding of the meal increases. This helps an insulin pump user, as compared with a patient on injection therapy, to enjoy greater flexibility and maintain better blood glucose control during and after meals about which he has incomplete knowledge at their beginning.

Another major advantage of insulin pump therapy over injection therapy derives from the fact that typically, only a rapid-acting type of insulin is infused with an insulin pump, whereas in injection therapy an intermediate or long-acting insulin is always included to satisfy basal insulin needs. Rapid-acting insulin action peaks only 1-2 hours after infusion and vanishes 3-5 hours after infusion, while intermediate and long-acting insulins provide insulin action that lasts much longer with peaks at least 4 hours after injection. Because in insulin pump therapy the timing and amount of insulin infusion are completely flexible and the insulin is rapid-acting, the timing and intensity of insulin action may be tailored more precisely to insulin need than with injection therapy. Precision in the timing and intensity of insulin action is advantageous, not only during and after meals, which in insulin pump therapy are managed by supplementing basal insulin infusion with insulin boluses, but also in conjunction with increased physical activity, which can require a decrease from the usual amount of basal insulin. With an insulin pump infusing a rapid-acting insulin, a well-timed suspension or decrease of basal insulin delivery can often prevent hypoglycemia due to increased physical activity. In contrast, with injection therapy, because an intermediate or long-acting insulin is included to satisfy basal insulin needs, consumption of carbohydrate is often the only recourse to prevent hypoglycemia.

A further advantage of insulin pump therapy is that it provides a means to preprogram precise and predictable changes in basal insulin hours in advance, such as an increase in the early morning hours to accommodate the greater insulin need caused by the "dawn phenomenon". With injection therapy, such changes are not as predictable and not as adjustable in amount. These and other differences between insulin pump therapy and injection therapy have made insulin pump therapy deservedly very popular.

The advantages of insulin pump therapy do not by themselves, however, guarantee good blood glucose control because figuring the timing and amount of insulin dosing necessary for good BGC control is very challenging for human beings, as well as for automated control systems which are now in experimental development. At present it remains the responsibility of the user to make all decisions about insulin dosing and food consumption to control BGC. Moreover, even when fully automated control systems become widely available, it is likely that some degree of user oversight, with the ability to intervene, will be desirable. Therefore, to most effectively manage BGC, it is important for a user to both develop the skill of estimating insulin need and also to acquire frequent feedback from a glucose monitor so that he can compensate for errors in his estimation of insulin need. Such errors occur because the amount of insulin needed is a function of variables that typically are not precisely known, including insulin sensitivity, food quantity and composition, physical activity level, the amount of insulin already in the subcutaneous tissue and blood, and the blood concentrations of other hormones. Moreover, even if all of these variables were known precisely, good algorithms for calculating the amount of insulin needed are not available. The commonly employed insulin-to-carbohydrate ratio concept, in which the amount of insulin needed for a meal is proportional to the amount of carbohydrate eaten, provides only a rough first approximation of the amount of insulin required; the major reason for this is that it only considers the carbohydrate content of food, but other nutrients affect BGC as well. Even a highly skilled insulin pump user may err significantly in his first estimation of insulin needed for a meal because it is not uncommon for a person with Type I diabetes to require meal-related insulin in an amount ten or more times the amount that would shift his BGC from above to below the normal range. Consequently, a mere 5-10% discrepancy between the amount of insulin needed for a meal and the amount of insulin infused for that meal can result in hypo- or hyperglycemia by the time the meal and the insulin have finished exerting their effects on BGC. Moreover, even if the amount of insulin dosed for a meal is correct, transient hyper- or hypoglycemia can occur due to temporary imbalances between meal and insulin effects. These difficulties underscore the importance of acquiring frequent feedback from a glucose monitor. Fortunately, frequent feedback has become possible because improved, nearly painless, point-in-time (conventional) glucose monitors and truly practical continuous glucose monitors are now available. Today, an insulin pump user measures BGC at least six, and often many more times per day, with each measurement providing an opportunity to adjust BGC up or down. In many circumstances, BGC may be measured at intervals of two hours or less. This is particularly useful in the aftermath of infusions of large amounts of insulin, for instance after a large, unfamiliar meal because with such frequent BGC monitoring, an insulin pump user can make an early assessment of how well his insulin dosing matches the insulin need created by his meal.

However, despite the advantages afforded by insulin pump therapy and the availability of frequent BGC data, the consistent maintenance of BGC within the target range is nearly impossible, especially in the context of a flexible lifestyle. One reason for this is that the pharmacodynamic effect of even rapid-acting insulins, when dosed subcutaneously, is slower than the effect of many foods on BGC. As a result, even if an insulin pump user infuses insulin in advance of a meal, if he underestimates the amount of insulin needed at that time, BGC will rise above the target range, at least transiently. While continuous BGC data could allow a user to take corrective action as soon as rising BGC signals impending hyperglycemia, even continuous BGC data does not alert the user to impending hyperglycemia early enough to prevent it when the effect of a food on BGC is faster than the pharmacodynamic effect of the insulin infused.

The pharmacodynamic profile of rapid-acting insulins creates another difficulty when BGC is frequently monitored. Because even rapid-acting insulins do not finish exerting their effects for three to five hours after dosing, in order for an insulin pump user to make use of BGC data within three to five hours after an insulin bolus, he must understand how much insulin action is to be expected from insulin already dosed, and his plans must consider that anticipated insulin action in order to avoid hypoglycemia. To address this issue, several insulin pump manufacturers produce insulin pumps that include a feature that calculates and displays "insulin on board", abbreviated here as IOB, and also known as "bolus-on-board", "active insulin" or "unused bolus insulin". This feature warns a user when IOB from recent insulin boluses may still be exerting its effect and thus offers a means to predict BGC, although for reasons discussed below, such predictions using methods described in the art are not sufficiently accurate.

Because of the complexity and difficulty of predicting and managing BGC, there remains a need for new tools that assist patients in accomplishing these important tasks. This specification describes a new method and system for predicting and managing blood glucose concentration.

Description of the Related Art and Definition of Pharmacodynamic Insulin Unit Equivalents and Related Expressions The following references disclose art relevant to embodiments of the present invention: U.S. Pat. No. 6,925,393; U.S. Pat. No. 5,822,715; U.S. Pat. No. 6,379,301; US 2006/137695; U.S. Pat. No. 6,835,175; US 2005/021006; US 2005/245904; US 2005/022274; US 2005/030164; US 2005/049179; US 2003/028089; US 2004/193025; US 2004/220517; US 2006/173406; US 2004/152622; US 2005/065465; CA 2555749; US 2005/272640; B. W. Bequette, et al., Diabetes Technology & Therapeutics 2004, 6, 868-873; D. R. L. Worthington, Medical Informatics 1997, 22, 5-19; B. W. Bequette, et al., Diabetes Technology & Therapeutics 2005, 7, 28-47; G. M. Steil, et al., Diabetes Technology & Therapeutics 2005, 7, 94-108; T. M. Gross, et al., Diabetes Technology & Therapeutics 2003, 5, 365-369; H. A. Wolpert, J. Diabetes Sci. Technol., 2007, 1, 146-150; Smart Pumping: A Practical Approach to Mastering the Insulin Pump, Howard Wolpert, editor, American Diabetes Association, 2002; Pumping Insulin: Everything You Need For Success With An Insulin Pump, third edition by John Walsh and Ruth Roberts, Torrey Pines Press, San Diego, 2000; Animas IR 1250 User Guide at http://www.animascorp.com/products/pr_insulinpump_IR1250_UserGuide.shtml; Animas IR 1200 Insulin on Board (IOB), Clinical Tips PN 420-151-00 Rev. A; Minimed Paradigm 522 and 722 Insulin Pumps User Guide at http://www.minimed.com/pdf/x22_user_guide.pdf; Deltec Cosmo Insulin Pump User Manual at http://www.cozmore.com/fileUpload/manual_5291-51A.pdf. These references and other references cited within this application are hereby incorporated herein by reference.

In order to adequately describe the present invention, indicate how it differs from the art, and explain its advantages over the art, it is helpful to discuss insulin pharmacodynamics and IOB in greater detail. Unfortunately, IOB has been described inconsistently and misleadingly. IOB has been variously described as the amount of insulin remaining in the body from previous boluses, the amount of insulin still active in the body from previous boluses, and the amount of insulin that has already been delivered to the body, but which has not yet been used. These descriptions differ from one another, and none of them provides a rigorous definition. The way IOB is understood by a skilled insulin pump user is as an insulin credit for the subsequent effect of bolus insulin infused recently enough to have not yet exerted its full effect. Note that its effect is the key to defining and quantifying IOB insulin. Likewise, the present invention focuses on insulin from the standpoint of its effect.

Researchers have developed a gold standard method to measure the effect of insulin—the euglycemic glucose clamp method (L. Heinemann, et al., Diabetes Technology & Therapeutics 2004, 6, 698-718; M. K. Frohnauer, et al., Diabetes Technology & Therapeutics 2001, 3, 419-429; A. D. Frick, et al., Diabetes, 2003, 52, suppl. 1, 511-P; L. Nosek, et al., Diabetes, 2003, 52, suppl. 1, 551-P; T. Heise, et al., Diabetes, 2005, 54, suppl. 1, 588-P; R. H. A. Becker, et al., Diabetes, 2005, 54, suppl. 1, 1367-P; R. N. Bergman, et al., Am. J. Physiol. 1979, 236, E667-E677; K. L. Swan, et al., Diabetes, 2007, 56, suppl. 1, 293-OR; O. Osterberg, et al., J. Pharmacokinetics and Pharmacodynamics, 2003, 30, 221-235; C. Homko, at al., Diabetes Care, 2003, 26, 2027-2031). There have been several publications of euglycemic glucose clamp studies that measure the effects of subcutaneously bolused rapid-acting types of insulin in Type I diabetes patients. These experiments are typically carried out in the absence of food and unusual physical activity influences. Prior to the experimental insulin bolus, a continuous infusion of basal insulin is adjusted to establish a constant, normal BGC. The experimental insulin bolus is then given, and BGC is maintained in the normal range by intravenous infusion of glucose to compensate for net glucose uptake from the blood in response to the insulin bolus. The glucose infusion rate (GIR) required to do so is recorded. Graphs of the GIR as a function of time define the pharmacodynamic effect (a.k.a. time-action) profiles of the various types of insulin, including the rapid-acting insulin analogs and formulations. As discussed below, such graphs can provide a basis for the way art insulin pumps calculate IOB, as well as provide a basis for calculations under the present invention.

It is widely appreciated that in a euglycemic glucose clamp study, GIR depends not only on the type of insulin administered, the route of administration, and the length of time after insulin administration at which GIR is measured, but also minimally on the amount of insulin administered and the patient's insulin sensitivity. Insulin sensitivity has been defined in several different ways. One way, as a rate of net glucose uptake at a given blood concentration of insulin per kilogram of body mass, illustrates that the patient's body mass and factors that affect the patient's blood concentration of insulin, such as clearance rate, also play a role in determining GIR. To avoid confusion and for the sake of simplicity, the term "insulin responsiveness" ($R_I$) is employed in this specification. As employed here, "insulin responsiveness" captures all of the factors that would affect GIR for a specific patient taking a specific type of insulin by a specific route of administration, except for the amount of insulin administered and the length of time after insulin administration. "Insulin responsiveness" reflects the patient's body mass, the patient's insulin sensitivity (according to the definition above), and all other patient-specific and insulin-specific factors that affect GIR, including the type of insulin, its route of administration (generally subcutaneous for typical insulin pump users), and the rate at which it is cleared from the patient's body.

By the nature of the euglycemic glucose clamp experiment, GIR equals the rate of net glucose uptake (grams per minute). The area under the GIR versus time curve, or put another way, the integral of GIR over time (t, in minutes), from the time of insulin infusion until such time as the pharmacodynamic effect of that insulin is exhausted, equals the total amount of net glucose uptake (grams) in response to the insulin bolus. As an approximation, it is often assumed that total net glucose uptake is proportional to the insulin bolus amount. This assumption of approximate proportionality is consistent with both the insulin-to-carbohydrate ratio concept and also the high blood glucose correction bolus concept, in which the absolute decrease in BGC is proportional to the amount of correction bolus insulin, independent of the initial BGC. These two concepts form the backbone of insulin therapy in Type I diabetes. It is noteworthy that the insulin-to-carbohydrate ratio concept, while imperfect, works best when only carbohydrate is consumed; in a euglycemic glucose clamp study nothing is eaten, and only glucose is infused. Therefore, the approximation that total net glucose uptake is proportional to the insulin bolus amount is reasonable in this context. If $R_I$ is constant throughout the duration of insulin action, as it typically is in a euglycemic glucose clamp study, then the integral of GIR over time (total glucose infused=total net glucose uptake, in grams) from the time of insulin infusion (t0) until such time as the pharmacodynamic effect of that insulin is exhausted (t∞), equals $R_I$ (insulin responsiveness, in grams of net glucose uptake per unit of insulin bolused) multiplied by $I_i$ (amount of insulin bolused, in units):

$$\int_{t0}^{t\infty} [GIR] dt = R_I \cdot I_i.$$

Thus, $R_I$ can be thought of as analogous to an insulin-to-carbohydrate ratio, or more accurately, a carbohydrate-to-insulin ratio.

The preceding discussion considers the entire bolus of insulin and its entire effect. However, a formal definition of IOB and a description of the present invention within the euglycemic glucose clamp framework, require a more general treatment of the relationship between GIR, $I_i$, $R_I$, and time to make it possible to analyze situations in which only part of the pharmacodynamic effect of a dose of insulin has been realized. Toward that end, it is helpful to introduce a new term, "pharmacodynamic insulin unit equivalents", abbreviated PDIUE, which is defined below. It should be appreciated that although it is convenient to formally define IOB and PDIUE within the euglycemic glucose clamp framework, both IOB and PDIUE, and the concepts they represent, have wide applicability, as exemplified in this specification.

One way to think of PDIUE is as an accounting of insulin amounts allocated to intervals of time according to the pharmacodynamic effect of the insulin over those time intervals. Therefore, the quantity PDIUE is expressed in units, and over the full action time of a bolus of insulin, the total amount of PDIUE must equal the amount of the insulin bolus:

$$\int_{t0}^{t\infty} [d(PDIUE)/dt] dt = I_i.$$

Thus, $$\int_{t0}^{t\infty} [d(PDIUE)/dt] dt$$

represents the full insulin bolus from a pharmacodynamic, rather than dosing, perspective. Like PDIUE itself, the quantity $\int [d(PDIUE)/dt] dt$ is expressed in units.

The way in which PDIUE from an insulin bolus is allocated to time intervals can be determined in a euglycemic glucose clamp study, and the euglycemic glucose clamp framework is ideal for defining PDIUE in a rigorous and quantitative manner. PDIUE may be defined within the euglycemic glucose clamp framework by its relationship to $I_i$, GIR, $R_I$, and time in a general treatment in which the time intervals considered need not begin with the time of the insulin bolus nor end with a time at which the pharmacodynamic effect of the insulin bolus is exhausted, and in which GIR, $R_I$, and PDIUE all may vary with time, although $R_I$, because of the nature of a euglycemic glucose clamp experiment, generally will not vary. Specifically, PDIUE is defined within the euglycemic glucose clamp framework by two simultaneous equations:

$$\int_{t0}^{t\infty} [d(PDIUE)/dt] dt = I_i, \quad \text{equation 1}$$

which is discussed above, and $$\int_{t1}^{t2} [GIR] dt = \int_{t1}^{t2} [R_I \cdot d(PDIUE)/dt] dt, \quad \text{equation 2}$$

wherein t1 and t2 are the bounds of a time interval. Equation 2 derives from the fact that in a euglycemic glucose clamp experiment, over any time interval, the amount of glucose infused, $$\int_{t1}^{t2} [GIR] dt,$$

must equal the amount of net glucose uptake, which is $$\int_{t1}^{t2} [R_I \cdot d(PDIUE)/dt] dt.$$

The amount of net glucose uptake, $$\int_{t1}^{t2} [R_I \cdot d(PDIUE)/dt] dt,$$

is by definition the integral of the rate of insulin action; that rate is expressed here as $R_I \cdot d(PDIUE)/dt$. In turn, the rate of insulin action is the product of insulin responsiveness, $R_I$, and a "rate of insulin usage" in the pharmacodynamic sense, expressed as $d(PDIUE)/dt$. Thus, $d(PDIUE)/dt$ represents the "rate of insulin usage" in the pharmacodynamic sense, and accordingly, the quantity $d(PDIUE)/dt$ is expressed in units per minute or per hour. ("Rate of PDIUE expenditure" is used herein synonymously with $d(PDIUE)/dt$.) This pharmacodynamic notion of "insulin usage" connects the definition of PDIUE with one of the ways in which IOB has been described, "the amount of insulin that has already been delivered to the body, but which has not yet been used" (see above). The concept of PDIUE may also be grasped by thinking of $$\int_{t1}^{t2} [d(PDIUE)/dt] dt$$

as "an amount of insulin usage" in the pharmacodynamic sense over the time interval from t1 to t2, hence the term, "pharmacodynamic insulin unit equivalents". ("Amount of PDIUE expenditure" is used herein synonymously with $$\int_{t1}^{t2} [d(PDIUE)/dt] dt.)$$

Importantly, in the context of PDIUE discussion, the phrases "amount of insulin usage", "rate of insulin usage", "insulin used", and the like, are meant to describe amounts of insulin as allocated to time intervals according to pharmacodynamic effect, such as can be measured in a euglycemic glucose clamp study. These phrases are not meant to describe amounts of insulin infused during particular time intervals or amounts of insulin allocated to time intervals based on pharmacokinetic disposition, such as an amount of insulin cleared during a particular time interval.

For example, if a 10.0 unit bolus of insulin is given at noon, and GIR rises from and falls back to zero by 4 PM, and between noon and 4 PM total net glucose uptake is 100 grams with 35 of those 100 grams being taken up between 1 PM and 2 PM, then assuming $R_I$ to be constant, 35% or 3.5 units of PDIUE from the 10.0 unit bolus is allocated to the time interval from 1 PM to 2 PM. That is, $$\int_{t1}^{t2} [d(PDIUE)/dt] dt = 3.5 \text{ units}$$

when t1 is 1 PM and t2 is 2 PM. Also, on average, $d(PDIUE)/dt$ over this time interval is 3.5 units per hour. Note that PDIUE amounts reflect directly the effect of insulin during the time interval and do not reflect directly either the amount of insulin infused during the time interval (none between 1 PM and 2 PM in this example) or the amount of insulin present in or cleared from the body during the time interval (unknown).

The concept of PDIUE is a valuable one for defining IOB within the euglycemic glucose clamp framework. If IOB is understood as an insulin credit for the subsequent effect of bolus insulin infused recently enough to have not yet exerted its full effect, then IOB may be defined as a special case of $$\int_{t1}^{t2} [d(PDIUE)/dt] dt$$

in which t1 is the then present time of calculation, tc, and t2 is t∞, a subsequent time when the effect of the bolused insulin is exhausted:

$$\int_{tc}^{t\infty} [d(PDIUE)/dt] dt = IOB.$$

In other words, the number of units of IOB insulin is the number of units of PDIUE from the then present time of calculation until such time as the effect of bolus insulin is exhausted.

Although the euglycemic glucose clamp framework provides a convenient context within which define both PDIUE and IOB, both terms have wide applicability, and the effect of both PDIUE and IOB insulin may vary with circumstance. Either one may decrease BGC, dispose of glucose from food already eaten, dispose of glucose from food to be eaten, compensate for diminished insulin responsiveness, etc., or perform two or more of these functions simultaneously. PDIUE and IOB insulin quantities do not depend on the BGC, food eaten, or insulin responsiveness, but rather on amounts of insulin bolused, time elapsed since bolusing, and the pharmacodynamic time-action profile of the specific type of insulin infused in the specific patient by their specific route of administration, as could be measured in a euglycemic glucose clamp study if one were performed. Whether or not a euglycemic glucose clamp study actually is performed does not affect PDIUE and IOB insulin quantities. Furthermore, many of the concepts and relationships regarding PDIUE discussed above in the context of a euglycemic glucose clamp experiment hold true generally. For instance, regardless of the circumstances, $d(PDIUE)/dt$ can be considered to represent "a rate of insulin usage" in the pharmacodynamic sense;

$$\int_{t1}^{t2} [d(PDIUE)/dt] dt$$

can be understood as "an amount of insulin usage" in the pharmacodynamic sense from t1 to t2; the total number of units of PDIUE from an insulin bolus equals the number of units of insulin bolused, that is, $$\int_{t0}^{t\infty} [d(PDIUE)/dt] dt = I_i;$$

and the number of units of IOB is the number of units of PDIUE, or the "amount of insulin usage" in the pharmacodynamic sense, from the then present time of calculation until a subsequent time when the effect of bolus insulin is exhausted, that is, $$\int_{tc}^{t\infty} [d(PDIUE)/dt] dt = IOB.$$

It is noteworthy that although the more general concept of $$\int_{t1}^{t2} [d(PDIUE)/dt] dt$$

has been disclosed in the context of predicting BGC (see U.S. Pat. No. 6,925,393, U.S. Pat. No. 5,822,715, US 2006/137695), the art does not describe communication of $$\int_{t1}^{t2} [d(PDIUE)/dt] dt$$

to a user, except in the special case of IOB.

Now consider further the scope and limitations of the IOB feature of art insulin pumps with respect to information provided, user options, and recommended application. Art insulin pumps inform a user about current IOB and the amount of time until current IOB declines to zero. The display of past and future IOB values has not been described. In other words, art insulin pumps do not display what IOB was or will be at any time other than the current clock time of the insulin pump.

Art insulin pumps provide the option for a user to set the maximum duration of IOB, that is, the amount of time after an insulin bolus until the effect of that bolus is considered to be exhausted. In other words, art insulin pumps allow a user to shorten or lengthen an internal reference insulin time-action profile that is used to calculate IOB. This adjustment is to be made based on personal experience and/or the advice of a healthcare professional.

According to the art, the principal application for the IOB feature is avoidance of hypoglycemia. An insulin pump user is advised to consider IOB as an insulin credit which, when included in an analysis of carbohydrate—insulin balance, might alert the user to impending hypoglycemia. Typically, a user is instructed to assume that all of the IOB will function as a correction bolus, lowering BGC by the amount expected under basal conditions, that is, when no meal or unusual physical activity effects are operative. If this assumption suggests that the IOB will overcorrect, causing hypoglycemia, then the user is instructed to take action, such as consumption of carbohydrate. It is, however, frequently the case that BGC is measured and IOB is calculated under non-basal conditions, especially when a recent meal is having an effect. The art sometimes instructs a user to assume that only the IOB from a correction bolus, as opposed to insulin dosed for a meal, will function as a correction bolus at the time of IOB calculation. This assumption rests on the premise that any insulin meant to cover food was well-matched to the meal—that is, the effects on BGC of the meal and the insulin dosed to cover it would continuously offset one another—a sort of pseudobasal condition. However, in reality, it is often the case that insulin dosed for food is not well-matched to the meal and a distinctly non-basal, and non-pseudobasal, condition exists. Moreover, because an IOB calculation informs a user only about his total insulin credit from the then present time of calculation until the effect of bolus insulin is exhausted, IOB calculations provide insufficient information to predict potential shorter term, interim deficiencies or excesses that could result in hyper- or hypoglycemia.

One refinement to the art includes the concept that recommended bolus amounts be calculated considering current IOB and also correcting for the current rate of change of BGC, as determined by a continuous glucose monitor (US 2006/173406). Another provides for the prediction of BGC based on the concept of $$\int_{t1}^{t2} [d(PDIUE)/dt] dt,$$

wherein t2 may be other than t∞, thus enabling the prediction of BGC at time points prior to the exhaustion of the effect of bolused insulin (U.S. Pat. No. 6,925,393). In both cases, a basal or pseudobasal condition (as defined above) is assumed, except that in the latter case, the future time dependence of the effect of known amounts of carbohydrate consumed may be figured in, provided that the time course of the introduction of glucose into the blood from the carbohydrate is known. Unfortunately, the management of BGC suffers from several significant problems that are not effectively addressed by the art. The teachings of the art are particularly inadequate when poorly understood or complex meals are consumed. Poorly understood meals, that is, meals having unknown components or unknown component quantities, are inherently difficult to manage BGC after because the art requires an understanding of a meal's composition to determine appropriate insulin dosing. Complex meals, that is, meals having many, diverse components, may be well-understood from the standpoint of composition, but they often include sources of protein and fat. Application of the insulin-to-carbohydrate ratio concept to complex meals frequently fails to maintain BGC within, or even near, the target range, and different complex meals often require different insulin-to-carbohydrate ratios, even when they are consumed at the same time of day without variation in physical activity. Complex meals are troublesome largely because the insulin-to-carbohydrate ratio concept considers only the carbohydrate content of a meal, but the fat and protein content of a meal are also important factors that influence the amount and timing of insulin required. High-fat meals are sometimes best managed by infusing some insulin at mealtime and additional insulin, beyond that calculated with the usual insulin-to-carbohydrate ratio, at later times. Notwithstanding the proposal of calculations (U.S. Pat. No. 6,835,175), the art offers no quantitative rules to guide the dosing of insulin based on consideration of the fat and protein content of meals. Poor understanding of meals and the vagaries of complex meals can lead to severe hyper- or hypoglycemia appearing in a fraction of an hour due to imbalances between meal and insulin effects. Furthermore, even when the correct total amount of insulin for a meal is dosed, as judged by target BGC being attained when the meal and insulin effects have been exhausted, in the interim, severe, transient hyper- or hypoglycemia can occur due to imbalances between the meal and insulin effects over short time intervals, for example between 90 and 150 minutes after the start of a meal. Unfortunately, the art does not teach an insulin pump user how to relate insulin pharmacodynamic information to BGC data in order to evaluate in quantitative terms the opposing influences of food and insulin over short time intervals.

Independently of meal effects, the management of BGC under conditions of physical activity variation and other circumstances, such as hormonal fluctuation and extreme emotion, is complicated in ways that are also not reliably addressed in a quantitative manner by the teachings of the art.

As a result, when these factors are at play, severe hyper- or hypoglycemia can crop up in a fraction of an hour. The art does not teach an insulin pump user how to relate insulin pharmacodynamic information to BGC data in order to quantitatively evaluate the interplay of insulin effects, physical activity, hormonal fluctuation, and extreme emotion effects over short time intervals.

Regarding BGC management both after meals and/or with physical activity variation, according to the art, exact repetition of meals and/or physical activity coupled with learning from trial and error helps to establish standard protocols for insulin dosing that lead to outcomes that are closer to ideal. However, exact repetition is impractical in many situations, and exact repetition inherently limits flexibility. Moreover, each new situation must be worked out by trial and error which, due to the inevitable errors, often results in severe hyper- or hypoglycemia. Consequently, exact repetition coupled with learning from trial and error is a weak, partial solution to the problems of BGC management.

Finally, insulin delivery problems, such as insulin infusion site deterioration, occur occasionally and can be dangerous if not remedied soon enough. Infusion site deterioration leads initially to unexpected hyperglycemia and may lead to subsequent, unexpected hypoglycemia if insulin delivery is slowed, rather than completely blocked. Insulin delivery problems, such as infusion site deterioration, can be corrected once detected, but their detection can be difficult in the context of a flexible lifestyle because BGC is the main indicator of insulin delivery problems, and in the context of a flexible lifestyle, the art does a poor job of teaching how to predict and manage BGC. This makes it difficult for an insulin pump user to determine whether aberrant BGC is due to an insulin delivery problem or due to suboptimal insulin dosing instead. The art does not teach an insulin pump user how to relate insulin pharmacodynamic information from an insulin pump to BGC data and his knowledge of the various factors that affect BGC in order to identify an insulin delivery problem in a timely fashion.

Because the teachings of the art are inadequate to enable even an experienced and skillful insulin pump user to enjoy a flexible lifestyle while consistently and reliably maintaining his BGC within or near the target range, new tools are needed. Toward this end, the present invention is disclosed.

SUMMARY

Embodiments of the present invention comprise a system for predicting and managing blood glucose concentration that calculates a recent past amount and/or rate of insulin usage in the pharmacodynamic sense, or specifically, a recent past $$\int_{t1}^{t2} [d(PDIUE)/dt] dt$$

and/or d(PDIUE)/dt, or synonymously, a recent past amount and/or rate of PDIUE expenditure, in order to correlate it with recent past BGC data and communicate the relationship between them to a user. A system can accept user input defining how the user expects the relationship between the amount and/or rate of PDIUE expenditure on one hand and BGC on the other hand to evolve over the near future. Based on this user input, a system can predict the evolution of near future BGC. In response to the system's prediction, the user can pursue a desired BGC result by optionally adjusting insulin delivery programming, consuming carbohydrate, and/or taking other action. A system of the invention may be integrated with an insulin delivery system, such as an insulin pump, and/or with a BGC monitoring device, such as a point-in-time glucometer or a continuous glucose monitor. Such integration may facilitate the transfer of insulin dosing information and BGC data to a system of the invention, the transfer otherwise being accomplished by manual input using art methods, a necessity for the capture of insulin dosing information related to insulin injection by syringe. Integration may also facilitate the adoption of insulin delivery recommendations, which a system of the invention may make, by facilitating transfer of such recommendations to an insulin delivery system. Integration may also produce economies such as the need for fewer graphical display screens.

In one embodiment of the invention, the amount and/or rate of PDIUE expenditure over any time interval, beginning up to five hours in the past and ending up to seven hours in the future, may be calculated and optionally displayed by the system. In another embodiment of the invention, the calculation the amount and/or rate of PDIUE expenditure may consider insulin already infused, insulin programmed to be infused, and/or insulin proposed to be infused. In another embodiment of the invention, the system may analyze the relationship between a recent past amount and/or rate of PDIUE expenditure on one hand and BGC on the other hand over the same time interval and optionally display not only an actual past amount and/or rate of PDIUE expenditure, but also a calculated past BGC-neutral amount and/or rate of PDIUE expenditure, these being a hypothetical past amount and/or rate of PDIUE expenditure that according to calculation would have resulted in no net change in BGC over the time interval, and that differ from the actual past amount and/or rate of PDIUE expenditure, respectively, if BGC did, in fact, change. In another embodiment of the invention, the system may accept as input and optionally display a user prediction of a near future BGC-neutral amount and/or rate of PDIUE expenditure, these being an amount and/or rate of PDIUE expenditure that the user predicts will result in no net change in BGC over the near future, the user prediction made based in part on the calculated past BGC-neutral amount and/or rate of PDIUE expenditure, respectively. In another embodiment of the invention, the system may calculate and optionally graphically display a function of predicted BGC versus time that starts with a recent BGC value and evolves according to the relationship between a user predicted near future BGC-neutral amount and/or rate of PDIUE expenditure on one hand and an anticipated amount and/or rate of PDIUE expenditure from insulin delivery, respectively, on the other hand. In another embodiment of the invention, the system may allow the user to test, before committing to its implementation, an insulin delivery scenario for its effect on the anticipated amount and/or rate of PDIUE expenditure from insulin delivery and/or on a system calculated function of predicted BGC versus time. In another embodiment of the invention, the system may calculate, and optionally display and/or communicate to an insulin delivery system, a recommended insulin delivery scenario that approximates a user-specified near future amount and/or rate of PDIUE expenditure, the calculation considering insulin already infused and insulin programmed to be infused, the latter being optionally subject to change. In another embodiment of the invention, the various capabilities of the other embodiments of the invention may, at the discretion of the user, be carried out multiple times during a period of several hours. In another embodiment of the invention, any other embodiment of the invention, that has as an element a PDIUE-related amount and/or rate, may incorporate as an element a time-dependent function of any of its PDIUE-related amount and/or rate elements. The aforementioned capabilities of the present invention are useful in the management of BGC.

An embodiment of the invention is a device for managing blood glucose concentration comprising a means for inputting at least two recent past blood glucose concentration data items, where each data item comprises a blood glucose concentration value and a time-of-measurement value. The device further comprises a means for inputting insulin delivery data items, where each data item comprises an insulin dosage amount and a time-of-delivery value; a means for inputting insulin time-action profile data; a means for inputting patient $R_{BGC/I}$ data, the responsiveness of the patient's blood glucose concentration to insulin, optionally as a function of time of day; and a means for inputting phamacodynamic insulin unit equivalent expenditure (PDIUE) data. The PDIUE data are selected from the group consisting of d(PDIUE)/dt data, a rate of pharmacodynamic insulin unit equivalent expenditure; and $$\int_{t1}^{t2} [d(PDIUE)/dt]dt \text{ data,}$$

an amount of pharmacodynamic insulin unit equivalent expenditure between times $t_1$ and $t_2$, where $t_1$ precedes $t_2$. The device is further comprised of a microprocessor connected to the input means, where the microprocessor is also connected to a digital memory, and to wired or wireless communication means. The microprocessor is configured to perform calculations based upon inputted recent past blood glucose concentration data, inputted insulin delivery data, inputted insulin time-action profile data, inputted patient $R_{BGC/I}$ data, and at least one of: inputted d(PDIUE)/dt data, and inputted $$\int_{t1}^{t2} [d(PDIUE)/dt]dt \text{ data.}$$

The microprocessor is configured to calculate d(PDIUE)/dt or $$\int_{t1a}^{t2a} [d(PDIUE)/dt]dt.$$

The times $t_{1a}$ and $t_{2a}$ may be independently the same as, or different from, $t_1$ and $t_2$. The microprocessor is optionally configured to calculate $$\int_{tc}^{t\infty} [d(PDIUE)/dt]dt,$$

IOB, where $t_c$ is the current time and $t_\infty$ represents a future time when the pharmacodynamic effect of delivered insulin is exhausted. The microprocessor is also configured to calculate blood glucose concentration. There is a display connected to the microprocessor for displaying the calculation results including at least one of d(PDIUE)/dt and $$\int_{t1a}^{t2a} [d(PDIUE)/dt]dt.$$

In addition, $$\int_{tc}^{t\infty} [d(PDIUE)/dt]dt$$

may optionally be displayed. Blood glucose concentration results are also displayed. Optionally, the device may use values for $t_1$ and $t_{1a}$ that are no more than five hours in the past, and values for $t_2$ and $t_{2a}$ that are no more than seven hours in the future, and where d(PDIUE)/dt corresponds to a time no more than five hours in the past and no more than seven hours in the future. Optionally, the device may calculate and display d(PDIUE)/dt and [d(PDIUE)/dt] dt that are BGC-neutral. Optionally, the device may use inputted d(PDIUE)/dt and [d(PDIUE)/dt] dt that are BGC-neutral. Optionally, the device may use either a keyboard or a touch screen as a means for inputting data. The keyboard and/or touch screen facilitate the manual input of data, and in addition the touch screen may optionally function as a display. The device may optionally comprise a glucose meter connected to the microprocessor, and the device may optionally comprise an insulin pump connected to the microprocessor. The optional glucose meter and insulin pump may be fully integrated with a device of the invention, or they may be separate devices which are in communication with a device of the invention. The communication between a device of the invention and a glucose meter and/or insulin pump may occur via either wired or wireless communication means.

An embodiment of the invention is a device for managing blood glucose concentration comprising a means for inputting at least two recent past blood glucose concentration data items, where each data item comprises a blood glucose concentration value and a time-of-measurement value. The device further comprises a means for inputting insulin delivery data items, where each data item comprises an insulin dosage amount and a time-of-delivery value; a means for inputting insulin time-action profile data; a means for inputting patient $R_{BGC/I}$ data, the responsiveness of the patient's blood glucose concentration to insulin, optionally as a function of time of day; and a means for inputting phamacodynamic insulin unit equivalent expenditure data. The PDIUE data are selected from the group consisting of d(PDIUE)/dt data, a rate of pharmacodynamic insulin unit equivalent expenditure; and $$\int_{t1}^{t2} [d(PDIUE)/dt]dt \text{ data,}$$

an amount of pharmacodynamic insulin unit equivalent expenditure between times $t_1$ and $t_2$, where $t_1$ precedes $t_2$. The device is further comprised of a microprocessor connected to the input means, where the microprocessor is also connected to a digital memory, and to wired or wireless communication means. The microprocessor is configured to perform calculations based upon inputted recent past blood glucose concentration data, inputted insulin delivery data, inputted insulin time-action profile data, inputted patient $R_{BGC/I}$ data, and at least one of: inputted d(PDIUE)/dt data, and inputted $$\int_{t1}^{t2}[d(PDIUE)/dt]dt \text{ data.}$$

The microprocessor is configured to calculate d(PDIUE)/dt and/or $$\int_{t1a}^{t2a}[d(PDIUE)/dt]dt.$$

The times $t_{1a}$ and $t_{2a}$ may be independently the same as, or different from, $t_1$ and $t_2$. The microprocessor is optionally configured to calculate $$\int_{tc}^{t\infty}[d(PDIUE)/dt]dt,$$

IOB. There is a display connected to the microprocessor for displaying the calculation results including at least one of d(PDIUE)/dt and $$\int_{t1a}^{t2a}[d(PDIUE)/dt]dt.$$

In addition, $$\int_{tc}^{t\infty}[d(PDIUE)/dt]dt$$

may optionally be displayed. Optionally, the device may use values for $t_1$ and $t_{1a}$ that are no more than five hours in the past, and values for $t_2$ and $t_{2a}$ that are no more than seven hours in the future, and where d(PDIUE)/dt corresponds to a time no more than five hours in the past and no more than seven hours in the future. Optionally, the device may calculate and display d(PDIUE)/dt and [d(PDIUE)/dt] dt that are BGC-neutral. Optionally, the device may use inputted d(PDIUE)/dt and [d(PDIUE)/dt] dt that are BGC-neutral. Optionally, the device may use either a keyboard or a touch screen as a means for inputting data. The keyboard and/or touch screen facilitate the manual input of data, and in addition the touch screen may optionally function as a display. The device may optionally comprise a glucose meter connected to the microprocessor, and the device may optionally comprise an insulin pump connected to the microprocessor. The optional glucose meter and insulin pump may be fully integrated with a device of the invention, or they may be separate devices which are in communication with a device of the invention. The communication between a device of the invention and a glucose meter and/or insulin pump may occur via either wired or wireless communication means.

An embodiment of the invention is a device for managing blood glucose concentration comprising a means for inputting insulin delivery data items, where each data item comprises an insulin dosage amount and a time-of-delivery value; a means for inputting insulin time-action profile data, and a means for inputting phamacodynamic insulin unit equivalent expenditure data. The PDIUE data are selected from the group consisting of d(PDIUE)/dt data, a rate of pharmacodynamic insulin unit equivalent expenditure; and $$\int_{t1}^{t2}[d(PDIUE)/dt]dt \text{ data,}$$

an amount of pharmacodynamic insulin unit equivalent expenditure between times $t_1$ and $t_2$, where $t_1$ precedes $t_2$. The device is further comprised of a microprocessor connected to the input means, where the microprocessor is also connected to a digital memory, and to wired or wireless communication means. The microprocessor is configured to perform calculations based upon inputted insulin delivery data, inputted insulin time-action profile data, and at least one of: inputted d(PDIUE)/dt data, and inputted $$\int_{t1}^{t2}[d(PDIUE)/dt]dt \text{ data.}$$

The microprocessor is configured to calculate d(PDIUE)/dt and/or $$\int_{t1a}^{t2a}[d(PDIUE)/dt]dt.$$

The times $t_{1a}$ and $t_{2a}$ may be independently the same as, or different from, t1 and t2. The microprocessor is optionally configured to calculate $$\int_{tc}^{t\infty}[d(PDIUE)/dt]dt,$$

IOB. There is a display connected to the microprocessor for displaying the calculation results including at least one of d(PDIUE)/dt and $$\int_{t1a}^{t2a}[d(PDIUE)/dt]dt.$$

In addition, $$\int_{tc}^{t\infty}[d(PDIUE)/dt]dt$$

may optionally be displayed. Optionally, the device may use values for $t_1$ and $t_{1a}$ that are no more than five hours in the past, and values for $t_2$ and $t_{2a}$ that are no more than seven hours in the future, and where d(PDIUE)/dt corresponds to a time no more than five hours in the past and no more than seven hours in the future. Optionally, the device may use either a keyboard or a touch screen as a means for inputting data. The keyboard and/or touch screen facilitate the manual input of data, and in addition the touch screen may optionally function as a display. The device may optionally comprise an insulin pump connected to the microprocessor. The optional insulin pump may be fully integrated with a device of the invention, or it may be a separate device which is in communication with a device of the invention. The communication between a device of the invention and an insulin pump may occur via either wired or wireless communication means.

An embodiment of the invention is a device for managing blood glucose concentration comprising a means for inputting insulin delivery data items, where each data item comprises an insulin dosage amount and a time-of-delivery value; and a means for inputting insulin time-action profile data. The device is further comprised of a microprocessor connected to the input means, where the microprocessor is also connected to a digital memory, and to wired or wireless communication means. The microprocessor is configured to perform calculations based upon inputted insulin delivery data and inputted insulin time-action profile data. The microprocessor is configured to calculate d(PDIUE)/dt and/or $$\int_{t1a}^{t2a} [d(PDIUE)/dt] dt$$

between times $t_{1a}$ and $t_{2a}$ where $t_{1a}$ precedes $t_{2a}$. The microprocessor is optionally configured to calculate $$\int_{tc}^{t\infty} [d(PDIUE)/dt] dt,$$

IOB. There is a display connected to the microprocessor for displaying the calculation results including at least one of d(PDIUE)/dt and $$\int_{t1a}^{t2a} [d(PDIUE)/dt] dt.$$

In addition, $$\int_{tc}^{t\infty} [d(PDIUE)/dt] dt$$

may optionally be displayed. Optionally, the device may use either a keyboard or a touch screen as a means for inputting data. The keyboard and/or touch screen facilitate the manual input of data, and in addition the touch screen may optionally function as a display. The device may optionally comprise an insulin pump connected to the microprocessor. The optional insulin pump may be fully integrated with a device of the invention, or it may be a separate device which is in communication with a device of the invention. The communication between a device of the invention and an insulin pump may occur via either wired or wireless communication means.

An embodiment of the invention is a device for managing blood glucose concentration comprising a means for inputting insulin time-action profile data and a means for inputting phamacodynamic insulin unit equivalent expenditure data. The PDIUE data are selected from the group consisting ofd (PDIUE)/dt data, a rate of pharmacodynamic insulin unit equivalent expenditure; and $$\int_{t1}^{t2} [d(PDIUE)/dt] dt \text{ data,}$$

an amount of pharmacodynamic insulin unit equivalent expenditure between times $t_1$ and $t_2$, where $t_1$ precedes $t_2$. The device is further comprised of a microprocessor connected to the input means, where the microprocessor is also connected to a digital memory. The microprocessor is configured to perform calculations based upon inputted insulin time-action profile data, and at least one of: inputted d(PDIUE)/dt data, and inputted $$\int_{t1}^{t2} [d(PDIUE)/dt] dt \text{ data.}$$

The microprocessor is configured to calculate an insulin delivery-over-time function. There is a display connected to the microprocessor for displaying an insulin delivery-over-time function. Optionally, the device may use either a keyboard or a touch screen as a means for inputting data. The keyboard and/or touch screen facilitate the manual input of data, and in addition the touch screen may optionally function as a display. The device may optionally be configured to output an insulin delivery-over-time function to an insulin pump. The device of the invention may further comprise wired and/or wireless communication means.

A block diagram of a device of the invention is shown in FIG. 1. A microprocessor is connected to a clock, digital memory, manual input means, and a display. The clock provides time values used in calculations. The digital memory is used to store programming code and data used by the microprocessor. The manual input means may comprise a keyboard and/or a touch sensitive screen. The display is used for displaying results to a user, and the display may also act as a touch sensitive screen. The microprocessor is optionally connected to a wired and/or a wireless communications interface. The communications interface(s) facilitate the import and export of data. A device of the invention may use the communications interface(s) to import and export PDIUE data, insulin time-action profile data, patient $R_{BGC/I}$ data, and the like. The communications interface(s) may communicate over the internet or via other electronic communication protocols. The microprocessor is optionally connected to a glucose meter. The glucose meter may be integrated within the device, or the glucose meter may be a separate device connected to the microprocessor via a wired or wireless communication means. The glucose meter may optionally be connected to a patient. The microprocessor is optionally connected to an insulin pump. The insulin pump may be integrated within the device, or the insulin pump may be a separate device connected to the microprocessor via a wired or a wireless communication means. The insulin pump may be optionally connected to a patient.

BRIEF DESCRIPTION OF THE DRAWINGS

FIG. 1 A block diagram of an embodiment of a device of the invention.

DETAILED DESCRIPTION

Definitions

The following are definitions of terms used in this specification.

The term "insulin" as used herein means any formulation of either regular human insulin or any insulin analog, for example lispro, aspart, or glulisine, and implies no particular means, route, or site of its delivery. It is recognized that insulin pharmacodynamics may depend on the specific insulin or insulin analog formulation being dosed; and therefore, PDIUE calculations under the present invention may vary accordingly.

The term "insulin delivery system" as used herein means a system that accomplishes the dosing of insulin to a patient in need of insulin therapy. The term "insulin delivery system" encompasses all meanings of the term "insulin pump" and other types of insulin delivery systems as well, including insulin syringes, insulin pens, insulin inhalation devices, insulin nasal spray devices, and oral dosage forms such as pills. The term "insulin delivery system" implies no particular type of insulin or route of administration, and therefore is not limiting to lispro, aspart, or glulisine, or to subcutaneous versus intravenous or intraperitoneal infusion, for instance. The term "insulin delivery system" includes all of the components that may help accomplish the dosing of insulin to a patient in need of insulin therapy, including, but not limited to, a liquid pump, insulin solution, a microprocessor, software, and a user interface.

The term "insulin time-of-delivery value" as used herein means a time or an interval of time during which insulin is, or was, or will be delivered to a patient. The "time-of-delivery value" may be a point in time, at which an amount of insulin is delivered, or a range of time, for example 30 minutes, during which a bolus of insulin is delivered.

The term "insulin delivery-over-time function" as used herein means a function calculated by a system of the invention that describes the delivery of insulin to a patient over a period of time. Such a function may be used to describe past, present, and/or future insulin delivery. An insulin delivery-over-time function may be used to program an insulin pump. An "insulin delivery-over-time function" describes the time course of insulin delivery from an insulin delivery scenario.

The terms "pharmacodynamic insulin unit equivalents" and "amount of PDIUE expenditure" and "rate of PDIUE expenditure" and the like are defined in the section above that is titled, "Description of the Related Art and Definition of Pharmacodynamic Insulin Unit Equivalents and Related Expressions". The term "rate of PDIUE expenditure", which is synonymous with "d(PDIUE)/dt", encompasses both instantaneous and average d(PDIUE)/dt.

The term "BGC-adjusted PDIUE expenditure" as used herein means a hypothetical past, present, or future amount and/or rate of PDIUE expenditure that according to calculation would have been expected, is expected, or would be expected to result in a specified change in BGC. When the specified change in BGC is zero, "BGC-adjusted PDIUE expenditure" is equivalent to "BGC-neutral PDIUE expenditure". It is understood that throughout this specification, the term "BGC-adjusted PDIUE expenditure" may optionally be substituted for the term "BGC-neutral PDIUE expenditure". In those cases where the specified change in BGC is non-zero, the calculations and methods described in this specification in the context of BGC-neutral PDIUE expenditure may be adjusted accordingly.

The term "user", as in "user of an insulin pump" or "user of a system of the invention" or "user of a continuous glucose monitor" as used herein means any individual who may operate such devices or act upon information they provide. Typically, a user is the patient whose blood glucose concentration control is enhanced by such devices or systems, but the term "user" may also apply to other interested parties, such as adults who care for a child patient. The user may be more than one person, for instance the patient during daytime and the patient's parents during nighttime.

The term "bolus", used as a noun as in "insulin bolus", as a verb as in "to bolus insulin", and as an adjective as in "bolus insulin", as used herein refers to insulin infused or the act of infusing insulin on an ad hoc basis, as to be distinguished from "basal insulin", which is infused according to a schedule. In the context of insulin pump therapy, bolus insulin is typically infused either as a "standard bolus" (also known as "normal bolus"), that is, infused over less than about five minutes, or as an "extended bolus" (also known as "square wave bolus"), that is, infused continuously or semi-continuously at a constant rate over a period of time ranging from about five minutes up to several hours. Bolus insulin may also be infused according to other protocols, such as at a linearly declining rate over a period of time ranging up to several hours.

The term "basal insulin" as used herein means insulin infused to satisfy the basal insulin need and maintain a steady BGC in the basal state. In the context of insulin injection therapy, basal insulin is be injected once or twice a day according to a schedule. In the context of insulin pump therapy, basal insulin is infused continuously or semi-continuously at a pre-programmed rate (the "basal rate") according to a schedule. For the purpose of this specification, a temporarily, ad hoc increased or decreased basal insulin delivery rate from an insulin pump may optionally be considered to be the sum of the usual basal insulin delivery rate, as determined by the usual schedule, and the insulin delivery rate of an extended insulin bolus or a negative extended insulin bolus, the amount of which is the net increase or decrease, respectively, in the amount of insulin delivered, and the duration of which is the duration of the temporarily, ad hoc increased or decreased basal insulin delivery rate. A negative insulin bolus has the opposite effect on PDIUE calculations as compared with an insulin bolus of the usual, non-negative variety (positive understood) because a negative insulin bolus implies a theoretical negative insulin time-action profile that subtracts from the total of insulin bolus-derived insulin time-action profiles with which it coincides in time.

The terms "basal conditions" and "basal state" as used herein mean a condition or state in which the BGC of a patient is not influenced by a meal or by a significant increase or decrease from the normal level of physical activity or by any other factor that can exert its effect in less than one day. In the basal state a normal amount or rate of basal insulin maintains a steady BGC.

The term "insulin need" as used herein means a quantitative and temporal requirement for insulin delivered in basal and/or bolus modes in order to achieve a steady BGC, especially a steady BGC in the normal or target range. The term "insulin need" also encompasses the concepts of "amount of PDIUE need" and "rate of PDIUE need".

The term "correction bolus" as used herein means insulin infused to "correct" hyperglycemia. Typically, a sliding blood glucose correction scale is employed to calculate the required amount of a correction bolus. Typically, such a sliding blood glucose correction scale is linear, that is, it recommends a fixed amount of insulin for each mg/dL of glucose that BGC should be decreased, independent of the initial BGC. Typically, such sliding blood glucose correction scales assume basal conditions when no meal or unusual physical activity or other effects are operative. In this specification, the term "correction bolus" is not limited to situations of hyperglycemia. As used herein, the term "correction bolus" means a bolus of insulin that is applied toward decreasing BGC even if the anticipated result would be hypoglycemia.

The term "route of administration" as used herein means the way in which insulin is made to enter the body, including, but not limited to subcutaneous, intradermal, intravenous, intraperitoneal, inhalation, nasal, and oral routes. The term "route of administration" may also include the concept of site of administration. For example, insulin may be infused subcutaneously at a variety of sites or locations on the body, including the abdomen, the buttocks, the thigh, and the arm. It is recognized that insulin pharmacodynamics may depend on all aspects of the route, including the specific site of administration, and that adjustments to parameters affecting PDIUE calculations under the present invention may be appropriate when a patient changes any aspect, including a site of subcutaneous insulin infusion.

The term "insulin action" as used herein means an effect of insulin, such as net glucose uptake measured as glucose infused in a euglycemic glucose clamp study, disposal of glucose from a meal, or disposal of glucose resulting in decreasing BGC. Likewise, a "rate of insulin action" as used herein means a rate of insulin effect, such as can be measured as GIR in a euglycemic glucose clamp study or as a rate of BGC decline.

The term "exhausted" as used herein in the context of the pharmacodynamic effect of insulin means that the pharmacodynamic effect of a dose of insulin has diminished over time to the point that it can no longer be measured, for instance by GIR in a euglycemic glucose clamp study. Alternatively, the term "exhausted" applies when nearly all, for example at least 99%, of the total insulin action from a dose of insulin has been realized or become manifest.

The term "glucose monitor" as used herein means a device, either worn by a patient or remote from the patient, that monitors the patient's blood glucose concentration and/or communicates the patient's blood glucose concentration data to a user, for example visually, or to another device or system, for example a system of the invention by wired or wireless means. A glucose monitor and/or its display may be combined with other devices such as an insulin delivery system or a wristwatch or a system of the invention.

The term "blood glucose concentration" (BGC), as used herein and as it relates to glucose monitors means a concentration value of glucose a patient's blood that is either directly measured by sampling blood or related fluids, such as interstitial fluid, or inferred or calculated by measurement of one or more other parameters that correlate with the concentration of glucose in the patient's blood, such as electromagnetic impedance. A BGC value used in the calculations described in this specification may be a single BGC value, an average of recent BGC values, and/or a function of recent BGC values, for example recent values that have been run through a Kalman filter (Diabetes Technology & Therapeutics 2005, volume 7, pp. 15-27).

The terms "blood glucose concentration data" and "BGC data", as used herein mean information about blood glucose concentration, including one or more pairs of BGC values and the times of their measurement or manifestation.

The term "time-of-measurement value", as used herein in the context of blood glucose concentration data means a time of BGC measurement or manifestation.

The term "normal range" as used herein means a range of blood glucose concentration that is typical of individuals with normal glucose metabolism. A BGC in the normal range is equivalent to euglycemia, generally more than 65-80 mg/dL and less than 120-140 mg/dL.

The terms "near the normal range" and "near euglycemia" as used herein mean blood glucose concentration that is slightly above or below the normal range, but which is not reason for concern.

The term "target range" as used herein means a range of blood glucose concentration that is recommended for a patient by the patient's healthcare professional. A target range is typically similar to the normal range, but it may differ from patient to patient and it may depend on experience or circumstance. For example, a target range may be higher during a patient's sleeping hours than during his waking hours.

The terms "blood glucose concentration target" and "target" as used herein mean a patient's optimal BGC, as recommended for the patient by the patient's healthcare professional. A target may be the arithmetic mean, geometric mean, or other function of the bounds of the target range.

The term "continuous" as used herein and as applied to blood glucose monitoring or BGC data means frequently enough to avoid missing significant maxima or minima. Continuous blood glucose monitoring may update every few seconds, for example every 1-5 seconds, every 5-15 seconds, every 15-30 seconds, or every 30-60 seconds, or every few minutes, for example every 1-5 minutes, every 5-15 minutes, or every 15-30 minutes. In this context, the term "continuous" may be synonymous with the term "semi-continuous".

The term "continuous" as used herein and as applied to insulin infusion means truly continuous infusion, or alternatively, insulin infused in pulses hourly or more frequently, such that the time between pulses represents a small fraction of the duration of action of each pulse. In this context, the term "continuous" may be synonymous with the term "semi-continuous".

The terms "user prediction of a BGC-neutral amount or rate of PDIUE expenditure", "user predicts a BGC-neutral amount or rate of PDIUE expenditure", "user predicted BGC-neutral amount or rate of PDIUE expenditure", and the like, as used herein mean a BGC-neutral amount or rate of PDIUE expenditure that a user either believes will become fact or tests to understand what might occur if it were to become fact, or they mean a user acting to establish a BGC-neutral amount or rate of PDIUE expenditure that he either believes will become fact or tests to understand what might occur if it were to become fact. Such a BGC-neutral amount or rate of PDIUE expenditure may originate from a user, or it may be suggested by a system of the invention under the guidance of an algorithm established by a user and executed by the system at the option of the user.

The term "anticipated amount or rate of PDIUE expenditure from insulin delivery" as used herein means a future amount or rate of PDIUE expenditure that is due to either insulin already infused alone, insulin already infused plus insulin programmed to be infused, or insulin already infused plus insulin programmed to be infused, as tentatively adjusted, and that is expected based on a calculation performed by either a user of a system of the invention or by the system of the invention itself.

The term "insulin programmed to be infused", not adjacent to the term "as tentatively adjusted", as used herein means insulin, especially bolus insulin, that has not yet been infused, but which will be infused by an insulin delivery system if the user takes no action to prevent it.

The term "insulin programmed to be infused, as tentatively adjusted" as used herein means insulin that would be programmed to be infused if a user takes a step to implement its delivery programming in test mode.

The term "insulin delivery scenario" as used herein means a totality of relevant insulin delivery elements (standard boluses, extended boluses, negative extended boluses, etc.), regardless of whether the insulin of the elements is already infused, programmed to be infused, or programmed to be infused, as tentatively adjusted. The time course of insulin delivery from an "insulin delivery scenario" is described by an insulin delivery-over-time function.

The term "insulin delivery data" as used herein means insulin dosage information, including insulin already dosed, insulin that will be dosed, and insulin that may be dosed, and including the amount and time of each dosage. The amount and time can be expressed for any type of bolus, for example a standard bolus, in which case it may be expressed as a number of units of insulin dosed at a discreet time, or for example an extended bolus, in which case it may be expressed as a number of units of insulin dosed at a constant rate over a time range, or for example an insulin dosage protocol in which insulin is dosed at a non-constant rate over a time range, in which case it may be expressed as a number of units of insulin dosed at a rate that is a function of time over a time range.

The terms "$R_{BGc/I}$", "$R_{carb/I}$", and "$R_{BGc/carb}$" as used herein mean, respectively, the responsiveness of a patient's BGC to insulin, the amount of carbohydrate disposed of by a unit of insulin, and the responsiveness of the patient's BGC to carbohydrate consumption. Each may be a function, including a continuously varying function, of time of day or other factors.

The term "calculation data time" as used herein, in the context of a calculation performed by a system of the invention, means the time that is associated with time-dependent data used as input into the calculation, as opposed to the clock time at which the calculation is performed. Because a calculation data time is sometimes earlier than the clock time at which the calculation is performed, anticipated or predicted BGC and PDIUE-related values, which may be considered future values relative to the calculation data time, may be considered past, present or future, as opposed to only future, values if judged by the clock time at which the calculation is performed. For example, if the most recent BGC data available is associated with the time 10:00 AM, and if at 11:00 AM (clock time) a calculation is performed to predict BGC using the 10:00 AM BGC data, along with other data associated with 10:00 AM, then predicted BGC values at 10:30 AM and 11:30 AM may both be considered future BGC values because both occur after the calculation data time of 10:00 AM, even though only the 11:30 PM predicted BGC value occurs later than, and therefore is considered a future BGC value relative to, the clock time of 11:00 AM at which the calculation is performed.

The terms "past", "present", and "future" as used herein may mean past, present, and future in their usual sense, that is, referring to a time as being before, simultaneous with, or after, respectively, a then present clock time. In addition, in the context of a calculation performed by a system of the invention, for example referring to a predicted quantity, for example a predicted BGC or a predicted BGC-neutral amount or rate of PDIUE expenditure, or to an act of predicting, for example predicting a BGC or a BGC-neutral amount or rate of PDIUE expenditure, or to an anticipated quantity, for example an anticipated amount or rate of PDIUE expenditure from insulin delivery, or to an act of anticipating, for example anticipating an amount or rate of PDIUE expenditure from insulin delivery, the terms "past", "present", and "future" as used herein may instead refer to a time as being before, simultaneous with, or after, respectively, a calculation data time. Moreover, predicted and anticipated quantities that are based on time intervals, for example predicted BGC-neutral amounts and average rates of PDIUE expenditure and anticipated amounts and average rates of PDIUE expenditure, are considered future quantities, if the time intervals on which they are based end in the future relative to the calculation data time.

The term "near future" as used herein means the time period beginning at the calculation data time and ending zero to seven hours after the calculation data time.

The term "recent past" as used herein means the time period beginning zero to five hours before the calculation data time and ending at the calculation data time.

The term "computer readable medium" as used herein refers to a digital medium which may be read by a computer, processor, microprocessor or other digital device. Examples of computer readable media include, but are not limited to, CDROM's, CDRW, Random Access Memory (RAM), including Dynamic Random Access Memory (DRAM) and Static Random Access Memory (SRAM), hard disks, such as contained in hard disk drives, floppy disks, digital memory sticks, Digital Video Disks (DVD), and magnetic tape.

The term "data store" or "digital memory" as used herein refers to a digital data storage medium capable of being read from and written to. The terms "data store" and "digital memory" are used interchangeably throughout the present application. A "data store" or "digital memory" may be used to store at least one BGC-related data item or one insulin delivery or PDIUE-related data item. A "data store" or "digital memory" may comprise a CDROM, CDRW, Random Access Memory (RAM), including Dynamic Random Access Memory (DRAM) and Static Random Access Memory (SRAM), hard disks, such as contained in hard disk drives, floppy disks, digital memory sticks, Digital Video Disks (DVD), and magnetic tape. Typically a "data store" is either RAM or a disk drive connected, via a wired or wireless connection, to system of the invention, blood glucose monitor, and/or insulin delivery system.

The term "numeric input" as used herein, as in the phrase "a device capable of accepting numeric input", means input in the form of numbers and also input that adjusts pre-existing numbers upward or downward, such as by pressing up arrow and down arrow keys.

The term "wireless communication" as used herein means electronic communcations that do not require a physical electrical connection between the devices in communication. As used herein, "wireless communication" may refer to wi-fi, wi-max, radio, cellular telephonic, infrared communications and the like.

The term "wired communication" as used herein refers to electronic communications that require a physical electrical connection between the devices in communication. As used herein, "wired communications" may refer to internet, USB, serial, parallel communication and the like.

As used herein a "system" or a "device" of the invention mean the same thing, and the terms are used interchangeably throughout the present application.

Rationale for and Advantages of the Invention

Embodiments of the present invention allow its users to easily know the amount of PDIUE expenditure, that is, the amount of bolus insulin that was, is, or will be "used" in the pharmacodynamic sense, over any time interval beginning up to five hours in the past and ending up to seven hours in the future. This knowledge is helpful because it is the PDIUE associated with a time interval, rather than the amount of insulin bolused during that time interval or even the amount of insulin bolused at any particular time, that is relevant to the behavior of BGC over the time interval. Estimating the amount of PDIUE associated with a time interval without the aid of an automated system, such as the present invention, is difficult for the average person to do, especially when more than one standard bolus or an extended bolus is involved.

By calculating and optionally displaying a past amount and/or rate of PDIUE expenditure, embodiments of the invention facilitate comparison of the past behavior of BGC over a time interval with the amount of insulin that was "used" in the pharmacodynamic sense over the same time interval. Embodiments of the invention may perform a comparison of a past amount and/or rate of PDIUE expenditure with BGC behavior and calculate and optionally display a past BGC-neutral amount and/or rate of PDIUE expenditure, that is, a hypothetical amount and/or rate of PDIUE expenditure which, according to calculation, would have resulted in no net change in BGC whether or not a change in BGC did occur. With experience, this comparison teaches a user about the magnitude and timing of his insulin need, expressed in PDIUE terms, under a variety of circumstances and thereby helps improve the user's insulin need prediction skills so that he may predict BGC-neutral amounts and/or rates of PDIUE expenditure. In addition, when this comparison indicates an apparently much greater insulin need than expected based upon past experience, it signals a possible insulin delivery problem.

By calculating and optionally displaying an anticipated amount and/or rate of PDIUE expenditure from insulin delivery, embodiments of the invention facilitate anticipation of the amount of insulin that will be "used" in the pharmacodynamic sense in the future. Comparison of an anticipated amount and/or rate of PDIUE expenditure from insulin delivery with a user predicted BGC-neutral amount and/or rate of PDIUE expenditure, respectively, aids the prediction of the behavior of BGC, and thereby helps a user to make adjustments to optimize BGC control. Toward this end, a desired amount of carbohydrate consumption and/or a desired insulin delivery scenario may be calculated.

The capability of a system of the invention to calculate and recommend an insulin delivery scenario to approximate a user-specified amount and/or rate of PDIUE expenditure enhances the user's ability to control BGC by facilitating his control of future amounts and/or rates of PDIUE from insulin delivery.

By allowing a user to know and communicate in terms of PDIUE both retrospectively and prospectively, and in real time, embodiments of the invention especially augment the user's ability to manage BGC by analysis and adjustment "on the fly" in situations about which the art offers the least reliable quantitative guidance, such as in the aftermath of a poorly understood or complex meal and/or during or after variations in physical activity, as well as when an insulin delivery problem occurs.

For example, typically, within the first two to three hours after a meal or physical activity variation, insulin need in terms of the rate of PDIUE may increase or decrease rapidly from what it was before the meal or physical activity variation. However, it is usually the case that over the ensuing several hours, the needed rate of PDIUE changes relatively slowly, ultimately returning to zero, the basal level. Consequently, once the needed rate of PDIUE enters the slowly changing phase, BGC can be managed by taking the steps of:
1. calculating a recent past rate of PDIUE expenditure;
2. using recent past or current BGC data and a recent past rate of PDIUE expenditure to calculate a recent past BGC-neutral rate of PDIUE expenditure;
3. using a recent past BGC-neutral rate of PDIUE expenditure to predict a near future BGC-neutral rate of PDIUE expenditure;
4. calculating an anticipated rate of PDIUE expenditure from insulin already infused and insulin programmed to be infused;
5. predicting near future BGC from recent past or current BGC data and a comparison of a predicted near future BGC-neutral rate of PDIUE expenditure with an anticipated rate of PDIUE expenditure from insulin already infused and insulin programmed to be infused; and
6. pursuing a desired BGC result by optionally adjusting insulin delivery programming, consuming carbohydrate, and/or taking other action in response to predicted near future BGC.

Embodiments of the present invention greatly facilitate, and thus, enables this new, quantitative approach to BGC management that is especially effective and valuable in precisely the situations about which the art offers the least reliable quantitative guidance, namely the aftermath of poorly understood or complex meals and physical activity variation. The value of this new approach is particularly great around bedtime because, as a result of the evening meal and insulin dosing for it, either significant a significant rate of PDIUE need above the basal level, or a significant rate of PDIUE from insulin already infused and programmed to be infused, or both, often continue beyond bedtime, when good BGC control is extremely important due to the difficulties inherent in monitoring and adjusting BGC during the sleeping hours.

Calculation of $$\int_{t1}^{t2} [d(PDIUE)/dt]dt$$

and d(PDIUE)/dt

A system of the invention requires insulin dosing information on which to base calculations. Insulin dosing information may be manually input into a system of the invention by art methods, a necessity for the capture of insulin dosing information related to insulin injection by syringe. A system of the invention may be integrated with an insulin delivery system, such as an insulin pump, and such integration may facilitate the transfer of insulin dosing information to the system of the invention.

PDIUE and IOB have been defined above in the context of a euglycemic glucose clamp study, and $$\int_{t1}^{t2} [d(PDIUE)/dt]dt$$

can be determined in such a study. However, in clinical practice, euglycemic glucose clamp studies are seldom performed; the vast majority of patients will never have one. Therefore, just as the practicality of art insulin delivery systems that display IOB required the availability of methods for calculating IOB without a euglycemic glucose clamp study in every patient, in order for the present invention to be practical, it is necessary to have available methods for calculating amounts and rates of PDIUE expenditure that do not require a euglycemic glucose clamp study in each patient.

One method by which a system of the invention may calculate amounts and rates of PDIUE expenditure, as functions of time, involves referring to a published insulin time-action profile graph that plots GIR versus time, preferably one derived from a euglycemic glucose clamp study in Type I diabetes patients taking the same or a similar type of insulin to the type taken by the patient employing the present invention. A basic assumption is that although the effect of PDIUE from an insulin bolus under the present invention will, as noted above, vary with the circumstance (decreasing BGC, disposing of glucose from food already eaten or not yet eaten, compensating for diminished insulin responsiveness, etc.), the PDIUE from an insulin bolus under the present invention should be allocated to intervals of time proportionally to the way PDIUE is allocated to intervals of time in an appropriate, published insulin time-action profile graph. Thus, it is not necessary to know what $I_i$ and $R_I$ were in the experiments that led to the published graph as long as $R_I$ was constant, as it typically is in a euglycemic glucose clamp study. Because a published graph plots GIR versus time, it provides both $$\int_{t1}^{t2} [GIR] dt \text{ and } \int_{t0}^{t\infty} [GIR] dt,$$

wherein t1 and t2 are the bounds of any time interval of interest, t0 is the time of insulin bolus infusion, and t∞ is a time at which the pharmacodynamic effect of that insulin is exhausted. By definition, $$\int_{t1}^{t2} [GIR] dt = \int_{t1}^{t2} [R_I \cdot d(PDIUE)/dt] dt,$$

and since $R_I$ is constant, PDIUE can be allocated to intervals of time proportionally to glucose uptake, measured as glucose infused:

$$\int_{t1}^{t2} [GIR] dt \div \int_{t0}^{t\infty} [GIR] dt =$$

$$\int_{t1}^{t2} [d(PDIUE)/dt] dt \div \int_{t0}^{t\infty} [d(PDIUE)/dt] dt.$$

This euglycemic glucose clamp study-based allocation of PDIUE to intervals of time is how PDIUE from an insulin bolus under the present invention may be proportionally allocated to intervals of time. For example, if the published graph shows $$\int_{t1}^{t2} [GIR] dt \div \int_{t0}^{t\infty} [GIR] dt$$

to be 35% from one to two hours after the insulin bolus, then, as a first approximation, independent of its size, a bolus under the present invention will have 35% of its PDIUE allocated to the time interval from one to two hours after infusion. Since this percentage is derived from the fraction of the area under the GIR curve during the time interval of interest as compared with the area under the entire GIR curve, this percentage is also referred to in this specification as the "interval area fraction". A system of the present invention can employ the corresponding interval area fraction from an insulin time-action profile graph to calculate $$\int_{t1}^{t2} [d(PDIUE)/dt] dt$$

due to an actual bolus of insulin that it delivers as follows:

$$\int_{t1}^{t2} [d(PDIUE)/dt] dt = I_i \times \int_{t1}^{t2} [GIR] dt \div \int_{t0}^{t\infty} [GIR] dt,$$

since by definition, $$\int_{t0}^{t\infty} [d(PDIUE)/dt] dt = I_i.$$

Here, $$\int_{t1}^{t2} [d(PDIUE)/dt] dt$$

is "the amount of insulin usage" in the pharmacodynamic sense over the time interval from t1 to t2, $I_i$ is the amount of insulin bolused by the patient's insulin delivery system, and $$\int_{t1}^{t2} [GIR] dt \div \int_{t0}^{t\infty} [GIR] dt$$

is the interval area fraction of the corresponding time interval relative to the time of insulin bolus under the GIR versus time curve of an appropriate, published insulin time-action profile graph. Careful examination of such published insulin time-action profile graphs may allow construction of look-up tables that may be stored in the memory of systems of the invention and which provide interval area fractions as output from the input of t1 relative to t0 and t2 relative to t0. Interval area fraction look-up tables may be constructed at any desired resolution, but preferably having t1 and t2 resolved to 15 minutes or less, so as not to introduce clinically significant rounding errors in PDIUE calculations. Some art insulin delivery system manufacturers calculate IOB from published insulin time-action profile graphs in a manner analogous to that described above for PDIUE calculation. As noted above, IOB can be considered to be a special case of $$\int_{t1}^{t2}[d(PDIUE)/dt]dt$$

in which t1 is the then present time of calculation, tc, relative to the time of insulin bolus infusion, and t2 is t∞, a time when the effect of all previously bolused insulin is exhausted, that is, $$IOB = \int_{tc}^{t\infty}[d(PDIUE)/dt]dt.$$

As such, IOB may be calculated from the equation, $$IOB = I_i \times \int_{tc}^{t\infty}[GIR]dt \div \int_{t0}^{t\infty}[GIR]dt,$$

wherein $I_i$ is the amount of insulin bolused by an art insulin delivery system, and $$\int_{tc}^{t\infty}[GIR]dt \div \int_{t0}^{t\infty}[GIR]dt$$

is the interval area fraction of the corresponding time interval taken from a published insulin time-action profile graph. The interval area fraction that can be used to calculate IOB is always based on an interval starting with tc and ending with t∞. Any interval area fraction that ends with t∞ is referred to in this specification as a "terminal interval area fraction". In the context of IOB discussion, terminal interval area fractions are published by some art insulin delivery system manufacturers and appear in reference books as tables and graphs of terminal interval area fraction as a function of time after insulin bolus (tc-t0). These tables and graphs are typically labeled misleadingly as "% insulin remaining". The label "% PDIUE remaining" would be more accurate. As discussed further below, there are additional methods that may be used to calculate the more general case of $$\int_{t1}^{t2}[d(PDIUE)/dt]dt,$$

and one of these methods takes advantage of the aforementioned published tables and graphs of terminal interval area fraction that are labeled "% insulin remaining".

Interval area fractions employed in systems of the invention may be calculated as the difference of two terminal interval area fractions. That is, the terminal interval area fraction may be found from t1 until t∞, and the terminal interval area fraction may be found from t2 until t∞, and the latter may be subtracted from the former to calculate the interval area fraction between t1 and t2. Thus, to calculate interval area fractions using a look-up table, a system of the invention need not contain a look-up table of all combinations of t1 and t2. It needs only to contain a look-up table of terminal interval area fractions, to select two values from that table corresponding to different times that may be in the past, present, or future relative to the calculation data time or the clock time at which the calculation is performed, and to find the difference between the two selected values.

It should be apparent that the calculation of $$\int_{t1}^{t2}[d(PDIUE)/dt]dt$$

may be accomplished either by multiplying $I_i$ by the interval area fraction between t1 and t2, which may be found as the difference of the terminal interval area fractions at t1 and t2, or alternatively by subtracting the product of $I_i$ multiplied by the terminal interval area fraction at t2 from the product of $I_i$ multiplied by the terminal interval area fraction at t1. These two methods are mathematically equivalent, and the latter can be thought of as subtracting what would be IOB at t2 from what would be IOB at t1 if the definition of IOB were expanded to encompass PDIUE starting from any time, rather than only the then present time of calculation, until such time as the effect of bolus insulin is exhausted.

As described above, the calculation of $$\int_{t1}^{t2}[d(PDIUE)/dt]dt$$

after an insulin bolus can be accomplished using $I_i$, t1, t2, and an appropriate, published insulin time-action profile graph. This calculation requires finding the interval area fraction under the curve between t1 and t2, that is, the integral of GIR from t1 to t2 divided by the integral of GIR from t0 until t∞. Since insulin time-action profile graphs may be modeled as mathematical functions relating GIR to time, the interval area fraction between t1 and t2 may also be found by employing the known tools of integral calculus. Those skilled in the arts of engineering and mathematics are capable of fitting an insulin time-action profile graph to a mathematical function, hereafter referred to as an insulin time-action profile function, using, for example, a non-linear least squares fit. Many possible mathematical functions known in the art may provide adequate models for an insulin time-action profile graph. The following is an example of a mathematical form that GIR (expressed in grams of glucose per hour) as a function of time (t, expressed in hours) may take:

$$GIR = k(t\char`\^ a)(b\char`\^[-ct])$$

In this example, the symbol "^" indicates the raising of the term to its left to the exponential power of the term to its right. That is, the term "t" is raised to the power of "a", and the term "b" is raised to the power of "−ct". The terms "k", "a", "b", and "c" are constants to be determined by fitting an insulin time-action profile graph to this example mathematical function. The terms "a", "b", and "c" are positive, real numbers that need not be whole or rational. The terms "a" and "b" are dimensionless and greater than 1. The term "c" has the dimensions of reciprocal time. For example, "a"=1.9, "b"=the natural base epsilon, and "c"=3 h$^{-1}$. The term "k" is a positive, real number having the dimensions of grams of glucose per ([time]^[1+a]). For example, if "a"=1.9, "k" may be 50 grams of glucose per hour$^{2.9}$.

Although, except in the special case IOB, the art does not describe the communication of $$\int_{t1}^{t2}[d(PDIUE)/dt]dt$$

to the user of an insulin delivery system or BGC predicting system, some concepts and methods that are helpful for understanding ways of calculating $$\int_{t1}^{t2}[d(PDIUE)/dt]dt$$

more generally are disclosed in the art (U.S. Pat. No. 6,925, 393, U.S. Pat. No. 5,822,715, US 2006/137695, U.S. Pat. No. 6,835,175).

As described above, the calculation of $$\int_{t1}^{t2}[d(PDIUE)/dt]dt$$

can be accomplished using $I_t$, t1, t2, and an appropriate insulin time-action profile graph or function. Implicit in the description above is the assumption that the insulin bolus is infused essentially all at once so that t1 and t2 are discreet points in time after insulin infusion at t0. This assumption is valid when a single standard bolus is infused because a standard bolus entails infusion of insulin over less than five minutes, and insulin time-action profile graphs and functions are generally derived from euglycemic glucose clamp studies in which the insulin is infused essentially all at once. However, it is also possible to calculate $$\int_{t1}^{t2}[d(PDIUE)/dt]dt$$

after multiple standard boluses, after extended or other types of bolus that can be mathematically described, and after combinations of any of these types of bolus.

The calculation of $$\int_{t1}^{t2}[d(PDIUE)/dt]dt$$

after multiple standard boluses may be made, as a first approximation, by summing the $$\int_{t1}^{t2}[d(PDIUE)/dt]dt$$

contributed by each of the individual standard boluses. When a bolus for which $$\int_{t1}^{t2}[d(PDIUE)/dt]dt$$

is to be calculated is of the extended type or of any other type that involves infusion of insulin over a period of time ranging up to several hours, the calculation of $$\int_{t1}^{t2}[d(PDIUE)/dt]dt$$

may be accomplished, for example, with an approximation in which the bolus is treated as a series of shorter duration bolus segments. Each segment is then treated as a separate standard bolus with the insulin infused over that segment treated as though it were infused at the time midpoint of the segment. The segments may be of any duration, the same or different from one another, but preferably no more than one hour long. The $$\int_{t1}^{t2}[d(PDIUE)/dt]dt$$

contributed by each of the segments are then calculated separately and summed. If the duration of the extended bolus, or other type of bolus that involves infusion of insulin over a period of time, is short enough, preferably no more than one hour, then the bolus may not need to be divided into segments, and the insulin infused may simply be treated as though it were infused at the time midpoint of the bolus. The calculation of $$\int_{t1}^{t2}[d(PDIUE)/dt]dt$$

after multiple boluses of different types, for example a standard bolus and an extended bolus, may be made by summing the $$\int_{t1}^{t2}[d(PDIUE)/dt]dt$$

contributed by each different bolus. As an alternative method of calculation, mathematical functions that describe the time dependence of insulin infusion and an insulin time-action profile function, together with known mathematical techniques, may be used to find $$\int_{t1}^{t2}[d(PDIUE)/dt]dt,$$

as well as instantaneous values of d(PDIUE)/dt as a function of time.

As noted above, insulin time-action profile graphs and "% insulin remaining" information that is available from the published literature may be employed to calculate $$\int_{t1}^{t2}[d(PDIUE)/dt]dt.$$

Such literature information may not be optimal for a particular patient. Patient-optimized information about insulin pharmacodynamics may be generated by personal experimentation using known methods (M. K. Frohnauer, et al., Diabetes Technology & Therapeutics 2001, 3, 419-429). For example, after a basal state is established, a bolus of insulin is taken by a patient from his insulin delivery system, and BGC is then closely tracked over time. Optionally, the patient may use the Gerritzen method, which allows periodic consumption of oral glucose or carbohydrate to avoid having to start the experiment at a very high BGC level in order to avoid risking hypoglycemia. Utilizing a sliding blood glucose correction scale, and if oral glucose is taken, making assumptions about the rate at which oral glucose appears in the blood and assuming an insulin-to-carbohydrate ratio, an approximate, personal insulin time-action profile function or "% insulin remaining" function can be generated. Other art methods for generating a personal insulin time-action profile function or a "% insulin remaining" function that are recommended by insulin delivery system manufacturers in the context of IOB duration adjustment may also be used.

As noted above, according to the art, insulin delivery systems may allow a user to adjust the duration of bolus insulin effect employed in calculations of IOB. Likewise, a system of the invention may allow a user to adjust the duration of bolus insulin effect employed in calculations of $$\int_{t1}^{t2}[d(PDIUE)/dt]dt.$$

For example, a system of the invention may allow the user to adjust, based on personal experience or experimentation and/or healthcare professional advice, an internal reference insulin time-action profile function. Such adjustment may be made, for example, by proportionally or non-proportionally expanding or contracting the time-action profile function along the time axis. For the purpose of calculating $$\int_{t1}^{t2}[d(PDIUE)/dt]dt,$$

a system of the invention may also adjust, by expansion or contraction along the time axis, an internal reference "% insulin remaining" function or look-up table.

There is evidence that the duration of the time-action profile of insulin may depend on the dose of insulin. That is, the area under the GIR versus time curve may be proportional to the insulin dose, but a larger fraction of that area may appear at longer times after dosing when a larger dose is given. A system of the invention may take this into account by calculating $$\int_{t1}^{t2}[d(PDIUE)/dt]dt$$

from one or more of a series of two or more reference insulin time-action profile functions or internal reference "% insulin remaining" functions or look-up tables that differ in their durations. For example, the choice of which reference function to use in the calculation may be made by the system based on how much $$\int_{tc}^{t\infty}[d(PDIUE)/dt]dt$$

from insulin already infused exists at the calculation data time. The more $$\int_{tc}^{t\infty}[d(PDIUE)/dt]dt$$

from insulin already infused, the longer the duration of the reference function chosen. For example, if when calculated using the reference insulin time-action profile function of shortest duration $$\int_{tc}^{t\infty}[d(PDIUE)/dt]dt$$

is less than or equal to 3.0 U, then the reference insulin time-action profile function of shortest duration is used in calculations of $$\int_{t1}^{t2}[d(PDIUE)/dt]dt.$$

However, if when calculated using the reference insulin time-action profile function of shortest duration $$\int_{tc}^{t\infty}[d(PDIUE)/dt]dt$$

exceeds 3.0 U, then the duration of the reference insulin time-action profile function used in calculations of $$\int_{t1}^{t2}[d(PDIUE)/dt]dt$$

is increased by 10% for each doubling of the calculated $$\int_{t1}^{t2} [d(PDIUE)/dt]dt.$$

As another example, to calculate $$\int_{t1}^{t2} [d(PDIUE)/dt]dt,$$

the system may apply different reference insulin time-action profile functions or internal reference "% insulin remaining" functions or look-up tables to different boluses depending on the amounts and ages of the boluses considered at the calculation data time. For example, the system applies the "% insulin remaining" look-up table of shortest duration to the first 5.0 U of boluses that are less than three hours old, but it applies a "% insulin remaining" look-up table of longer duration to boluses, less than three hours old, beyond the first 5.0 U. Furthermore, if boluses less than three hours old total more than 5.0 U, then the system applies the "% insulin remaining" look-up table of longer duration to any boluses more than three hours old; otherwise, the system applies the "% insulin remaining" look-up table of shortest duration to boluses more than three hours old. Additionally, if a bolus less than three hours old crosses the 5.0 U threshold, then for the purpose of calculation, the system may apply the "% insulin remaining" look-up table of shortest duration to the portion of it below the threshold and the "% insulin remaining" look-up table of longer duration to the rest of it. As another example, to calculate $$\int_{t1}^{t2} [d(PDIUE)/dt]dt,$$

the system may utilize calculation methods that start from the first bolus that may have current impact and take into account the impact of each bolus on the duration of effect of every subsequent bolus, as reflected in the choice of reference insulin time-action profile function or internal reference "% insulin remaining" function or look-up table. For example, starting from the last bolus made after a period of at least six hours without any boluses (this is the first bolus considered in this calculation), the system employs a "% insulin remaining" look-up table that depends on the size of the first bolus to calculate the amount of PDIUE remaining from it at the time of the second bolus, and that amount of PDIUE remaining from it is added to the second bolus for the purposes of choosing which "% insulin remaining" look-up table to use to determine the amount of PDIUE remaining from the first two boluses at the time of the third bolus, and so on. As another example, to calculate $$\int_{t1}^{t2} [d(PDIUE)/dt]dt,$$

the system may simply base the choice of which reference insulin time-action profile function or internal reference "% insulin remaining" function or look-up table to apply to each bolus on the size of that bolus, independent of its time and relationship to other boluses. For example, the system applies a "% insulin remaining" look-up table of shortest duration to boluses up to 5.0 U, applies one of 15% longer duration to boluses from 5.1 U to 8.0 U, and applies one that is another 15% longer in duration to boluses above 8.0 U. When considering bolus segments that are derived from the division of extended boluses for ease of calculation as described above, the system applies the look-up table appropriate to the size of the entire extended bolus.

In addition to calculating $$\int_{t1}^{t2} [d(PDIUE)/dt]dt,$$

a system of the invention may calculate one or more average d(PDIUE)/dt values over any time interval or intervals of interest or one or more instantaneous d(PDIUE)/dt values at any time or times of interest; that is, a system of the invention may calculate any PDIUE-related quantity as a function of time. An average d(PDIUE)/dt value may be calculated by dividing $$\int_{t1}^{t2} [d(PDIUE)/dt]dt$$

by the length of the time interval t2-t1. The time interval over which an average d(PDIUE)/dt is calculated, may be as short as the time interval between the data points required for the calculation. An instantaneous d(PDIUE)/dt value may be calculated by applying known mathematical techniques to mathematical functions that describe the time dependence of insulin infusion and an appropriate insulin time-action profile function. As used herein, the term "d(PDIUE)/dt" encompasses both instantaneous and average d(PDIUE)/dt. The quantity d(PDIUE)/dt is expressed in the dimensions of units per minute or units per hour. Conversely, a system of the invention, by applying known mathematical techniques, may calculate $$\int_{t1}^{t2} [d(PDIUE)/dt]dt$$

from d(PDIUE)/dt during the time interval from t1 to t2 or from a mathematical function of d(PDIUE)/dt of time over the time interval from t1 to t2. The inherent interrelatedness of $$\int_{t1}^{t2} [d(PDIUE)/dt]dt$$

and d(PDIUE)/dt during a time interval from t1 to t2 will be appreciated by anyone skilled in the art of mathematics and is implicit in all discussion of PDIUE-related quantities, functions, and variables in this specification. While some discussion herein of $$\int_{t1}^{t2} [d(PDIUE)/dt]dt$$

will not explicitly mention d(PDIUE)/dt during the time interval from t1 to t2, and some discussion herein of d(PDIUE)/dt during the time interval from t1 to t2 will not explicitly mention $$\int_{t1}^{t2} [d(PDIUE)/dt]dt,$$

it should be understood that each mathematically implies the other.
Display of $$\int_{t1}^{t2} [d(PDIUE)/dt]dt$$

and d(PDIUE)/dt from Insulin Delivery

A system of the invention may display past, present, or future amounts or rates of PDIUE expenditure based on either insulin already infused, insulin already infused plus insulin programmed to be infused, or insulin already infused plus insulin programmed to be infused, as tentatively adjusted. In either case, amounts or rates of PDIUE expenditure are calculated as described above. The display may have the form of a graph (line, bar, or other standard type), a data table, and/or a response to a query. For example, a graph of rates of PDIUE expenditure versus time may be displayed. A graph of rates of PDIUE expenditure versus time may be displayed along with a graph of insulin infusion versus time in order to assist the user in understanding the relationship between the two. Rates of PDIUE expenditure may also be displayed as values at specific time intervals, for example in the form of a table showing rates of PDIUE expenditure at 30 minute clock time intervals (9:00 PM, 9:30 PM, etc.) and/or at 15 minute intervals starting with the present time and/or at time intervals bound by time points for which BGC data are available. A rate of PDIUE expenditure may also be displayed in response to a query about the rate of PDIUE expenditure at a specific point in time or as an average over a specific time interval starting and ending at times that are input by a user. Likewise, amounts of PDIUE expenditure may be displayed in the form of a table showing amounts of PDIUE expenditure over clock time intervals and/or time intervals starting with the present time and/or time intervals bound by time points for which BGC data are available. Furthermore, an amount of PDIUE expenditure may be displayed in response to a query about its value over a specific time interval starting and ending at times that are input by the user.

Calculation of Past BGC-Neutral d(PDIUE)/dt and Past BGC-Neutral $$\int_{t1}^{t2} [d(PDIUE)/dt]dt$$

Embodiments of the present invention allows for the retrospective calculation of a BGC-neutral rate of PDIUE expenditure and the availability to a user of BGC-neutral rate of PDIUE expenditure data corresponding to a past time point or time interval. A BGC-neutral rate of PDIUE expenditure is the rate of PDIUE expenditure from bolus insulin dosing that is required to maintain a steady BGC under non-basal conditions. By making certain assumptions as detailed below, a BGC-neutral rate of PDIUE expenditure can be calculated from insulin dosing information and BGC data, regardless of whether BGC remains steady in the normal or target range, remains steady outside of the normal or target range, or either rises or declines either with or without one or both of the starting and ending BGC values being in the normal or target range. These calculations may be performed by a system of the invention that receives BGC data generated by either a continuous glucose monitor or a conventional, point-in-time/ad hoc glucometer. The system of the invention may be integrated with a point-in-time glucometer or a continuous glucose monitor to facilitate the transfer of BGC data, the transfer otherwise being accomplished by manual input using art methods. Because a continuous glucose monitor, and a conventional, point-in-time glucometer measuring glucose in a blood sample from certain parts of the body (alternate site testing), are believed to provide BGC data that lags real/relevant time by up to about 30 minutes, a system of the invention may optionally correct for a time lag by applying a time offset to BGC data before correlating it to times associated with PDIUE. Such a time offset may be adjustable by the user based on personal experience and/or the advice of a healthcare professional as appropriate for the mode of BGC testing used at the time.

The time interval over which a BGC-neutral rate of PDIUE expenditure is calculated may be as short as the interval between the data points required for the calculation. The BGC-neutral rate of PDIUE expenditure corresponding to a specific time point may be considered to be the same as the average BGC-neutral rate of PDIUE expenditure over a time interval that contains that specific time point. The method of calculating a BGC-neutral rate of PDIUE expenditure and a BGC-neutral amount of PDIUE expenditure described below is exemplary and is not meant to be limiting.

In cases in which BGC remains steady over the time interval for which a BGC-neutral rate of PDIUE expenditure is being determined, the BGC-neutral rate of PDIUE expenditure equals the actual rate of PDIUE expenditure from insulin delivery, which can be calculated as described above. It is assumed, as a first approximation, that BGC itself does not greatly influence a BGC-neutral rate of PDIUE expenditure. This assumption is likely to be true for BGC levels that are not very far from the normal or target range, for instance between 50 mg/dL and 300 mg/dL.

In cases in which BGC rises over the time interval for which BGC-neutral d(PDIUE)/dt is being determined, BGC-neutral d(PDIUE)/dt equals the actual d(PDIUE)/dt from insulin delivery plus a d(PDIUE)/dt deficit, which may be calculated. The d(PDIUE)/dt deficit is calculated by first finding the net rise in BGC over the time interval of interest, t1 to t2. If BGC1 is the BGC value at the start of the time interval, that is, at t1, and BGC2 is the BGC value at the end of the time interval, that is, at t2, then the net rise is BGC2-BGC1. Next, by analogy to the high blood glucose correction bolus concept, a $$\int_{t1}^{t2} [d(PDIUE)/dt]dt$$

deficit is assumed to be equal to the amount of insulin that, if allowed sufficient time to exert its full effect under basal conditions, would hypothetically decrease BGC by the amount of the rise from BGC1 to BGC2.

$$\int_{t1}^{t2} [d(PDIUE)/dt]dt \text{ deficit} = (BGC2 - BGC1) \div R_{BCG/I}$$

$R_{BGC/I}$ (in milligrams of glucose per deciliter of blood per unit of insulin) reflects the responsiveness of a patient's BGC to insulin, and it is a parameter that must be programmed into the system of the invention. $R_{BGC/I}$ may be a function, including a continuously varying function, of time of day or other factors.

Next, the $$\int_{t1}^{t2} [d(PDIUE)/dt]dt$$

deficit is divided by the length of the time interval, t2-t1, to calculate the d(PDIUE)/dt deficit. Finally, the d(PDIUE)/dt deficit is added to the actual d(PDIUE)/dt from insulin delivery to calculate the BGC-neutral d(PDIUE)/dt.

Conversely, in cases in which BGC declines over the time interval for which BGC-neutral d(PDIUE)/dt is being determined, BGC-neutral d(PDIUE)/dt equals the actual d(PDIUE)/dt from insulin delivery minus a d(PDIUE)/dt excess, which may be calculated. The d(PDIUE)/dt excess is calculated by first finding the net decline in BGC, BGC1-BGC2, over the time interval of interest, t1 to t2. Next, a $$\int_{t1}^{t2} [d(PDIUE)/dt]dt$$

excess is assumed to be equal to the amount of insulin that, if allowed sufficient time to exert its full effect under basal conditions, would hypothetically decrease BGC by the amount of the decline from BGC1 to BGC2. Next, the $$\int_{t1}^{t2} [d(PDIUE)/dt]dt$$

excess is divided by the length of the time interval, t2-t1, to calculate the d(PDIUE)/dt excess. Finally, the d(PDIUE)/dt excess is subtracted from the actual d(PDIUE)/dt from insulin delivery to calculate the BGC-neutral d(PDIUE)/dt.

A BGC-neutral $$\int_{t1}^{t2} [d(PDIUE)/dt]dt$$

may be calculated by adding any $$\int_{t1}^{t2} [d(PDIUE)/dt]dt$$

deficit to, or subtracting any $$\int_{t1}^{t2} [d(PDIUE)/dt]dt$$

excess from, the $$\int_{t1}^{t2} [d(PDIUE)/dt]dt$$

from insulin delivery.

Display of Past BGC-Neutral d(PDIUE)/dt and Past BGC-Neutral $$\int_{t1}^{t2} [d(PDIUE)/dt]dt$$

A system of the invention may display a past BGC-neutral rate of PDIUE expenditure that has been calculated retrospectively as described above. The display may have the form of a graph (line, bar, or other standard type), a data table, and/or a response to a query. For example, a graph of past BGC-neutral rates of PDIUE expenditure versus time may be displayed. A graph of past BGC-neutral rates of PDIUE expenditure versus time may be displayed along with a graph of actual past rates of PDIUE expenditure from insulin delivery versus time and/or with BGC data in order to assist the user in understanding the relationship between them. Past BGC-neutral rates of PDIUE expenditure may also be displayed as values at specific time intervals, for example in the form of a table showing past BGC-neutral rates of PDIUE expenditure at 30 minute clock time intervals and/or at 15 minute intervals starting with the present time and/or at time intervals bound by time points for which BGC data are available. A past BGC-neutral rate of PDIUE expenditure may also be displayed in response to a query about the past BGC-neutral rate of PDIUE expenditure at a specific point in time or as an average over a specific time interval starting and ending at times that are input by the user. Likewise, past BGC-neutral amounts of PDIUE expenditure may be displayed in the form of a table showing past BGC-neutral amounts of PDIUE expenditure over clock time intervals and/or time intervals starting with the present time and/or time intervals bound by time points for which BGC data are available. Furthermore, a past BGC-neutral amount of PDIUE expenditure may be displayed in response to a query about its value over a specific time interval starting and ending at times that are input by the user.

Prediction of BGC-Neutral d(PDIUE)/dt and BGC-Neutral $$\int_{t1}^{t2} [d(PDIUE)/dt]dt$$

Except for the first two to three hours after a meal or physical activity variation, the BGC-neutral rate of PDIUE expenditure typically changes relatively slowly, ultimately returning to zero, the basal level, if no further perturbations occur. Consequently, once the BGC-neutral rate of PDIUE expenditure enters the slowly changing phase, with experience and knowledge of an immediate past BGC-neutral rate of PDIUE expenditure, a user of a system of the invention may predict the evolution of the BGC-neutral rate of PDIUE expenditure over the ensuing several hours, especially over the next hour or two.

For example, if BGC-neutral rate of PDIUE expenditure calculations at, for example, 0.5 h intervals beginning with the start of a meal show that a patient with a basal insulin infusion rate of 0.5 U/h experiences a rise in the BGC-neutral rate of PDIUE expenditure from zero (the basal state) to a maximum of 2.0 U/h over the time interval from 2.0 to 2.5 h, and then over the time interval from 2.5 to 3.0 h, the BGC-neutral rate of PDIUE expenditure is 1.7 U/h, then without necessarily knowing much about the composition of the meal, the user may be able to predict that from 3.0 to 4.0 h after the beginning of the meal, the BGC-neutral rate of PDIUE expenditure will fall, possibly within the range of 1.2 to 1.6 U/h. If in reality, the BGC-neutral rate of PDIUE expenditure from 3.0 to 4.0 h proves to be 1.5 U/h, the user may then be able to predict that from 4.0 to 5.0 h, the BGC-neutral rate of PDIUE expenditure will fall further, possibly within the range of 0.9 to 1.3 U/h. If in reality, the BGC-neutral rate of PDIUE expenditure from 4.0 to 5.0 h proves to be 0.9 U/h, the user may then be able to predict that from 5.0 to 6.0 h, the BGC-neutral rate of PDIUE expenditure will fall further, possibly within the range of 0.4 to 0.7 U/h. If instead, the BGC-neutral rate of PDIUE expenditure from 4.0 to 5.0 h proves to be 1.3 U/h, the user may then be able to predict that from 5.0 to 6.0 h, the BGC-neutral rate of PDIUE expenditure will fall further, but not as much further, possibly within the range of 0.7 to 1.1 U/h. This process can be continued until the BGC-neutral rate of PDIUE expenditure falls close enough to zero that the uncertainty in the BGC-neutral amount of PDIUE expenditure from the time of the last prediction until the BGC-neutral rate of PDIUE expenditure returns to zero is not clinically significant, for example less than 0.5 U.

In the above example, the user makes predictions at one hour intervals in which he predicts only one hour ahead. His predictions are about one hour average BGC-neutral rates of PDIUE expenditure, and he makes his predictions in response to past one hour average BGC-neutral rate of PDIUE expenditure data that take BGC data into consideration. A user of a system of the invention may make just one prediction or more than one prediction over the course of several hours, as desired, in response to past BGC-neutral rate of PDIUE expenditure data. He may predict a BGC-neutral rate of PDIUE expenditure as a one hour average or as an average over a shorter or longer time interval. He may at any time predict a single BGC-neutral rate of PDIUE expenditure or a series of rates that he expects as the BGC-neutral rate of PDIUE expenditure evolves over time. He may predict the BGC-neutral rate of PDIUE expenditure as a continuous function of time. He may predict that the BGC-neutral rate of PDIUE expenditure will rise and/or remain constant and/or fall over time. For example, he may predict that the BGC-neutral rate of PDIUE expenditure will decline linearly from 2.0 U/h to zero over 5 h. As another example, he may predict that the BGC-neutral rate of PDIUE expenditure will remain constant at 3.5 U/h for 2 h and then fall linearly to zero over 7 h. As another example, he may predict that the BGC-neutral rate of PDIUE expenditure will linearly rise from zero to a maximum of 3.0 U/h after 3 h and then fall linearly to zero over 6 h. He may predict changes in the BGC-neutral rate of PDIUE expenditure that are not linear over time, for example that a function of the BGC-neutral rate of PDIUE expenditure over time may have segments of varying slope. A BGC-neutral rate of PDIUE expenditure may be predicted taking into account additional future circumstances, such as an anticipated meal (including carbohydrate consumption for the purpose of avoiding hypoglycemia) or an anticipated variation in physical activity, which a user of a system of the invention may quantify. A BGC-neutral rate of PDIUE expenditure may be predicted taking into account additional past circumstances, as well. For example, an immediate past BGC-neutral rate of PDIUE expenditure upon which a prediction of BGC-neutral rate of PDIUE expenditure is based may include the effect of rapid-acting carbohydrate consumption for the purpose of avoiding hypoglycemia. In this instance, a user may discount the immediate past BGC-neutral rate of PDIUE expenditure for the effect of the carbohydrate consumption before extrapolating from it a prediction of BGC-neutral rate of PDIUE expenditure. It should be apparent that the user's prediction may just as easily be expressed as one or more BGC-neutral amounts of PDIUE expenditure.

Another way in which a BGC-neutral amount and/or rate of PDIUE expenditure may be predicted is that a user may establish an algorithm governing how to predict a near future BGC-neutral amount and/or rate of PDIUE expenditure based on a recent past BGC-neutral amount and/or rate of PDIUE expenditure and, optionally after a user prompt, the system executes the algorithm, suggests a BGC-neutral amount and/or rate of PDIUE expenditure, and through either action or inaction, the user exercises an option to adopt or not adopt the system's suggested BGC-neutral amount and/or rate of PDIUE expenditure. For example, after receiving a command from a user, a system of the invention may calculate an average BGC-neutral rate of PDIUE expenditure over the previous one hour and suggest that the BGC-neutral amount of PDIUE expenditure over the next one hour will be 0.5 h times that rate and that the total BGC-neutral amount of PDIUE expenditure over the ensuing three hours will also be 0.5 h times that rate. The user may then either adopt or decline to adopt this suggestion, for example, by pressing a yes button or a no button, and if adopted, the suggested BGC-neutral amounts of PDIUE expenditure are considered as predicted BGC-neutral amounts of PDIUE expenditure and are figured into the system's calculations that predict BGC as if the predicted BGC-neutral amounts of PDIUE expenditure have been entirely conceived by the user himself. A particularly useful algorithm governing how to predict a near future BGC-neutral amount and/or rate of PDIUE expenditure based on a recent past BGC-neutral amount and/or rate of PDIUE expenditure is a fastest possible decay algorithm. A fastest possible decay algorithm predicts, based on user experience and/or healthcare provider recommendation, a smallest possible near future BGC-neutral amount and/or rate of PDIUE expenditure from a recent past BGC-neutral amount and/or rate of PDIUE expenditure. For example, if over the previous one hour, the average BGC-neutral rate of PDIUE expenditure is X, a fastest possible decay algorithm might suggest that minimally, the average BGC-neutral rates of PDIUE expenditure over the next three hours will be, respectively, 0.50×, 0.25×, and 0.10×. As another example, if over the previous one half hour, the average BGC-neutral rate of PDIUE expenditure is Y, a fastest possible decay algorithm might suggest that minimally, the average BGC-neutral rates of PDIUE expenditure over the next two hours will be, respectively, 0.8Y and 0.3Y. The purpose of a fastest possible decay algorithm is to account for the fact that the effect on BGC of most foods is exerted over several hours at an intensity that varies over time, but not abruptly, and the fact that once past the peak of its intensity, the effect on BGC of most foods declines in such a manner that it is possible to predict a minimal effect in the near future from knowledge of the actual effect in the recent past. A fastest possible decay algorithm reflects these facts in a predicted BGC-neutral amount and/or rate of PDIUE expenditure. The use of a fastest possible decay algorithm helps a user manage BGC closer to target by promoting the infusion of more needed insulin than might be called for by art methods, which would often call for what would amount to a zero near future BGC-neutral amount and/or rate of PDIUE expenditure. The fact that a fastest possible decay algorithm has predicted BGC-neutral amounts and/or rates of PDIUE expenditure that decay as fast as possible in light of realistic food effects biases the algorithm to err on the side of avoiding excessive insulin dosing and hypoglycemia. Nevertheless, in order to account for the possibility that consumption of very rapidly acting carbohydrate in the recent past might skew the relationship between recent past and near future BGC-neutral amounts and/or rates of PDIUE expenditure, a system of the invention may allow a user to diminish a recent past BGC-neutral amount and/or rate of PDIUE expenditure before inputting that amount or rate into an algorithm, for example a fastest possible decay algorithm. For example, a user may diminish, before inputting into a fastest possible decay algorithm, a previous one hour BGC-neutral amount of PDIUE expenditure by 1.0 U if one hour ago the patient has eaten 8 grams of glucose to avoid hypoglycemia and the patient typically doses 1.0 U per gram of carbohydrate. A user may also augment the output of an algorithm, that is, a system suggested future BGC-neutral amount and/or rate of PDIUE expenditure, before adoption by the user in order to account for future circumstances, such as an anticipated meal. A user may establish just one algorithm or more than one algorithm, each stored in the system and labeled according to the circumstance in which it is designed to be employed. For example, a user may establish one fastest possible decay algorithm labeled by him or its source as "after two slices of pizza" and another labeled by him or its source as "after chicken and rice". In order to establish an algorithm, a user may, for example, select it from a set of such algorithms that have been preloaded into a system of the invention by a manufacturer. Algorithms may also be user defined, for example, by coding in a format such as "rate,minutes: −40,0=100%; 0,30=80%; 30,60=50%; 60,90=30%; 90,120=10%" or such as "amount,hours: −1,0=100%; 0,1=50%; 1,2=35%; 2,3=15%". The former code means that relative to the average BGC-neutral rate of PDIUE expenditure over the last 40 minutes, the average rate will be 80% over the time interval from 0 to 30 minutes in the future, 50% over the time interval from 30 to 60 minutes in the future, 30% over the time interval from 60 to 90 minutes in the future, and 10% over the time interval from 90 to 120 minutes in the future. The latter code means that relative to the BGC-neutral amount of PDIUE expenditure over the last 1 hour, the amount will be 50% over the time interval from 0 to 1 hour in the future, 35% over the time interval from 1 to 2 hours in the future, and 15% over the time interval from 2 to 3 hours in the future. Such coding may also serve as a labeling format. Algorithms may be defined with any number of future time intervals, including just one, for example "amount,hours: −1,0=100%; 0,4=100%", which means that relative to the BGC-neutral amount of PDIUE expenditure over the last 1 hour, the amount will be 100% over the next 4 hours.

Input and Display of Predicted BGC-Neutral d(PDIUE)/dt and Predicted BGC-Neutral $$\int_{t1}^{t2} [d(PDIUE)/dt] dt$$

A system of the invention may accept a prediction of a BGC-neutral rate of PDIUE expenditure from a user in order to display it for visual inspection, in order to compare it with an actual BGC-neutral rate of PDIUE expenditure as it evolves, and in order to compare it with an anticipated rate of PDIUE expenditure from insulin delivery. Anticipated rates of PDIUE expenditure from insulin delivery may be calculated taking into account either insulin already infused alone, insulin already infused plus insulin programmed to be infused, or insulin already infused plus insulin programmed to be infused, as tentatively adjusted. The comparison of predicted BGC-neutral rates of PDIUE expenditure with anticipated rates of PDIUE expenditure from insulin delivery provides a basis for a prediction of the evolution of BGC.

A system of the invention may accept a prediction of a BGC-neutral rate of PDIUE expenditure from a user by any standard method of data input that allows the specification of at least one BGC-neutral rate of PDIUE expenditure and the time at which it is predicted to occur. The prediction may, for example, be made in the form of a table showing predicted BGC-neutral rates of PDIUE expenditure at 30 minute clock time intervals and/or at 15 minute intervals starting with the present time. Such a prediction may be input, for example, by typing, using up/down and optionally left/right arrows with an enter button function, operating a touch screen menu, or operating a mouse or touch pad or trackball.

As another possibility, a graph of the BGC-neutral rate of PDIUE expenditure as a function of time may be input. A graphical prediction may be made in the form of point coordinates that are input, for example, by typing, using up/down and optionally left/right arrows with an enter button function, operating a touch screen menu, or operating a mouse or touch pad or trackball, or by spotting points on a display screen with a stylus, fingernail, mouse, touchpad or trackball, optionally followed by employing a line smoothing/curve fitting algorithm.

Alternatively, the prediction may be made in the form of lines drawn on a display screen of the system with a stylus or fingernail if the system is equipped with a type of display screen that may be drawn upon, for example, similar to that of a PDA device in notepad mode. In the absence of this type of display screen, or for instance if a standard personal computer is functioning as the system's user interface, a mouse or touch pad or trackball may be used to input the prediction. The display screen may have a graphing grid background against which to draw. Button presses, a touch screen menu, or operation of a mouse or touch pad or trackball may allow a user to begin drawing, indicate completion of drawing, and accept or reject the input. Alternatively, a user may select a graph of the BGC-neutral rate of PDIUE expenditure as a function of time from a set offered by the system, or select an approximation of a desired BGC-neutral rate of PDIUE expenditure function from a set offered by the system and then modify it. BGC-neutral rate of PDIUE expenditure functions that are offered by the system may have any of several origins. They may be loaded onto the system prior to its distribution by a manufacturer. As such, they may be incompletely defined and then completely defined by the device or user to conform with real time BGC-neutral rate of PDIUE expenditure data prior to selection. They may be created de novo or by modification of pre-existing versions on a user's personal computer, and then loaded onto the system. They may be designed remotely by a healthcare provider, another user, or a manufacturer of the system, then transferred to a user's personal computer via the internet or other wired or wireless network, a CD, or another computer readable storage medium, and then, after optional user modification, loaded onto the system. They may be historical, actual BGC-neutral rate of PDIUE expenditure functions. They may be previously used BGC-neutral rate of PDIUE expenditure functions that were saved. They may be BGC-neutral rate of PDIUE expenditure functions that were previously created on a display screen of the system and, without being used first, saved for future use. In order to simplify the representation of graphs of BGC-neutral rate of PDIUE expenditure functions when displayed for selection by a user, the device may optionally represent them as non-smoothed line graphs with key points highlighted, or it may represent them as a list of key point coordinates, or it may represent them with labels applied to them by a user to indicate a situation in which they are predicted, such as "Chinese food" or "forgot to bolus". Graphs of BGC-neutral rate of PDIUE expenditure functions may be drawn, chosen, modified, and manipulated by analogy to the methods disclosed for drawing, choosing, modifying, and manipulating graphs of expected blood glucose concentration in WO 2006/133348.

The display of predicted BGC-neutral rates of PDIUE expenditure may be in the form of a graph of the predicted BGC-neutral rate of PDIUE expenditure versus time, for example, a line graph, or it may be in the form of a data table, or it may be in the form of a response to a query. A graph of the predicted BGC-neutral rate of PDIUE expenditure versus time may be displayed along with a graph of the evolving actual BGC-neutral rate of PDIUE expenditure versus time and/or a graph of the anticipated rate of PDIUE expenditure from insulin delivery versus time. Predicted BGC-neutral rates of PDIUE expenditure may also be displayed as values at specific time intervals, for example in the form of a table showing predicted BGC-neutral rates of PDIUE expenditure at 30 minute clock time intervals and/or at 15 minute intervals starting with the present time. A predicted BGC-neutral rate of PDIUE expenditure may also be displayed in response to a query about the predicted BGC-neutral rate of PDIUE expenditure at a specific point in time.

Many of the methods described above for the input and display of predicted BGC-neutral rates of PDIUE expenditure may also be utilized for the input and display of predicted BGC-neutral amounts of PDIUE expenditure.

A system of the invention may also accept, as a prediction of a BGC-neutral amount or rate of PDIUE expenditure, a BGC-neutral amount or rate of PDIUE expenditure that has been originally suggested by the system based on an algorithm that a user has established and that has been adopted by a user through user action or inaction. Such a system suggested BGC-neutral amount or rate of PDIUE expenditure may be displayed before and/or after the adoption step and in any of the formats discussed above.

Comparison of Predicted BGC-Neutral d(PDIUE)/dt and with $$\int_{t1}^{t2} [d(PDIUE)/dt]dt$$

Anticipated d(PDIUE)/dt and $$\int_{t1}^{t2} [d(PDIUE)/dt]dt$$

from Insulin Delivery to Predict BGC Behavior

As described above, a BGC-neutral rate of PDIUE expenditure may be predicted by a user by taking into account a recent past BGC-neutral rate of PDIUE expenditure and other personal experience. Separately, a rate of PDIUE expenditure anticipated from insulin delivery may be calculated. A difference between the two is expected to result in a change in BGC. The magnitude of this change in BGC will depend on the magnitude of the difference between the two, the length of the time interval over which the difference persists, and the responsiveness of the patient's BGC to insulin ($R_{BGC/I}$). Equivalently, predicted BGC-neutral amounts of PDIUE expenditure and anticipated amounts of PDIUE expenditure from insulin delivery may be compared to predict BGC.

For example, if on average, BGC-neutral d(PDIUE)/dt exceeds anticipated d(PDIUE)/dt from insulin delivery by 0.5 U/h over a specific one hour period, then a $$\int_{t1}^{t2} [d(PDIUE)/dt]dt$$

deficit of 0.5 U would be expected. If the patient's BGC typically responds to insulin at a rate of 100 mg/dL per unit, then it can be predicted that over this one hour period of interest, the patient's BGC will rise by 50 mg/dL. Conversely, if on average, BGC-neutral d(PDIUE)/dt is less than anticipated d(PDIUE)/dt from insulin delivery by 0.9 U/h over a specific 40 minute period, then a $$\int_{t1}^{t2} [d(PDIUE)/dt]dt$$

excess of 0.6 U results. If the patient's BGC typically responds to insulin at a rate of 75 mg/dL per unit, then it can be predicted that over this 40 minute period of interest, the patient's BGC will decline by 45 mg/dL.

As noted above, a system of the invention may perform a comparison of a predicted BGC-neutral rate of PDIUE expenditure with an anticipated rate of PDIUE expenditure from insulin delivery, or a predicted BGC-neutral amount of PDIUE expenditure with an anticipated amount of PDIUE expenditure from insulin delivery, in order to predict BGC behavior over a time interval or a series of time intervals. The anticipated amount or rate of PDIUE expenditure from insulin delivery used in this comparison may take into account either insulin already infused alone, insulin already infused plus insulin programmed to be infused, or insulin already infused plus insulin programmed to be infused, as tentatively adjusted. A system of the invention may display predicted BGC by any standard method, such as a graph of predicted BGC versus time that starts with a recent or current BGC value and evolves according to the relationship between the predicted BGC-neutral rate of PDIUE expenditure and the anticipated rate of PDIUE expenditure from insulin delivery, or equivalently between the predicted BGC-neutral amount of PDIUE expenditure and the anticipated amount of PDIUE expenditure from insulin delivery. Any of these PDIUE-related quantities may be displayed along with predicted BGC.

Adjusting Insulin Delivery, Consuming Carbohydrate, and/or Taking Other Actions in Response to a BGC Prediction to Achieve a Desired BGC Result Once BGC behavior has been predicted as described above, action may be taken to achieve a desired BGC result. However, whether a predicted BGC increase, decrease, or continuation at the same level will lead to a desired BGC result depends not only on any predicted changes in BGC, but also on the current BGC level. For example, if current BGC is high and BGC is predicted to rise, action should be taken. However, if current BGC is low and BGC is predicted to rise, action may not be desirable. Furthermore, if current BGC is high and BGC is predicted to decline, action may or may not be desirable, depending on the magnitude of the predicted BGC decline. Considering both the degree of hyperglycemia and the magnitude of the predicted BGC decline, it may be desirable to take no action, to take action that tends to increase BGC, or to take action that tends to decrease BGC.

Several possible actions to manage BGC are available to diabetes patients using insulin delivery systems: adjusting insulin delivery, consuming carbohydrate, increasing physical activity, changing an insulin infusion set, and others. Clearly, if the patient suspects that his insulin infusion set has deteriorated, changing it is an obvious choice; he may then need to take additional action to minimize hyperglycemia. Increasing physical activity, while potentially an effective means to decrease BGC, is often inconvenient, may be slower than increasing insulin delivery, and may be difficult to quantify. Physical activity may also be contraindicated if ketoacidosis is suspected. Most commonly, patients employ carbohydrate consumption and insulin delivery adjustment to manage BGC.

Consuming carbohydrate is the most effective remedy when hypoglycemia is already present or anticipated very soon. In this situation, with knowledge of PDIUE data, it is possible to estimate how much carbohydrate should be consumed. Generally, the patient should consume at least as much carbohydrate as would be necessary to offset the greatest total excess of the anticipated amount of PDIUE expenditure from insulin delivery over the predicted BGC-neutral amount of PDIUE expenditure that can be calculated for any time period beginning with the time of the most recent BGC measurement, which presumably has raised concern about hypoglycemia, and ending when the anticipated rate of PDIUE expenditure from insulin delivery returns to zero. To determine how much carbohydrate is necessary to offset this excess, the insulin-to-carbohydrate ratio concept may be used with the total excess of the anticipated amount of PDIUE expenditure from insulin delivery considered as excess insulin to be offset by carbohydrate. The amount of carbohydrate to be consumed is the amount that is normally disposed of by a bolus of the same amount of insulin that the total excess of the anticipated amount of PDIUE expenditure from insulin delivery represents. The ratio, $R_{carb/I}$ which is the amount of carbohydrate disposed of by a unit of insulin, may be a function, including a continuously varying function, of time of day or other factors. If BGC is significantly above target at the start of the time interval used in the calculation of the total excess of the anticipated amount of PDIUE expenditure from insulin delivery, then accordingly less carbohydrate may be consumed, while if BGC is significantly below target at that time, accordingly more carbohydrate should be consumed—the amount of this carbohydrate adjustment being determined by the amount of carbohydrate that would shift BGC under basal conditions by the amount that BGC at the start of the time interval used in the calculation differs from target. The ratio, $R_{BGc/carb}$, which is the responsiveness of the patient's BGC to carbohydrate consumption, may be a function, including a continuously varying function, of time of day or other factors. It is noteworthy that, the calculation of the anticipated amount of PDIUE expenditure from insulin delivery must consider the anticipated amount of PDIUE expenditure from insulin already infused, but the anticipated amount of PDIUE expenditure from insulin programmed but not yet infused may be ignored if the program directing infusion of that insulin is discontinued.

Adjusting insulin delivery may be the best course of action if hypoglycemia is predicted, but not imminently, or if hyperglycemia is predicted, or if hyperglycemia is present and predicted to not resolve in a timely fashion. The options contemplated for adjusting insulin delivery in conjunction with the present invention include all of the modes of insulin delivery offered by currently available insulin delivery systems plus additional modes that are not offered by currently available insulin delivery systems. For example, currently available insulin delivery systems may supply insulin in the form of a standard bolus, in which insulin is delivered essentially all at once, at the time that the standard bolus is programmed. Currently available insulin delivery systems may also supply insulin in the form of an extended bolus, in which insulin is delivered at a essentially uniform rate over an extended period of time, that begins at the time the extended bolus is programmed. Currently available insulin delivery systems may also allow ad hoc, temporarily increased or decreased insulin delivery via their basal programs, and the amount of the increase or decrease (versus the usual basal insulin) may be considered to be, respectively, one or more insulin extended boluses or negative insulin extended boluses delivered over the time intervals available to the basal programming and beginning either when it is programmed or subsequently. Since the time intervals available to a basal program are typically multiples of only 30 minutes, ad hoc, temporarily increased basal program insulin delivery provides a means to accomplish much of what could be accomplished if commercially available insulin delivery systems offered options for pre-programming one or more standard boluses to be delivered substantially after programming and for pre-programming one or more extended boluses to be initiated substantially after programming. A system of the invention is contemplated to also accommodate the explicit pre-programming of one or more standard boluses to be delivered substantially after programming and of one or more extended boluses to be initiated substantially after programming, as well the pre-programming of one or more insulin boluses having a linearly declining rate of insulin delivery over a period of time ranging up to several hours, as well as the programming of insulin delivery according to a fluctuating insulin delivery profile. A fluctuating insulin delivery profile comprises a function of insulin delivery rate over time that may have segments of varying slope and/or an insulin delivery rate that may vary irregularly. The adjustment of insulin delivery with the present invention may be accomplished by programming any or all of the insulin delivery modes noted above, as well as by cancellation or discontinuation of delivery of insulin that has been programmed but not yet infused.

Thus, if non-imminent hypoglycemia, or future hyperglycemia, or existing hyperglycemia that will not resolve in a timely fashion is predicted by consideration of a recent BGC level and a comparison of an anticipated amount of PDIUE expenditure from insulin delivery with a predicted BGC-neutral amount of PDIUE expenditure, then adjusting insulin delivery using one or more of the means described above may be appropriate. It should be noted that the conditions that might appropriately lead to consuming carbohydrate, namely existing or imminent hypoglycemia, and the conditions that might appropriately lead to adjusting insulin delivery, namely non-imminent hypoglycemia, future hyperglycemia, or existing hyperglycemia that will not resolve in a timely fashion, are not mutually exclusive, and situations may arise in which both consumption of carbohydrate and adjustment of insulin delivery are appropriate.

User Adjustment of Programmed Insulin Delivery to Approximate Desired d(PDIUE)/dt and $$\int_{t1}^{t2} [d(PDIUE)/dt]dt$$

from Insulin Delivery

Usually, a desired amount and/or rate of PDIUE expenditure from insulin delivery will not differ much from the predicted BGC-neutral amount and/or rate of PDIUE expenditure, respectively, if BGC is in or near the target range because it is desirable for BGC to remain about the same. If, however, BGC is significantly above the target range, then the desired amount and/or rate of PDIUE expenditure from insulin delivery may be more than the predicted BGC-neutral amount and/or rate of PDIUE expenditure, respectively, in the near term to cause a decrease in BGC. Conversely, if BGC is significantly below the target range, then the desired amount and/or rate of PDIUE expenditure from insulin delivery may be less than the predicted BGC-neutral amount and/or rate of PDIUE expenditure, respectively, in the near term to cause an increase in BGC. In the latter case, when BGC is significantly below target, alternatively to, or in addition to the choice of a lower desired amount and/or rate of PDIUE expenditure from insulin delivery relative to the predicted BGC-neutral amount and/or rate of PDIUE expenditure in the near term, carbohydrate may be consumed to raise BGC quickly. Carbohydrate consumption should increase a user's prediction of a BGC-neutral amount and/or rate of PDIUE expenditure, making it possible to raise predicted BGC with less of a decrease of the amount and/or rate of PDIUE expenditure from insulin delivery than would be the case were it not for the carbohydrate consumption.

As described above, a system of the invention may display a recent BGC value and a predicted evolution of BGC based on a comparison of predicted BGC-neutral amounts and/or rates of PDIUE expenditure with an anticipated amounts and/or rates of PDIUE expenditure from insulin delivery, respectively. This comparison may take into account either insulin already infused alone, insulin already infused plus insulin programmed to be infused, or insulin already infused plus insulin programmed to be infused, as tentatively adjusted. The latter case, in which insulin already infused plus insulin programmed to be infused, as tentatively adjusted, is considered, is intended to offer a user an opportunity to test an insulin delivery scenario for its effect on an anticipated amount and/or rate of PDIUE expenditure from insulin delivery and/or the predicted evolution of BGC. In this test mode, the user may experiment by adjusting combinations of standard, extended, and other types of bolus, as well as basal programming, before committing to implementation. Alternatively, the user may experiment with proposed fluctuating insulin delivery profiles without committing to implementation. Fluctuating insulin delivery profiles may be drawn, chosen, modified, and manipulated by analogy to the methods disclosed for drawing, choosing, modifying, and manipulating graphs of expected blood glucose concentration in WO 2006/133348. The adjustment may be either an addition to, a subtraction from, or a complete replacement of existing insulin delivery programming. When the user finds an insulin delivery scenario that achieves a desired amount and/or rate of PDIUE expenditure from insulin delivery and/or predicted evolution of BGC, the user may implement the insulin delivery scenario, either by manual interaction with his insulin delivery system, or by automatic transfer of the insulin delivery scenario to his insulin delivery system. Test mode may also function as a learning tool or the basis for a game by providing feedback to a user on how closely the anticipated amount and/or rate of PDIUE expenditure from a tentative insulin delivery scenario approximates a desired or otherwise targeted amount and/or rate of PDIUE expenditure from insulin delivery. A comparison by the system of the anticipated and targeted amounts and/or rates of PDIUE expenditure may be displayed to provide feedback to a user, for example visually, for example by graphing them together, or in a derived format, for example by displaying the difference between the anticipated and targeted quantities. A desired or otherwise targeted amount and/or rate of PDIUE expenditure from insulin delivery may originate as an optionally modified prediction of a BGC-neutral amount and/or rate of PDIUE expenditure, or it may be created de novo. If being used purely as a learning tool or as the basis for a game, the targeted amount and/or rate of PDIUE expenditure from insulin delivery in test mode may not be relevant to the current control of BGC. It may even be undesirable at that time. Relevant or not, desirable or not, a targeted amount and/or rate of PDIUE expenditure from insulin delivery may be input by any standard method of data input and by methods analogous to those described above for inputting a prediction of a BGC-neutral amount and/or rate of PDIUE expenditure.

System Adjustment of Programmed Insulin Delivery to Approximate User-Specified d(PDIUE)/dt and $$\int_{t1}^{t2} [d(PDIUE)/dt]dt$$

A system of the invention may accept from a user a command to generate a tentative insulin delivery scenario that may result in an approximation of a desired amount and/or rate of PDIUE expenditure from insulin delivery or a series of desired amounts and/or rates of PDIUE expenditure from insulin delivery or a desired amount and/or rate of PDIUE expenditure from insulin delivery-over-time function; these desired PDIUE-related quantities being an input associated with the command. The desired PDIUE-related input may originate as an optionally modified prediction of a BGC-neutral PDIUE expenditure amount and/or rate or a series of BGC-neutral PDIUE expenditure amounts and/or rates or a BGC-neutral PDIUE expenditure amount and/or rate over time function, or it may be created de novo. The system may accept this command by any standard method of data input, and the desired PDIUE-related input may be defined by methods analogous to those described above for inputting a prediction of a BGC-neutral amount and/or rate of PDIUE expenditure or a time function thereof. By applying known mathematical techniques, those skilled in the arts of engineering and mathematics may devise methods whereby a system of the invention may derive, from a desired PDIUE-related input and an insulin time-action profile function, a tentative insulin delivery scenario that is calculated to provide a PDIUE-related result approximating the desired PDIUE-related input. Such a tentative insulin delivery scenario may be examined in test mode to determine whether or not it achieves the desired PDIUE-related result and/or predicted evolution of BGC. If not, the tentative insulin delivery scenario may be modified. Once satisfied with it, a user may implement the insulin delivery scenario, either by manual interaction with his insulin delivery system, or by causing automatic transfer of the insulin delivery scenario to his insulin delivery system. It is noteworthy that a tentative insulin delivery scenario generated by the system must include insulin already infused, and the anticipated PDIUE expenditure from insulin already infused is an obligatory component of the PDIUE-related result. A tentative insulin delivery scenario generated by a system of the invention may contain any of the insulin delivery elements described in this specification, including a negative extended bolus. Despite the great flexibility afforded by the various insulin delivery modes available, for some possible PDIUE-related inputs, there is no tentative insulin delivery scenario that can provide a close PDIUE-related result. Moreover, the fact that insulin already infused must be included in a tentative insulin delivery scenario further limits the ability of the system to achieve a close result. A system of the invention may perform a comparison of a PDIUE-related input with its closest PDIUE-related result, and if the similarity between them does not meet a minimal requirement, then the system may display an error message indicating the nature of the discrepancy and a warning concerning a risk, for example, "desired insulin action impossible, near term excess unavoidable, beware hypoglycemia."

EXAMPLES

While embodiments of the invention is amenable to various modifications and alternative forms, certain specific embodiments of the invention are shown by way of example as described in detail below. Many additional combinations and permutations of the various aspects of systems of the invention and of these examples and concepts noted elsewhere in this specification are possible, as will be obvious to those familiar with intensive blood glucose management. It should be understood that the intention is not to limit the invention to the particular embodiments or examples described. On the contrary, the intention is to cover all modifications, equivalents, and alternative forms falling within the scope and spirit of the invention as defined by the appended claims.

Examples 1 through 6 are prophetic examples that illustrate situations that commonly arise in the lives of diabetes patients and how a system of the invention may aid blood glucose management in these situations. The prophetic examples are written as narratives in which the patient is Lisa. In these narratives, the past tense is employed to describe events leading up to the point when Lisa interacts with the system of the invention, not to indicate that the events described actually occurred.

The Calculation Tables associated with the examples each illustrate calculations of the invention at one specific calculation data time, as noted. The calculation data time is the time that is associated with time-dependent data used as input into the calculation. The calculation data time is not necessarily the clock time at which a calculation is performed. In many cases, the calculation data time is the most recent time for which BGC data are available because that is the time at which the most current BGC-neutral quantities may be calculated. As a result, BGC and PDIUE-related values presented in a Calculation Table at times up to and including the calculation data time may be considered past data or present data, the latter if the calculation data time is the same as the clock time at which the calculation is performed. BGC and PDIUE-related values presented in a Calculation Table at times after the calculation data time may be considered anticipated or predicted values. Because a calculation data time is sometimes earlier than the clock time at which the calculation is performed, anticipated or predicted BGC and PDIUE-related values presented in a Calculation Table may occur at times that would be considered either past, present or future, as opposed to only future, if judged by the clock time at which the calculation is performed.

Example 1

Lisa uses an insulin pump to deliver aspart insulin subcutaneously and a conventional, point-in-time glucometer to measure her BGC. She has a system of the invention that calculates and displays amounts and rates of PDIUE expenditure from insulin delivery over time intervals beginning up to five hours in the past and ending up to seven hours in the future, based on insulin delivery data describing insulin already infused and insulin programmed to be infused, as obtained by communication with her insulin pump, and insulin already infused plus insulin programmed to be infused, as tentatively adjusted, as input by Lisa into her system in test mode. Lisa knows from experience that beginning about 2.5 hours after an Italian restaurant dinner, for which she has bolused insulin prior to mealtime according to her usual insulin-to-carbohydrate ratio, her BGC inevitably rises unless additional insulin is taken. However, the optimal amount and timing of that additional insulin has been difficult for her to predict accurately ahead of time. This is especially true today because earlier in the day Lisa participated in a Walk to Cure Diabetes which has increased her insulin responsiveness, as physical exercise always does, but to a degree that is difficult for her to estimate. Tonight, upon arriving at the restaurant at 5:50 PM, Lisa's BGC was 140 mg/dL. She gave herself a 4.0 U standard bolus of insulin with her insulin pump, and when her main dish was served at 6:20 PM she gave herself another 5.0 U standard bolus. The 9.0 U total was calculated as 8.5 U to cover an estimated 110 g of carbohydrate (based on her usual ratio of 13 grams of carbohydrate per unit of insulin) in her bread, salad, soup, and manicotti plus 0.5 U as a correction bolus for beginning dinner with a BGC of 140 mg/dL because around dinnertime her BGC typically responds to insulin at a rate of 100 mg/dL per unit and she is targeting a BGC of 90 mg/dL. Lisa had not yet considered the effect that her physical activity might have on her insulin-to-carbohydrate ratio and the efficacy of her 0.5 U correction bolus. At 8:00 PM Lisa checked her BGC and it was 72 mg/dL. Realizing that she may have taken too much insulin, she ate grapes containing 12 grams of sugar, which she assumed will act quickly. At 9:15 PM her BGC was 114 mg/dL, and she initiated an extended bolus of 3.0 U over 2.0 hours. She knew from experience that after this type of meal, she needs at least these 3.0 U and possibly as much as 5.0 U more, depending on her level of physical activity and the amount of cheese in her meal. At 10:30 PM Lisa's BGC was 121 mg/dL. Now, at 11:30 PM it is 156 mg/dL. At this point (11:30 PM), Lisa checks the rate of PDIUE expenditure from insulin delivery feature of her system of the invention. It displays, in bar graph form, average rates of PDIUE expenditure from insulin delivery over one hour intervals starting up to five hours in the past and ending up to seven hours in the future. Lisa sees that over the preceding hour, Lisa has used in the pharmacodynamic sense an average of 0.8 U/h. Her system calculates this 0.8 U/h as follows (refer to Calculation Table 1A). The pharmacodynamic effects of her dinnertime boluses of 4.0 U and 5.0 U were exhausted at the beginning of the last hour (10:30 PM) so they do not contribute. However, her extended bolus does. Her system approximates her 9:15-11:15 PM extended bolus as a 1.5 U standard bolus at 9:45 PM and a 1.5 U standard bolus at 10:45 PM. Referring to an internal look-up table of terminal interval area fractions (% PDIUE remaining as a function of time since bolus, Table A), which is loosely based on literature reported euglycemic glucose clamp studies of aspart and lispro in Type I diabetes, her system calculates that of the first 1.5 U bolus, 1.2 U of PDIUE remained at 10:30 PM and 0.7 U of PDIUE remained at 11:30 PM. Therefore, of this first 1.5 U bolus, 0.5 U of PDIUE was expended from 10:30 PM to 11:30 PM. Additionally, her system calculates that of the second 1.5 U bolus all 1.5 U of PDIUE remained at 10:30 PM and 1.2 U of PDIUE remained at 11:30 PM. Therefore, of this second 1.5 U bolus, 0.3 U of PDIUE was expended from 10:30 PM to 11:30 PM. In total, 0.8 U of PDIUE from insulin delivery was expended from 10:30 PM to 11:30 PM, for an average rate of 0.8 U/h. Because Lisa's BGC rose by 35 mg/dL over this time interval and her BGC typically responds to insulin at a rate of 100 mg/dL per unit, she estimates her PDIUE deficit for the time interval as 0.35 U, and she figures her BGC-neutral PDIUE expenditure as 1.15 U by adding her PDIUE expenditure from insulin delivery to her PDIUE deficit. Finally, she calculates her average BGC-neutral rate of PDIUE expenditure as 1.15 U÷1 h=1.15 U/h. Lisa checks the rate of PDIUE expenditure from insulin delivery feature of her system to see what her anticipated rate of PDIUE expenditure from insulin delivery will be from 11:30 PM to 12:30 AM. Her system calculates that from the extended bolus, the first 1.5 U, approximated as a standard bolus at 9:45 PM, will have 0.3 U of PDIUE remaining at 12:30 AM for a net change of 0.4 U over the hour from 11:30 PM to 12:30 AM. Meanwhile the second 1.5 U, approximated as a standard bolus at 10:45 PM, will have 0.7 U of PDIUE remaining at 12:30 AM for a net change of 0.5 U over the hour from 11:30 PM to 12:30 AM. In total, 0.9 U of PDIUE is anticipated to be expended from 11:30 PM to 12:30 AM for an average rate of 0.9 U/h. Lisa's experience has been that around 5 hours after the start of similar meals (corresponding to about 11:00 PM tonight), her BGC-neutral rate of PDIUE expenditure remains constant for about 2 hours and then declines to zero over the next 3 hours. Based on this, Lisa predicts that to accommodate her BGC-neutral rate of PDIUE expenditure, she will need 1.15 U from 11:30 PM to 12:30 AM, 0.85 U from 12:30 AM to 1:30 AM, 0.5 U from 1:30 AM to 2:30 AM, and 0.2 U from 2:30 AM to 3:30 AM, plus she will need 0.6 U to correct her BGC (156 mg/dL)—a total of 3.3 U. Because her predicted BGC-neutral rate of PDIUE expenditure from 11:30 PM to 12:30 AM exceeds her anticipated rate of PDIUE expenditure from insulin delivery by 0.25 U/h, she predicts that the resulting PDIUE deficit may cause her BGC to continue to rise by 25 mg/dL to 181 mg/dL from 11:30 PM to 12:30 AM. Comparison of her predicted BGC-neutral rates of PDIUE expenditure with her anticipated rates of PDIUE expenditure from insulin delivery over subsequent time intervals (as detailed in Calculation Table 1A) leads her to predict continuing increases in BGC, ultimately to 236 mg/dL by 3:30 AM. Moreover, according to her prediction, her total IOB of 1.9 U at 11:30 PM, which would under basal conditions with a BGC of 156 mg/dL be more than enough to cause hypoglycemia, is not nearly enough under the present circumstances. Lisa considers programming a 1.4 U standard bolus at 11:30 PM to make up the difference between her predicted total PDIUE needed (3.3 U) and her IOB (1.9 U), and she tests this scenario over each 1 hour interval using the rate of PDIUE expenditure from insulin delivery feature of her system in test mode. Her system calculates and displays the new anticipated rates of PDIUE expenditure from insulin delivery calculated as follows (refer also to Calculation Table 1B).

From 11:30 PM to 12:30 AM: 1.3 U total PDIUE (0.4 U from 1.5 U at 9:45 PM, 0.5 U from 1.5 U at 10:45 PM, and 0.4 U from 1.4 U at 11:30 PM). 1.3 U÷1 h=1.3 U/h.

From 12:30 AM to 1:30 AM: 1.2 U total PDIUE (0.3 U from 1.5 U at 9:45 PM, 0.4 U from 1.5 U at 10:45 PM, and 0.5 U from 1.4 U at 11:30 PM). 1.2 U÷1 h=1.2 U/h.

From 1:30 AM to 2:30 AM: 0.6 U total PDIUE (0.0 U from 1.5 U at 9:45 PM, 0.3 U from 1.5 U at 10:45 PM, and 0.3 U from 1.4 U at 11:30 PM). 0.6 U÷1 h=0.6 U/h.

From 2:30 AM to 3:30 AM: 0.2 U total PDIUE (0.0 U from 1.5 U at 9:45 PM, 0.0 U from 1.5 U at 10:45 PM, and 0.2 U from 1.4 U at 11:30 PM). 0.2 U÷1 h=0.2 U/h.

Comparing these anticipated rates of PDIUE expenditure from insulin delivery with her predicted BGC-neutral rates of PDIUE expenditure, Lisa concludes that her tentative 1.4 U standard bolus at 11:30 PM is appropriate because with it, small PDIUE excesses should cause her BGC to arrive at target at around 2:30 AM and remain there, assuming that her basal rate is correct. She programs the delivery of the 1.4 U standard bolus on her insulin pump and goes to sleep after setting her alarm clock for 2:00 AM, planning to check her BGC then just in case her prediction is inaccurate.

TABLE A

| time since bolus (hours:minutes) | % PDIUE expended | % PDIUE remaining |
|---|---|---|
| 0:00 | 0 | 100 |
| 0:15 | 4 | 96 |
| 0:30 | 10 | 90 |
| 0:45 | 18 | 82 |
| 1:00 | 28 | 72 |
| 1:15 | 39 | 61 |
| 1:30 | 48 | 52 |
| 1:45 | 56 | 44 |
| 2:00 | 63 | 37 |
| 2:15 | 70 | 30 |
| 2:30 | 76 | 24 |
| 2:45 | 81 | 19 |
| 3:00 | 86 | 14 |
| 3:15 | 90 | 10 |
| 3:30 | 94 | 6 |
| 3:45 | 97 | 3 |
| 4:00 | 99 | 1 |
| 4:15 | 100 | 0 |

CALCULATION TABLE 1A

EXAMPLE 1, CALCULATION DATA TIME 11:30 PM BEFORE ADJUSTMENT

| time of day | BGC (mg/dL) | PDIUE (units) remaining from 5:50 PM bolus | PDIUE (units) remaining from 6:20 PM bolus | PDIUE (units) remaining from 9:45 PM bolus | PDIUE (units) remaining from 10:45 PM bolus | PDIUE total remaining from all boluses (IOB) | PDIUE expenditure (units) over TIME INTERVAL from insulin delivery |
|---|---|---|---|---|---|---|---|
| 5:50 PM | 140 | 4.0 | | | | | |
| 6:20 PM | | | 5.0 | | | | |
| 8:00 PM | 72 | | | | | | |
| 9:15 PM | 114 | | | | | | |
| 9:45 PM | | | | 1.5 | | | |
| 10:30 PM | 121 | 0.0 | 0.0 | 1.2 | | | |
| 10:45 PM | | | | | 1.5 | | |
| 11:30 PM | 156 | 0.0 | 0.0 | 0.7 | 1.2 | 1.9 | 1.2 − 0.7 + 1.5 − 1.2 = 0.8 (10:30 PM-11:30 PM) |
| 12:30 AM | 181 | | | 0.3 | 0.7 | | 0.7 − 0.3 + 1.2 − 0.7 = 0.9 (11:30 PM-12:30 AM) |
| 1:30 AM | 196 | | | 0.0 | 0.3 | | 0.3 − 0.0 + 0.7 − 0.3 = 0.7 (12:30 AM-1:30 AM) |
| 2:30 AM | 216 | | | 0.0 | 0.0 | | 0.0 − 0.0 + 0.3 − 0.0 = 0.3 (1:30 AM-2:30 AM) |
| 3:30 AM | 236 | | | 0.0 | 0.0 | | 0.0 − 0.0 + 0.0 − 0.0 = 0.0 (2:30 AM-3:30 AM) |

| time of day | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|
| 5:50 PM | | | | |
| 6:20 PM | | | | |
| 8:00 PM | | | | |
| 9:15 PM | | | | |
| 9:45 PM | | | | |
| 10:30 PM | | | | |
| 10:45 PM | | | | |
| 11:30 PM | 0.8 (10:30 PM-11:30 PM) | 0.35 deficit (10:30 PM-11:30 PM) | 1.15 (10:30 PM-11:30 PM) | 1.15 (10:30 PM-11:30 PM) |
| 12:30 AM | 0.9 (11:30 PM-12:30 AM) | 0.25 deficit (11:30 PM-12:30 AM) | 1.15 (11:30 PM-12:30 AM) | 1.15 (11:30 PM-12:30 AM) |
| 1:30 AM | 0.7 (12:30 AM-1:30 AM) | 0.15 deficit (12:30 AM-1:30 AM) | 0.85 (12:30 AM-1:30 AM) | 0.85 (12:30 AM-1:30 AM) |
| 2:30 AM | 0.3 (1:30 AM-2:30 AM) | 0.2 deficit (1:30 AM-2:30 AM) | 0.5 (1:30 AM-2:30 AM) | 0.5 (1:30 AM-2:30 AM) |
| 3:30 AM | 0.0 (2:30 AM-3:30 AM) | 0.2 deficit (2:30 AM-3:30 AM) | 0.2 (2:30 AM-3:30 AM) | 0.2 (2:30 AM-3:30 AM) |

CALCULATION TABLE 1B

EXAMPLE 1, CALCULATION DATA TIME 11:30 PM AFTER ADJUSTMENT

| time of day | BGC (mg/dL) | PDIUE (units) remaining from 9:45 PM bolus | PDIUE (units) remaining from 10:45 PM bolus | PDIUE (units) remaining from 11:30 PM bolus | PDIUE (units) total remaining from all boluses (IOB) | PDIUE expenditure (units) over TIME INTERVAL from insulin delivery |
|---|---|---|---|---|---|---|
| 9:45 PM | | 1.5 | | | | |
| 10:30 PM | 121 | 1.2 | | | | |
| 10:45 PM | | | 1.5 | | | |
| 11:30 PM | 156 | 0.7 | 1.2 | 1.4 | 3.3 | 1.2 − 0.7 + 1.5 − 1.2 = 0.8 (10:30 PM-11:30 PM) |
| 12:30 AM | 141 | 0.3 | 0.7 | 1.0 | | 0.7 − 0.3 + 1.2 − 0.7 + 1.4 − 1.0 = 1.3 (11:30 PM-12:30 AM) |
| 1:30 AM | 106 | 0.0 | 0.3 | 0.5 | | 0.3 − 0.0 + 0.7 − 0.3 + 1.0 − 0.5 = 1.2 (12:30 AM-1:30 AM) |
| 2:30 AM | 96 | 0.0 | 0.0 | 0.2 | | 0.0 − 0.0 + 0.3 − 0.0 + 0.5 − 0.2 = 0.6 (1:30 AM-2:30 AM) |
| 3:30 AM | 96 | 0.0 | 0.0 | 0.0 | | 0.0 − 0.0 + 0.0 − 0.0 + 0.2 − 0.0 = 0.2 (2:30 AM-3:30 AM) |

| time of day | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|
| 9:45 PM | | | | |
| 10:30 PM | | | | |
| 10:45 PM | | | | |
| 11:30 PM | 0.8 (10:30 PM-11:30 PM) | 0.35 deficit (10:30 PM-11:30 PM) | 1.15 (10:30 PM-11:30 PM) | 1.15 (10:30 PM-11:30 PM) |
| 12:30 AM | 1.3 (11:30 PM-12:30 AM) | 0.15 excess (11:30 PM-12:30 AM) | 1.15 (11:30 PM-12:30 AM) | 1.15 (11:30 PM-12:30 AM) |
| 1:30 AM | 1.2 (12:30 AM-1:30 AM) | 0.35 excess (12:30 AM-1:30 AM) | 0.85 (12:30 AM-1:30 AM) | 0.85 (12:30 AM-1:30 AM) |
| 2:30 AM | 0.6 (1:30 AM-2:30 AM) | 0.1 excess (1:30 AM-2:30 AM) | 0.5 (1:30 AM-2:30 AM) | 0.5 (1:30 AM-2:30 AM) |
| 3:30 AM | 0.2 (2:30 AM-3:30 AM) | 0.0 (2:30 AM-3:30 AM) | 0.2 (2:30 AM-3:30 AM) | 0.2 (2:30 AM-3:30 AM) |

Example 2

Lisa uses an insulin pump to deliver lispro insulin subcutaneously and a point-in-time glucometer to measure her BGC. She has a system of the invention, a stand-alone device that she keeps in her pocketbook, that calculates and displays amounts and rates of PDIUE expenditure from insulin delivery over time intervals beginning up to five hours in the past and ending up to seven hours in the future, based on insulin delivery data describing insulin already infused and insulin programmed to be infused, as obtained by communication with her insulin pump; it also imports BGC data by communication with her glucometer, and can, therefore, calculate and display BGC-neutral amounts and rates of PDIUE expenditure. Lisa knows from experience that pizza typically requires a standard bolus of insulin prior to mealtime according to her usual insulin-to-carbohydrate ratio, and in addition, an extended bolus of the same amount of insulin, plus or minus 25%, to be infused over 6 to 8 hours starting at the same time as her pre-meal standard bolus. Although she did bring her scale to the pizza parlor so that she could make a reasonable guess at the number of grams of carbohydrate in her meal, the uncertainty about the optimal amount and length of her extended bolus is considerable. Moreover, it has been 2 days since she last changed her infusion set, and, while they usually last for 3 full days, they sometimes deteriorate sooner. Upon arriving at the pizza parlor at 6:00 PM, she gave herself a 9.0 U standard bolus of insulin, calculated to cover an estimated 117 g of carbohydrate (based on her usual ratio of 13 grams of carbohydrate per unit of insulin); her BGC of 87 mg/dL required no additional action. At that time, she also initiated an extended bolus of 9.0 U to be infused until 12:00 AM. At 9:30 PM Lisa checked her BGC and it was 190 mg/dL, so she gave herself a standard correction bolus of 1.0

U because around dinnertime her BGC typically responds to insulin at a rate of 100 mg/dL per unit and she is targeting a BGC of 90 mg/dL. Due to the considerable uncertainties, Lisa checked her BGC at 10:30 PM; it was 125 mg/dL. Now, at 11:30 PM it is 125 mg/dL again. At this point (11:30 PM), Lisa checks the rate of PDIUE expenditure from insulin delivery feature of her system of the invention. It displays, in bar graph form, average rates of PDIUE expenditure from insulin delivery over one hour intervals starting up to five hours in the past and ending up to seven hours in the future. Lisa sees that over the hour from 9:30 PM to 10:30 PM, her average rate of PDIUE expenditure was 2.3 U/h, and over the hour from 10:30 PM to 11:30 PM, her average rate of PDIUE expenditure was 1.9 U/h. Her system calculates these rates as detailed Calculation Table 2A using the approximation that treats her 9.0 U extended bolus from 6:00 PM to 12:00 AM as a series of six 1.5 U standard boluses at 6:30 PM, 7:30 PM, 8:30 PM, 9:30 PM (added to her 1.0 U correction bolus at this time), 10:30 PM, and 11:30 PM. (Her system refers to Table A for percentages of PDIUE remaining as a function of time since bolus.) Lisa also checks the BGC-neutral rate of PDIUE expenditure feature of her system of the invention. It displays, in bar graph form, average BGC-neutral rates of PDIUE expenditure over one hour intervals. Her system calculates these rates as detailed Calculation Table 2A based on the fact that in the evening her BGC typically responds to insulin at a rate of 100 mg/dL per unit. Lisa sees that over the hour from 9:30 PM to 10:30 PM, her average BGC-neutral rate of PDIUE expenditure was 1.65 U/h, and over the hour from 10:30 PM to 11:30 PM, it was apparently higher, 1.9 U/h. Lisa is rightfully concerned about the apparent trend of her BGC-neutral rate of PDIUE expenditure. Although her BGC has been stable at a level close to target, her BGC-neutral rate of PDIUE expenditure is apparently not trending downward as it normally does 5 hours after a meal, even a pizza meal. She understands that there was considerable uncertainty about the optimal amount and length of her extended bolus, but that a downward trend in her BGC-neutral rate of PDIUE expenditure is to be expected regardless of whether insulin dosing is mismatched to insulin need. Lisa decides to check her BGC again at 12:30 AM, at which time it is 195 mg/dL. Lisa then checks the BGC-neutral rate of PDIUE expenditure feature of her system of the invention, which indicates that over the hour from 11:30 PM to 12:30 AM, her average BGC-neutral rate of PDIUE expenditure was apparently 2.2 U/h (Calculation Table 2B). Lisa understands that this is not a situation in which she has simply underestimated the amount of insulin needed. The continued rising trend in her apparent BGC-neutral rate of PDIUE expenditure is a clear sign of an insulin delivery problem. Lisa chooses to change her insulin infusion set rather than simply bolus more insulin. Note that the word "apparent" is applied here to her BGC-neutral rate of PDIUE expenditure because Lisa's true BGC-neutral rate of PDIUE expenditure is actually declining as expected; however, her insulin delivery problem prevents her true BGC-neutral rate of PDIUE expenditure from being accurately determined from insulin delivery and BGC data the way it normally is.

CALCULATION TABLE 2A

EXAMPLE 2, CALCULATION DATA TIME 11:30 PM

| time of day | BGC (mg/dL) | PDIUE (units) remaining from 6:00 PM bolus | PDIUE (units) remaining from 6:30 PM bolus | PDIUE (units) remaining from 7:30 PM bolus | PDIUE (units) remaining from 8:30 PM bolus | PDIUE (units) remaining from 9:30 PM bolus | PDIUE (units) remaining from 10:30 PM bolus | PDIUE (units) remaining from 11:30 PM bolus |
| --- | --- | --- | --- | --- | --- | --- | --- | --- |
| 6:30 PM | 87 | 9.0 | | | | | | |
| 6:00 PM | | | 1.5 | | | | | |
| 7:30 PM | | | | 1.5 | | | | |
| 8:30 PM | | | | | 1.5 | | | |
| 9:30 PM | 190 | 0.5 | 0.2 | 0.6 | 1.1 | 2.5 | | |
| 10:30 PM | 125 | 0.0 | 0.0 | 0.2 | 0.6 | 1.8 | 1.5 | |
| 11:30 PM | 125 | 0.0 | 0.0 | 0.0 | 0.2 | 0.9 | 1.1 | 1.5 |

| time of day | PDIUE expenditure (units) over TIME INTERVAL from insulin delivery | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
| --- | --- | --- | --- | --- | --- |
| 6:30 PM | | | | | |
| 6:00 PM | | | | | |
| 7:30 PM | | | | | |
| 8:30 PM | | | | | |
| 9:30 PM | | | | | |
| 10:30 PM | 0.5 − 0.0 +<br>0.2 − 0.0 +<br>0.6 − 0.2 +<br>1.1 − 0.6 +<br>2.5 − 1.8 =<br>2.3<br>(9:30 PM-10:30 PM) | 2.3<br>(9:30 PM-10:30 PM) | 0.65 excess<br>(9:30 PM-10:30 PM) | 1.65<br>(9:30 PM-10:30 PM) | 1.65<br>(9:30 PM-10:30 PM) |
| 11:30 PM | 0.2 − 0.0 +<br>0.6 − 0.2 + | 1.9<br>(10:30 PM-11:30 PM) | 0.0<br>(10:30 PM-11:30 PM) | 1.9<br>(10:30 PM-11:30 PM) | 1.9<br>(10:30 PM-11:30 PM) |

CALCULATION TABLE 2A-continued

EXAMPLE 2, CALCULATION DATA TIME 11:30 PM 1.8 − 0.9 +
1.5 − 1.1 =
1.9
(10:30 PM-11:30 PM)

CALCULATION TABLE 2B

EXAMPLE 2, CALCULATION DATA TIME 12:30 AM

| time of day | BGC (mg/dL) | PDIUE (units) remaining from 8:30 PM bolus | PDIUE (units) remaining from 9:30 PM bolus | PDIUE (units) remaining from 10:30 PM bolus | PDIUE (units) remaining from 11:30 PM bolus | PDIUE expenditure (units) over TIME INTERVAL from insulin delivery |
|---|---|---|---|---|---|---|
| 8:30 PM |  | 1.5 |  |  |  |  |
| 9:30 PM | 190 | 1.1 | 2.5 |  |  |  |
| 11:30 PM | 125 | 0.2 | 0.9 | 1.1 | 1.5 | 1.9 (10:30 PM-11:30 PM) |
| 12:30 AM | 195 | 0.0 | 0.4 | 0.6 | 1.1 | 0.2 − 0.0 + 0.9 − 0.4 + 1.1 − 0.6 + 1.5 − 1.1 = 1.6 (11:30 PM-12:30 AM) |

| time of day | average rate of PDIUE expenditure (units/hour) over TIME INTERVAL from insulin delivery | PDIUE (units) excess or deficit over TIME INTERVAL | BGC-neutral PDIUE expenditure (unit) over TIME INTERVAL | average BGC-neutral rate of PDIUE expenditure (units/hour) over TIME INTERVAL |
|---|---|---|---|---|
| 8:30 PM |  |  |  |  |
| 9:30 PM |  |  |  |  |
| 11:30 PM | 1.9 (10:30 PM-11:30 PM) | 0.0 (10:30 PM-11:30 PM) | 1.9 (10:30 PM-11:30 PM) | 1.9 (10:30 PM-11:30 PM) |
| 12:30 AM | 1.6 (11:30 PM-12:30 AM) | 0.6 deficit (11:30 PM-12:30 AM) | 2.2 (11:30 PM-12:30 AM) | 2.2 (11:30 PM-12:30 AM) |

Example 3

Lisa injects her glulisine insulin subcutaneously by syringe and uses a point-in-time glucometer to measure her BGC. She has a system of the invention that calculates and displays amounts and rates of PDIUE expenditure from insulin delivery over time intervals beginning up to five hours in the past and ending up to seven hours in the future, as well as BGC-neutral amounts and rates of PDIUE expenditure, based on insulin delivery data and BGC data that she manually inputs. Her system can also make BGC predictions when Lisa inputs predicted BGC-neutral amounts or rates of PDIUE expenditure. Lisa navigates her system's active calculation table (similar to the Calculation Tables associated with the examples in this specification) by scrolling times (by row) and data types (by column) using up/down and left/right arrows. She can read data from the calculation table, and she can input data using number keys and an enter button. At lunch Lisa ate a hamburger and a salad, for which she injected 4.0 U of glulisine at 12:15 PM to cover 40 g of carbohydrate, based on her usual ratio of 10 grams of carbohydrate per unit of insulin; she had figured her meal to contain 45 g of carbohydrate but chose not to cover 5 g because her BGC was 65 mg/dL, below her target of 100 mg/dL. Lisa checked her BGC at 2:00 PM and found it to be 210 mg/dL. Knowing that she could have a snack if she were to take too much insulin, she gave herself another 4.0 U. Now, at 3:00 PM she is at a movie theater with a friend, the movie is about to start, and her BGC is 150 mg/dL. Lisa is initially not sure whether to eat or not because her BGC is still above target. She also does not want to check her BGC frequently because she wants to focus on the movie. She decides to use her system of the invention to choose a safe and informative time to check her BGC next. Lisa inputs her insulin dosing data into her system's calculation table, and her system automatically calculates and populates the table with amounts and rates of PDIUE expenditure from insulin delivery (Calculation Table 3A). In order to query about specific near future times, Lisa simply enters those times (3:30 PM and 4:00 PM) into the time column of her system's calculation table, and the system populates data for those times as appropriate. The system employs a method for PDIUE calculations that corrects for the impact of the amount of insulin on its duration of effect. According to this method, her system draws percentages of PDIUE remaining as a function of time since bolus from either Table A or Table B, Table A reflecting a shorter duration of insulin effect than Table B. It draws from Table A the percentages of PDIUE remaining of the first 5.0 U of boluses that are less than three hours old, but it draws from Table B the percentages of PDIUE remaining of boluses, less than three hours old, beyond the first 5.0 U. Furthermore, if boluses less than three hours old total more than 5.0 U, then the system uses Table B for any boluses more than three hours old; otherwise, the system uses Table A for boluses more than three hours old. Additionally, if a bolus less than three hours old crosses the 5.0 U threshold, then for the purpose of calculation, the system uses Table A for the portion of it below the threshold and Table B for the rest of it. As shown in Calculation Table 3A, in order to perform the 3:00 PM calculation, the latter rule forces the system to treat the 4.0 U injection at 2:00 PM as a 1.0 U bolus plus a 3.0 U bolus. For the 3:00 PM calculation, the system applies Table A to the 1.0 U unit bolus at 2:00 PM and the 4.0 U bolus at 12:15 PM, while it applies Table B to the 3.0 U unit bolus at 2:00 PM. Note that with this method, a bolus age at a calculation data time is the only age that determines which Table to use for percentages of PDIUE remaining from that bolus at all times in the calculation table corresponding to that calculation data time. Note also that the method employed for the calculation of PDIUE expenditure over a time interval in this example consists of first finding the difference between the percentages of PDIUE remaining at the beginning and end of the time interval and then multiplying that percentage difference by the size of a bolus, whereas in some other examples, the size of a bolus is first multiplied by the percentages of PDIUE remaining at the beginning and end of the time interval to find the amount of PDIUE remaining at the beginning and end of the time interval, and the latter amount is then subtracted from the former amount to find the PDIUE expenditure over time the interval. Lisa next inputs her BGC data into her system's calculation table, and her system automatically calculates and populates the table (Calculation Table 3A) with her BGC-neutral amount and rate of PDIUE expenditure for the time interval from 2:00 PM to 3:00 PM. Her system has already been programmed to make BGC-neutral calculations based on her BGC response to insulin being 100 mg/dL per unit at this time of day. In order to predict her BGC and decide when to next check her BGC and/or eat, Lisa now inputs her predicted average BGC-neutral rates of PDIUE expenditure based on the average BGC-neutral rate of PDIUE expenditure that the system has calculated for the time interval from 2:00 PM to 3:00 PM, 1.3 U/h. Lisa recognizes that it being more than 2 hours after the completion of her lunch, her BGC-neutral rate of PDIUE expenditure should not rise and likely will fall. Her highest priority is to avoid hypoglycemia. Therefore, she uses her system to test what her BGC would do if her BGC-neutral rate of PDIUE expenditure falls at the fastest rate she considers reasonable. In her judgment, that would be a decline to 1.0 U/h over the next half hour (3:00 PM to 3:30 PM) and a further decline to 0.6 U/h over the following half hour (3:30 PM to 4:00 PM). Accordingly, Lisa inputs these values as predictions. For the time intervals 3:00 PM to 3:30 PM and 3:30 PM to 4:00 PM, her system then calculates BGC-neutral amounts of PDIUE expenditure and PDIUE excesses, which it then employs to calculate predicted BGC values at 3:30 PM and 4:00 PM, of 90 mg/dL and 40 mg/dL, respectively. Lisa now understands that in order to be sure to avoid hypoglycemia, she needs to check her BGC again at 3:30 PM and not wait until 4:00 PM. At 3:30 PM she can revise her system's calculation table by updating her then measured BGC, and she can make a new prediction of her BGC-neutral rate of PDIUE expenditure if she so desires, as well as decide if and how much to eat.

TABLE B

| time since bolus (hours:minutes) | % PDIUE expended | % PDIUE remaining |
| --- | --- | --- |
| 0:00 | 0 | 100 |
| 0:15 | 4 | 96 |
| 0:30 | 9 | 91 |
| 0:45 | 15 | 85 |
| 1:00 | 22 | 78 |
| 1:15 | 30 | 70 |
| 1:30 | 39 | 61 |
| 1:45 | 46 | 54 |
| 2:00 | 53 | 47 |
| 2:15 | 59 | 41 |
| 2:30 | 65 | 35 |
| 2:45 | 70 | 30 |
| 3:00 | 75 | 25 |
| 3:15 | 79 | 21 |
| 3:30 | 83 | 17 |
| 3:45 | 87 | 13 |
| 4:00 | 90 | 10 |
| 4:15 | 93 | 7 |
| 4:30 | 95 | 5 |
| 4:45 | 97 | 3 |
| 5:00 | 99 | 1 |
| 5:15 | 100 | 0 |

CALCULATION TABLE 3A

EXAMPLE 3, CALCULATION DATA TIME 3:00 PM

| time of day | BGC (mg/dL) | % PDIUE remaining from 12:15 PM bolus of 4.0 U | % PDIUE remaining from 2:00 PM bolus of 1.0 U | % PDIUE remaining from 2:00 PM bolus of 3.0 U | % PDIUE expenditure over TIME INTERVAL from 12:15 PM bolus of 4.0 U | % PDIUE expenditure over TIME INTERVAL from 2:00 PM bolus of 1.0 U | % PDIUE expenditure over TIME INTERVAL from 2:00 PM bolus of 3.0 U |
| --- | --- | --- | --- | --- | --- | --- | --- |
| 12:15 PM | 65 | 100 | | | | | |
| 2:00 PM | 210 | 44 | 100 | 100 | | | |
| 3:00 PM | 150 | 19 | 72 | 78 | 44 − 19 = 25 (2:00 PM-3:00 PM) | 100 − 72 = 28 (2:00 PM-3:00 PM) | 100 − 78 = 22 (2:00 PM-3:00 PM) |
| 3:30 PM | 90 | 10 | 52 | 61 | 19 − 10 = 9 (3:00 PM-3:30 PM) | 72 − 52 = 20 | 78 − 61 = 17 |

CALCULATION TABLE 3A-continued

EXAMPLE 3, CALCULATION DATA TIME 3:00 PM

| | | | | | | (3:00 PM-3:30 PM) | (3:00 PM-3:30 PM) |
|---|---|---|---|---|---|---|---|
| 4:00 PM | 40 | 3 | 37 | 47 | 10 − 3 = 7 (3:30 PM-4:00 PM) | 52 − 37 = 15 (3:30 PM-4:00 PM) | 61 − 47 = 14 (3:30 PM-4:00 PM) |

| time of day | PDIUE expenditure (units) over TIME INTERVAL from insulin delivery | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|---|
| 12:15 PM | | | | | |
| 2:00 PM | | | | | |
| 3:00 PM | 25% × 4.0 + 28% × 1.0 + 22% × 3.0 = 1.9 (2:00 PM-3:00 PM) | 1.9 (2:00 PM-3:00 PM) | 0.6 excess (2:00 PM-3:00 PM) | 1.3 (2:00 PM-3:00 PM) | 1.3 (2:00 PM-3:00 PM) |
| 3:30 PM | 9% × 4.0 + 20% × 1.0 + 17% × 3.0 = 1.1 (3:00 PM-3:30 PM) | 2.2 (3:00 PM-3:30 PM) | 0.6 excess (3:00 PM-3:30 PM) | 0.5 (3:00 PM-3:30 PM) | 1.0 (3:00 PM-3:30 PM) |
| 4:00 PM | 7% × 4.0 + 15% × 1.0 + 14% × 3.0 = 0.8 (3:30 PM-4:00 PM) | 1.7 (3:30 PM-4:00 PM) | 0.5 excess (3:30 PM-4:00 PM) | 0.3 (3:30 PM-4:00 PM) | 0.6 (3:30 PM-4:00 PM) |

Example 4

Lisa uses an insulin pump to deliver aspart insulin subcutaneously and a continuous glucose monitor to keep track of her BGC. She has a system of the invention, on her laptop computer, that calculates and displays amounts and rates of PDIUE expenditure from insulin delivery over time intervals beginning up to five hours in the past and ending up to seven hours in the future, based on insulin delivery data describing insulin already infused and insulin programmed to be infused, as obtained by communication with her insulin pump, and insulin already infused plus insulin programmed to be infused, as tentatively adjusted, as input by Lisa into her system in test mode. It also imports BGC data by communication with her continuous glucose monitor, and can, therefore, calculate and display BGC-neutral amounts and rates of PDIUE expenditure. The system automatically offsets the BGC data by −15 minutes (considers it 15 minutes older than the time it receives it) to compensate for the continuous glucose monitor's lag time so that BGC values are properly aligned in time with insulin delivery data. Her system makes BGC predictions when Lisa inputs predicted BGC-neutral amounts or rates of PDIUE expenditure. Lisa boarded an airplane at 10:00 AM, knowing that her consequent lack of physical activity would increase her insulin requirements, but she could only guess how much. To compensate, she programmed a temporary increase of her insulin pump's basal rate; starting at 11:30 AM and ending at 3:30 PM (her estimated time of arrival) she would receive an extra 0.3 U/h. At 12:30 PM, with her BGC in her target range, Lisa was served lunch (turkey sandwich, fruit, cheese, and cookies), for which she bolused 10.0 U at that time and began an extended bolus of 6.0 U over 4.0 hours. This was somewhat more insulin than what Lisa would normally take for a meal of this type because she wanted to compensate for her lack of physical activity with extra meal-related insulin in addition to the extra basal insulin she had programmed earlier. Also, she did not want to wait her usual 20 minutes after bolusing before eating, so she bolused extra for that as well, hoping to blunt a rapid rise in BGC. After lunch, her BGC was 161 mg/dL at 2:45 PM, 180 mg/dL at 3:15 PM, and 171 mg/dL at 3:45 PM. At this point (3:45 PM), Lisa retrieves her laptop from the overhead bin and starts up her system of the invention software, which establishes a wireless connection to her insulin pump and continuous glucose monitor. It displays information shown in Calculation Table 4A in graphical form as points connected by lines of different colors plotted with BGC and PDIUE-related quantities on the y-axis and time on the x-axis. Although the clock time is 3:45 PM, Calculation Table 4A shows 3:30 PM calculations because 3:30 PM is the most recent time for which the system has BGC data because the system automatically offsets the continuous glucose monitor's BGC data by −15 minutes to compensate for the continuous glucose monitor's lag time. The system has two "% insulin remaining" look-up tables that it can apply to a bolus to determine its PDIUE remaining, Table A and Table B. The system applies the table of shorter duration, Table A, to any normal bolus and any extended bolus (and segments derived from its division) of up to 8.0 U. For larger boluses it applies Table B. In Calculation Table 4A, PDIUE remaining from Lisa's 10.0 U bolus at 12:30 PM is calculated with Table B. Her extended bolus and her basal rate increase, which is treated as an additional extended bolus, are each approximated as a series of one hour segments with each segment treated as a normal bolus at the midpoint of the segment, which falls on the hour. Table A is used to calculate PDIUE remaining for these. Since the normal boluses representing the extended bolus and the basal rate increase appear at some of the same times, at those times they are summed (1.5 U+0.3 U=1.8 U at 1:00 PM, 2:00 PM, and 3:00 PM) in Calculation Table 4A for conciseness. Lisa's BGC typically responds to insulin at a rate of 100 mg/dL per unit, and she is targeting a BGC of 90 mg/dL. Lisa examines the graph of her BGC-neutral rate of PDIUE expenditure, which shows that from 2:30 PM to 3:00 PM it averaged 4.02 U/h and from 3:00 PM to 3:30 PM it averaged 3.42 U/h. Lisa follows a rule of thumb that she has found useful: When her BGC-neutral rate of PDIUE expenditure begins to decline about three hours after a meal, the total amount of PDIUE expenditure that will result in no net change in BGC when the effects of the meal and all insulin boluses are exhausted is typically about the amount that would be expended in 1.5 hours at her most recent BGC-neutral rate of PDIUE expenditure. Lisa multiplies 3.42 U/h by 1.5 h and finds that her rule of thumb suggests that 5.13 U of PDIUE expenditure after 3:30 PM ought to result in a BGC of about 171 mg/dL when the effects of the meal and all insulin boluses are exhausted around 7:30 PM. As of 3:30 PM, Lisa has 5.51 U of IOB. However, her extended bolus is programmed to continue to run until 4:30 PM, which would add another 1.5 U after 3:30 PM. To understand how her BGC may evolve if her rule of thumb is predictive, into her system's calculation table, Lisa inputs predicted BGC-neutral amounts of PDIUE expenditure that total 5.13 U. She divides the 5.13 U in a manner consistent with the notion that her BGC-neutral rate of PDIUE expenditure should decline with time, allocating 1.33 U to the next half hour, 1.20 U to the following half hour and 2.60 U beyond. Her system of the invention then graphs the predicted course of BGC evolution, which indicates that her BGC will fall through the normal range in about an hour and continue to hypoglycemia thereafter. Lisa wants to take a nap, and she does not want to eat to avoid hypoglycemia, so she employs her system's test mode to see what would happen if she were to simply discontinue her extended bolus now, at 3:45 PM. She tentatively programs that scenario, and as detailed in Calculation Table 4B, the last 15 minutes of the extended bolus are approximated as a normal bolus at 3:38 PM. Now, predicted BGC enters the normal range in about an hour and stays there. Lisa can see how and why her tentatively changed insulin delivery scenario results in this optimum predicted BGC behavior by viewing her system's calculation table and graphs showing insulin delivery, PDIUE expenditure from insulin delivery, and PDIUE excess or deficit, all as functions of time. Satisfied with the outcome of her test, Lisa implements the new insulin delivery scenario, which is transferred from the system to her insulin pump for execution. Lisa takes her nap.

CALCULATION TABLE 4A

EXAMPLE 4, CALCULATION DATA TIME 3:30 PM BEFORE ADJUSTMENT

| time of day | BGC (mg/dL) | PDIUE (units) remaining from 12:00 PM bolus | PDIUE (units) remaining from 12:30 PM bolus | PDIUE (units) remaining from 1:00 PM bolus | PDIUE (units) remaining from 2:00 PM bolus | PDIUE (units) remaining from 3:00 PM bolus | PDIUE (units) remaining from 4:00 PM bolus | PDIUE (units) total remaining from all boluses (IOB) |
|---|---|---|---|---|---|---|---|---|
| 12:00 PM |  | 0.30 |  |  |  |  |  |  |
| 12:30 PM |  |  | 10.00 |  |  |  |  |  |
| 1:00 PM |  |  |  | 1.80 |  |  |  |  |
| 2:00 PM |  |  |  |  | 1.80 |  |  |  |
| 2:30 PM | 161 | 0.07 | 4.70 | 0.94 | 1.62 |  |  | 7.33 |
| 3:00 PM | 180 | 0.04 | 3.50 | 0.67 | 1.30 | 1.80 |  | 7.31 |
| 3:30 PM | 171 | 0.02 | 2.50 | 0.43 | 0.94 | 1.62 |  | 5.51 |
| 4:00 PM | 144 | 0.00 | 1.70 | 0.25 | 0.67 | 1.30 | 1.50 | 5.42 |
| 4:30 PM | 105 | 0.00 | 1.00 | 0.11 | 0.43 | 0.94 | 1.35 | 3.83 |
| 7:30 PM | <<90 | 0.00 | 0.00 | 0.00 | 0.00 | 0.00 | 0.00 | 0.00 |

| time of day | PDIUE expenditure (units) over TIME INTERVAL from insulin delivery | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|---|
| 12:00 PM |  |  |  |  |  |
| 12:30 PM |  |  |  |  |  |
| 1:00 PM |  |  |  |  |  |
| 2:00 PM |  |  |  |  |  |
| 2:30 PM |  |  |  |  |  |
| 3:00 PM | 1.82 (2:30 PM-3:00 PM) | 3.64 (2:30 PM-3:00 PM) | 0.19 deficit (2:30 PM-3:00 PM) | 2.01 (2:30 PM-3:00 PM) | 4.02 (2:30 PM-3:00 PM) |
| 3:30 PM | 1.80 (3:00 PM-3:30 PM) | 3.60 (3:00 PM-3:30 PM) | 0.09 excess (3:00 PM-3:30 PM) | 1.71 (3:00 PM-3:30 PM) | 3.42 (3:00 PM-3:30 PM) |
| 4:00 PM | 1.59 (3:30 PM-4:00 PM) | 3.18 (3:30 PM-4:00 PM) | 0.26 excess (3:30 PM-4:00 PM) | 1.33 (3:30 PM-4:00 PM) |  |
| 4:30 PM | 1.59 (4:00 PM-4:30 PM) | 3.18 (4:00 PM-4:30 PM) | 0.39 excess (4:00 PM-4:30 PM) | 1.20 (4:00 PM-4:30 PM) |  |
| 7:30 PM | 3.83 (4:30 PM-7:30 PM) | 1.28 (4:30 PM-7:30 PM) | 1.23 excess (4:30 PM-7:30 PM) | 2.60 (4:30 PM-7:30 PM) |  |

CALCULATION TABLE 4B

EXAMPLE 4, CALCULATION DATA TIME 3:30 PM AFTER ADJUSTMENT

| time of day | BGC (mg/dL) | PDIUE (units) remaining from 12:00 PM bolus | PDIUE (units) remaining from 12:30 PM bolus | PDIUE (units) remaining from 1:00 PM bolus | PDIUE (units) remaining from 2:00 PM bolus | PDIUE (units) remaining from 3:00 PM bolus | PDIUE (units) remaining from 3:38 PM bolus | (units) total remaining from all boluses (IOB) |
|---|---|---|---|---|---|---|---|---|
| 12.00 PM | | 0.30 | | | | | | |
| 12:30 PM | | | 10.00 | | | | | |
| 1:00 PM | | | | 1.80 | | | | |
| 2:00 PM | | | | | 1.80 | | | |
| 2:30 PM | 161 | 0.07 | 4.70 | 0.94 | 1.62 | | | |
| 3:00 PM | 180 | 0.04 | 3.50 | 0.67 | 1.30 | 1.80 | | |
| 3:30 PM | 171 | 0.02 | 2.50 | 0.43 | 0.94 | 1.62 | | 5.51 |
| 3:38 PM | | | | | | | 0.38 | |
| 4:30 PM | 112 | 0.00 | 1.00 | 0.11 | 0.43 | 0.94 | 0.29 | |
| 7:30 PM | 95 | 0.00 | 0.00 | 0.00 | 0.00 | 0.00 | 0.00 | 0.00 |

| time of day | PDIUE expenditure (units) over TIME INTERVAL from insulin delivery | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|---|
| 12.00 PM | | | | | |
| 12:30 PM | | | | | |
| 1:00 PM | | | | | |
| 2:00 PM | | | | | |
| 2:30 PM | | | | | |
| 3:00 PM | 1.82 (2:30 PM-3:00 PM) | 3.64 (2:30 PM-3:00 PM) | 0.19 deficit (2:30 PM-3:00 PM) | 2.01 (2:30 PM-3:00 PM) | 4.02 (2:30 PM-3:00 PM) |
| 3:30 PM | 1.80 (3:00 PM-3:30 PM) | 3.60 (3:00 PM-3:30 PM) | 0.09 excess (3:00 PM-3:30 PM) | 1.71 (3:00 PM-3:30 PM) | 3.42 (3:00 PM-3:30 PM) |
| 3:38 PM | | | | | |
| 4:30 PM | 3.12 (3:30 PM-4:30 PM) | 3.12 (3:30 PM-4:30 PM) | 0.59 excess (3:30 PM-4:30 PM) | 2.53 (3:30 PM-4:30 PM) | |
| 7:30 PM | 2.77 (4:30 PM-7:30 PM) | 0.92 (4:30 PM-7:30 PM) | 0.17 excess (4:30 PM-7:30 PM) | 2.60 (4:30 PM-7:30 PM) | |

Example 5

Lisa uses an all-in-one device that integrates a user interface for her insulin pump, which delivers aspart insulin subcutaneously, a user interface for her continuous glucose monitor, and her system of the invention. Her system calculates and displays amounts and rates of PDIUE expenditure from insulin delivery over time intervals beginning up to five hours in the past and ending up to seven hours in the future, based on insulin delivery data describing insulin already infused and insulin programmed to be infused, as well as insulin already infused plus insulin programmed to be infused, as tentatively adjusted, as input by Lisa into her system in test mode. It also calculates and displays BGC-neutral amounts and rates of PDIUE expenditure. Her system automatically offsets the BGC data by −30 minutes (considers it 30 minutes older than the time it receives it) to compensate for the continuous glucose monitor's long lag time so that BGC values are properly aligned in time with insulin delivery data. Her system makes BGC predictions when Lisa inputs predicted BGC-neutral amounts or rates of PDIUE expenditure. Shortly after running 6 miles this morning, and feeling slightly hypoglycemic, as confirmed by a fingerstick test showing her BGC to be 62 mg/dL, Lisa ate a chicken pot pie for lunch. She was not sure how much carbohydrate her lunch contained, but knowing that her exercise would increase her body's responsiveness to insulin, at 11:30 AM, just before eating, she bolused 4.0 U, which was less insulin than she normally would bolus for the amount of carbohydrate she roughly estimated, and she decreased her basal rate by 0.4 U/h. The meal made her feel better, and she confirmed that her BGC had risen with a fingerstick test showing her BGC to be 147 mg/dL immediately after eating. At 1:30 PM, Lisa's continuous glucose monitor indicated a BGC of 170 mg/dL, and at 1:45 PM, it indicated a BGC of 143 mg/dL. Now, at 2:00 PM, Lisa's continuous glucose monitor indicates a BGC of 115 mg/dL. Lisa scrolls her system's calculation table to view her BGC-neutral rates of PDIUE expenditure. Although the clock time is 2:00 PM, her system shows 1:30 PM calculations (Calculation Table 5A) because the system automatically offsets the BGC data by −30 minutes to compensate for the continuous glucose monitor's long lag time. The system determines PDIUE remaining from a "% insulin remaining" look-up table, Table A. Lisa's basal rate decrease is treated as a negative extended bolus, which is approximated as a series of one hour segments with each segment treated as a bolus having occurred at the midpoint of the segment, but having a negative value, and therefore subtracting from PDIUE expenditure. Lisa's BGC typically responds to insulin at a rate of 100 mg/dL per unit, and she is targeting a BGC of 90 mg/dL. Lisa's BGC-neutral rates of PDIUE expenditure are unusual. Her average rate from 1:00 PM to 1:15 PM is −0.08 U/h, and from 1:15 PM to 1:30 PM it is −0.20 U/h. This means that even with her basal rate decrease, her basal rate is too high.

Since her BGC was already in the normal range at 1:30 PM and is trending lower, and since she her basal rate may still be too high, Lisa checks her system to see what it predicts her BGC ought to be at present (2:00 PM) based on Lisa's assumption that her BGC-neutral rate of PDIUE expenditure might have continued at an average of −0.20 U/h. To perform this calculation, her system considers the last 30 minutes of her 0.40 U/h basal rate decrease to be a negative 0.20 U bolus at 1:45 PM. This leads to a prediction of her 2:00 PM BGC being borderline hypogycemic at 67 mg/dL. Moreover, her system shows 0.33 U of IOB (figuring in her basal rate decrease) at 2:00 PM, which could be expected to decrease her BGC further even if her already diminished basal rate were not still too high. Based on this information, Lisa performs a fingerstick test that shows her BGC to be 69 mg/dL. She enters this value into her system's calculation table at 2:00 PM and locks it to avoid it being overridden by continuous glucose monitor BGC data. Her system then recalculates, and in a 2:00 PM calculation (Calculation Table 5B), it shows that her average BGC-neutral rate of PDIUE expenditure from 1:30 PM to 2:00 PM was −0.16 U/h. At this point, Lisa decreases her basal rate from 0.4 U/h below normal to 0.6 U/h below normal, and she eats two glucose tablets (8 g of glucose), which based on her usual ratio of 10 grams of carbohydrate per unit of insulin, ought to offset about 0.8 U of insulin mostly in the first hour. Accordingly, Lisa inputs to her system 0.80 U as a PDIUE offset remaining at 2:00 PM and 0.20 U remaining at 3:00 PM, and her system calculates a 0.60 U PDIUE offset expenditure over the hour. Her system then automatically augments her BGC-neutral amount of PDIUE expenditure from the −0.20 U that was predicted for the hour, by the 0.60 U offset, to 0.40 U. Lisa then checks to see what her system predicts her BGC will be at 3:00 PM. Her system considers the new basal rate decrease to be a negative 0.60 U bolus at 2:30 PM, and adding together all the anticipated PDIUE expenditure from boluses and negative boluses, and comparing the sum (0.36 U) to Lisa's predicted BGC-neutral amount of PDIUE expenditure that is adjusted for glucose consumption (0.40 U), it finds a PDIUE deficit from 2:00 PM to 3:00 PM of 0.04 U. This leads to a prediction that her 3:00 PM BGC will be 73 mg/dL (Calculation Table 5B).

CALCULATION TABLE 5A

EXAMPLE 5, CALCULATION DATA TIME 1:30 PM
BEFORE ADJUSTMENT

| time of day | BGC (mg/dL) | PDIUE (units) remaining from 11:30 AM bolus | PDIUE (units) remaining from 12:00 PM bolus | PDIUE (units) remaining from 1:00 PM bolus | PDIUE (units) remaining from 1.45 PM bolus | PDIUE (units) total remaining from all boluses (IOB) | PDIUE expenditure (units) over TIME INTERVAL from insulin delivery |
|---|---|---|---|---|---|---|---|
| 11:30 AM |  | 4.00 |  |  |  |  |  |
| 12:00 PM |  | 3.60 | −0.40 |  |  |  |  |
| 1:00 PM | 170 | 2.08 | −0.29 | −0.40 |  |  |  |
| 1:15 PM | 143 | 1.76 | −0.24 | −0.38 |  |  | 0.25 (1:00 PM-1:15 PM) |
| 1:30 PM | 115 | 1.48 | −0.21 | −0.36 |  |  | 0.23 (1:15 PM-1:30 PM) |
| 1:45 PM |  |  |  |  | −0.20 |  |  |
| 2:00 PM | 67 | 0.96 | −0.15 | −0.29 | −0.19 | 0.33 | 0.38 (1:30 PM-2:00 PM) |

| time of day | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|
| 11:30 AM |  |  |  |  |
| 12:00 PM |  |  |  |  |
| 1:00 PM |  |  |  |  |
| 1:15 PM | 1.00 (1:00 PM-1:15 PM) | 0.27 excess (1:00 PM-1:15 PM) | −0.02 (1:00 PM-1:15 PM) | −0.08 (1:00 PM-1:15 PM) |
| 1:30 PM | 0.92 (1:15 PM-1:30 PM) | 0.28 excess (1:15 PM-1:30 PM) | −0.05 (1:15 PM-1:30 PM) | −0.20 (1:15 PM-1:30 PM) |
| 1:45 PM |  |  |  |  |
| 2:00 PM | 0.76 (1:30 PM-2:00 PM) | 0.48 excess (1:30 PM-2:00 PM) | −0.10 (1:30 PM-2:00 PM) | −0.20 (1:30 PM-2:00 PM) |

CALCULATION TABLE 5B

EXAMPLE 5, CALCULATION DATA TIME 2:00 PM AFTER ADJUSTMENT

| time of day | BGC (mg/dL) | PDIUE (units) remaining from 11:30 AM bolus | PDIUE (units) remaining from 12:00 PM bolus | PDIUE (units) remaining from 1:00 PM bolus | PDIUE (units) remaining from 1.45 PM bolus | PDIUE (units) remaining from 2:30 PM bolus | PDIUE expenditure (units) over TIME INTERVAL from insulin delivery | PDIUE offset (units) remaining from glucose consumption |
|---|---|---|---|---|---|---|---|---|
| 11:30 AM | | 4.00 | | | | | | |
| 12:00 PM | | 3.60 | −0.40 | | | | | |
| 1:00 PM | 170 | 2.08 | −0.29 | −0.40 | | | | |
| 1:15 PM | 143 | 1.76 | −0.24 | −0.38 | | | 0.25 (1:00 PM-1:15 PM) | |
| 1:30 PM | 115 | 1.48 | −0.21 | −0.36 | | | 0.23 (1:15 PM-1:30 PM) | |
| 1:45 PM | | | | | −0.20 | | | |
| 2:00 PM | 69 | 0.96 | −0.15 | −0.29 | −0.19 | | 0.38 (1:30 PM-2:00 PM) | 0.80 |
| 2:30 PM | | | | | | −0.60 | | |
| 3:00 PM | 73 | 0.24 | −0.06 | −0.15 | −0.12 | −0.54 | 0.36 (2:00 PM-3:00 PM) | 0.20 |

| time of day | PDIUE offset expenditure (units) over TIME INTERVAL from glucose consumption | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|
| 11:30 AM | | | | |
| 12:00 PM | | | | |
| 1:00 PM | | | | |
| 1:15 PM | | 0.27 excess (1:00 PM-1:15 PM) | −0.02 (1:00 PM-1:15 PM) | −0.08 (1:00 PM-1:15 PM) |
| 1:30 PM | | 0.28 excess (1:15 PM-1:30 PM) | −0.05 (1:15 PM-1:30 PM) | −0.20 (1:15 PM-1:30 PM) |
| 1:45 PM | | | | |
| 2:00 PM | | 0.46 excess (1:30 PM-2:00 PM) | −0.08 (1:30 PM-2:00 PM) | −0.16 (1:30 PM-2:00 PM) |
| 2:30 PM | | | | |
| 3:00 PM | 0.60 (2:00 PM-3:00 PM) | 0.04 deficit (2:00 PM-3:00 PM) | −0.20 + 0.60 = 0.40 (2:00 PM-3:00 PM) | 0.40 (2:00 PM-3:00 PM) |

Example 6

Lisa uses an all-in-one device that integrates a user interface for her insulin pump, which delivers lispro insulin subcutaneously, a user interface for her point-in-time glucometer, and her system of the invention. Her system calculates and displays amounts and rates of PDIUE expenditure from insulin delivery over time intervals beginning up to five hours in the past and ending up to seven hours in the future, based on insulin delivery data describing insulin already infused and insulin programmed to be infused, as well as insulin already infused plus insulin programmed to be infused, as tentatively adjusted, as input by Lisa into her system in test mode. It also calculates and displays BGC-neutral amounts and rates of PDIUE expenditure. Her system makes BGC predictions when Lisa inputs predicted BGC-neutral amounts or rates of PDIUE expenditure. At 6:30 AM, Lisa ate an apple and cereal with milk. However, she was in a rush and forgot to bolus for her breakfast. Now, at 9:30 AM she checks her BGC only to find that it is 440 mg/dL. Lisa reads the bolus history of her insulin pump and understands her mistake. Lisa believes that her breakfast has had its full effect on her BGC and that bringing her BGC back to normal requires a simple correction bolus. At this time of day, her BGC typically responds to insulin at a rate of 100 mg/dL per unit, and she is targeting a BGC of 90 mg/dL. She figures that she needs (440 mg/dL−90 mg/dL)÷100 mg/dL per unit=3.5 U of insulin, and so she tentatively programs a 3.5 U standard bolus in test mode to see how quickly it will bring her BGC back to normal. Since she believes that her breakfast has already had its full effect, Lisa inputs her predicted average BGC-neutral rate of PDIUE expenditure as 0.00 U/h for each of the next few hours. Her system refers to Table A for percentages of PDIUE remaining as a function of time since bolus and, as detailed in Calculation Table 6A, it calculates anticipated amounts of PDIUE expenditure from insulin delivery and makes BGC predictions over the next few hours. Lisa does not like the fact that her BGC at 12:00 PM is predicted to still be as high as 174 mg/dL. Lisa decides to test the idea of bolusing more than 3.5 U now at the expense of basal insulin. Lisa's basal insulin rate is 1.0 U/h. She decides to shift the next two hours of basal insulin to her standard bolus. Accordingly, she tests a 5.5 U standard bolus coupled with a basal rate of 0.0 U/h until 11:30 AM. The basal rate decrease is treated by her system as a −1.00 U bolus at 10:00 AM and another at 11:00 AM. Once again, her system predicts BGC, as detailed in Calculation Table 6B. Lisa is happier with the predicted result of this test, which has her BGC in the normal range at 113 mg/dL by 12:00 PM. She notes that her BGC is predicted to fall to only 72 mg/dL at 1:00 PM. This does not concern her because she plans to monitor her BGC more closely to be sure to avoid hypoglycemia. Lisa implements the 5.5 U standard bolus and basal rate decrease that she has tested. At 12:00 PM, Lisa checks her BGC and finds it to be 183 mg/dL, which is higher than the 113 mg/dL that was predicted based on her predicted average BGC-neutral rate of PDIUE expenditure of 0.00 U/h. Her system shows that since 9:30 AM, her average BGC-neutral rate of PDIUE expenditure has been 0.28 U/h, so she adjusts her predicted average BGC-neutral rates of PDIUE expenditure to reflect her new expectation that they will decline from 0.28 U/h: 0.20 U/h for the next hour, 0.10 U/h for the subsequent hour, and 0.00 U/h after that. In test mode she inputs a 1.0 U standard bolus. Her system then predicts that her BGC will be 112 mg/dL at 2:00 PM and remain in the normal range, as detailed in Calculation Table 6C. Lisa implements the 1.0 U standard bolus that she has tested.

CALCULATION TABLE 6A

EXAMPLE 6, CALCULATION DATA TIME 9:30 AM BEFORE ADJUSTMENT

| time of day | BGC (mg/dL) | PDIUE (units) remaining from 9:30 AM bolus | PDIUE expenditure (units) over TIME INTERVAL from insulin delivery | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|---|---|---|
| 9:30 AM | 440 | 3.50 | | | | | |
| 10:00 AM | 405 | 3.15 | 0.35 (9:30 AM-10:00 AM) | 0.70 (9:30 AM-10:00 AM) | 0.35 excess (9:30 AM-10:00 AM) | 0.00 (9:30 AM-10:00 AM) | 0.00 (9:30 AM-10:00 AM) |
| 11:00 AM | 272 | 1.82 | 1.33 (10:00 AM-11:00 AM) | 1.33 (10:00 AM-11:00 AM) | 1.33 excess (10:00 AM-11:00 AM) | 0.00 (10:00 AM-11:00 AM) | 0.00 (10:00 AM-11:00 AM) |
| 12:00 PM | 174 | 0.84 | 0.98 (11:00 AM-12:00 PM) | 0.98 (11:00 AM-12:00 PM) | 0.98 excess (11:00 AM-12:00 PM) | 0.00 (11:00 AM-12:00 PM) | 0.00 (11:00 AM-12:00 PM) |
| 1:00 PM | 111 | 0.21 | 0.63 (12:00 PM-1:00 PM) | 0.63 (12:00 PM-1:00 PM) | 0.63 excess (12:00 PM-1:00 PM) | 0.00 (12:00 PM-1:00 PM) | 0.00 (12:00 PM-1:00 PM) |
| 2:00 PM | 90 | 0.00 | 0.21 (1:00 PM-2:00 PM) | 0.21 (1:00 PM-2:00 PM) | 0.21 excess (1:00 PM-2:00 PM) | 0.00 (1:00 PM-2:00 PM) | 0.00 (1:00 PM-2:00 PM) |
| 3:00 PM | 90 | 0.00 | 0.00 (2:00 PM-3:00 PM) | 0.00 (2:00 PM-3:00 PM) | 0.00 excess (2:00 PM-3:00 PM) | 0.00 (2:00 PM-3:00 PM) | 0.00 (2:00 PM-3:00 PM) |

CALCULATION TABLE 6B

EXAMPLE 6, CALCULATION DATA TIME 9:30 AM AFTER ADJUSTMENT

| time of day | BGC (mg/dL) | PDIUE (units) remaining from 9:30 AM bolus | PDIUE (units) remaining from 10:00 AM bolus | PDIUE (units) remaining from 11:00 AM bolus | PDIUE expenditure (units) over TIME INTERVAL from insulin delivery |
|---|---|---|---|---|---|
| 9:30 AM | 440 | 5.50 | | | |
| 10:00 AM | 385 | 4.95 | −1.00 | | 0.55 (9:30 AM-10:00 AM) |
| 11:00 AM | 204 | 2.86 | −0.72 | −1.00 | 1.81 (10:00 AM-11:00 AM) |
| 12:00 PM | 113 | 1.32 | −0.37 | −0.72 | 0.91 (11:00 AM-12:00 PM) |
| 1:00 PM | 72 | 0.33 | −0.14 | −0.37 | 0.41 (12:00 PM-1:00 PM) |
| 2:00 PM | 75 | 0.00 | −0.01 | −0.14 | −0.03 (1:00 PM-2:00 PM) |
| 3:00 PM | 89 | 0.00 | 0.00 | −0.01 | −0.14 (2:00 PM-3:00 PM) |

| time of day | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|
| 9:30 AM | | | | |
| 10:00 AM | 1.10 (9:30 AM-10:00 AM) | 0.55 excess (9:30 AM-10:00 AM) | 0.00 (9:30 AM-10:00 AM) | 0.00 (9:30 AM-10:00 AM) |

CALCULATION TABLE 6B-continued

EXAMPLE 6, CALCULATION DATA TIME 9:30 AM AFTER ADJUSTMENT

| | | | | |
|---|---|---|---|---|
| 11:00 AM | 1.81 | 1.81 excess | 0.00 | 0.00 |
| | (10:00 AM-11:00 AM) | (10:00 AM-11:00 AM) | (10:00 AM-11:00 AM) | (10:00 AM-11:00 AM) |
| 12:00 PM | 0.91 | 0.91 excess | 0.00 | 0.00 |
| | (11:00 AM-12:00 PM) | (11:00 AM-12:00 PM) | (11:00 AM-12:00 PM) | (11:00 AM-12:00 PM) |
| 1:00 PM | 0.41 | 0.41 excess | 0.00 | 0.00 |
| | (12:00 PM-1:00 PM) | (12:00 PM-1:00 PM) | (12:00 PM-1:00 PM) | (12:00 PM-1:00 PM) |
| 2:00 PM | −0.03 | 0.03 deficit | 0.00 | 0.00 |
| | (1:00 PM-2:00 PM) | (1:00 PM-2:00 PM) | (1:00 PM-2:00 PM) | (1:00 PM-2:00 PM) |
| 3:00 PM | −0.14 | 0.14 deficit | 0.00 | 0.00 |
| | (2:00 PM-3:00 PM) | (2:00 PM-3:00 PM) | (2:00 PM-3:00 PM) | (2:00 PM-3:00 PM) |

CALCULATION TABLE 6C

EXAMPLE 6, CALCULATION DATA TIME 12:00 PM

| time of day | BGC (mg/dL) | PDIUE (units) remaining from 9:30 AM bolus | PDIUE (units) remaining from 10:00 AM bolus | PDIUE (units) remaining from 11:00 AM bolus | PDIUE (units) remaining from 12:00 PM bolus | PDIUE expenditure (units) over TIME INTERVAL from insulin delivery |
|---|---|---|---|---|---|---|
| 9:30 AM | 440 | 5.50 | | | | |
| 10:00 AM | | | −1.00 | | | |
| 11:00 AM | | | | −1.00 | | |
| 12:00 PM | 183 | 1.32 | −0.37 | −0.72 | 1.00 | 3.27 |
| | | | | | | (9:30 AM-12:00 PM) |
| 1:00 PM | 134 | 0.33 | −0.14 | −0.37 | 0.72 | 0.69 |
| | | | | | | (12:00 PM-1:00 PM) |
| 2:00 PM | 112 | 0.00 | −0.01 | −0.14 | 0.37 | 0.32 |
| | | | | | | (1:00 PM-2:00 PM) |
| 3:00 PM | 103 | 0.00 | 0.00 | −0.01 | 0.14 | 0.09 |
| | | | | | | (2:00 PM-3:00 PM) |
| 4:00 PM | 91 | 0.00 | 0.00 | 0.00 | 0.01 | 0.12 |
| | | | | | | (3:00 PM-4:00 PM) |

| time of day | average rate of PDIUE expenditure (units/hour) over TIME INTERVAL from insulin delivery | PDIUE (units) excess or deficit over TIME INTERVAL | BGC-neutral PDIUE expenditure (units) over TIME INTERVAL | average BGC-neutral rate of PDIUE expenditure (units/hour) over TIME INTERVAL |
|---|---|---|---|---|
| 9:30 AM | | | | |
| 10:00 AM | | | | |
| 11:00 AM | | | | |
| 12:00 PM | 1.31 | 2.57 excess | 0.70 | 0.28 |
| | (9:30 AM-12:00 PM) | (9:30 AM-12:00 PM) | (9:30 AM-12:00 PM) | (9:30 AM-12:00 PM) |
| 1:00 PM | 0.69 | 0.49 excess | 0.20 | 0.20 |
| | (12:00 PM-1:00 PM) | (12:00 PM-1:00 PM) | (12:00 PM-1:00 PM) | (12:00 PM-1:00 PM) |
| 2:00 PM | 0.32 | 0.22 excess | 0.10 | 0.10 |
| | (1:00 PM-2:00 PM) | (1:00 PM-2:00 PM) | (1:00 PM-2:00 PM) | (1:00 PM-2:00 PM) |
| 3:00 PM | 0.09 | 0.09 excess | 0.00 | 0.00 |
| | (2:00 PM-3:00 PM) | (2:00 PM-3:00 PM) | (2:00 PM-3:00 PM) | (2:00 PM-3:00 PM) |
| 4:00 PM | 0.12 | 0.12 excess | 0.00 | 0.00 |
| | (3:00 PM-4:00 PM) | (3:00 PM-4:00 PM) | (3:00 PM-4:00 PM) | (3:00 PM-4:00 PM) |

Example 7

The system receives insulin delivery data up to five hours old and insulin time-action profile data.

From the insulin delivery data and the insulin time-action profile data, the system calculates a past amount and/or rate of PDIUE expenditure from insulin delivery.

The user calculates a past BGC-neutral amount and/or rate of PDIUE expenditure from BGC data up to five hours old and patient $R_{BGC/I}$ data and the past amount and/or rate of PDIUE expenditure from insulin delivery.

The user predicts a BGC-neutral amount and/or rate of PDIUE expenditure.

From the insulin delivery data and the insulin time-action profile data, the system calculates an anticipated amount and/or rate of PDIUE expenditure from insulin delivery.

The user predicts a BGC based on a comparison of the predicted BGC-neutral amount and/or rate of PDIUE expenditure with the anticipated amount and/or rate of PDIUE expenditure from insulin delivery and the patient $R_{BGC/I}$ data.

The user adjusts insulin delivery and/or takes other action as necessary.

Return to step 1.

Example 8

The system receives insulin delivery data up to five hours old and insulin time-action profile data and BGC data up to five hours old and patient $R_{BGC/I}$ data.

From the insulin delivery data and the insulin time-action profile data, the system calculates a past amount and/or rate of PDIUE expenditure from insulin delivery.

The system calculates a past BGC-neutral amount and/or rate of PDIUE expenditure from the BGC data up to five hours old and the patient $R_{BGC/I}$ data and the past amount and/or rate of PDIUE expenditure from insulin delivery.

The system communicates the past BGC-neutral amount and/or rate of PDIUE expenditure to the user.

The user predicts a BGC-neutral amount and/or rate of PDIUE expenditure.

The system receives the predicted BGC-neutral amount and/or rate of PDIUE expenditure from the user.

From the insulin delivery data and the insulin time-action profile data, the system calculates an anticipated amount and/or rate of PDIUE expenditure from insulin delivery.

The system predicts a BGC based on a comparison of the predicted BGC-neutral amount and/or rate of PDIUE expenditure with the anticipated amount and/or rate of PDIUE expenditure from insulin delivery and the patient $R_{BGC/I}$ data.

The user adjusts insulin delivery and/or takes other action as necessary.

Return to step 1.

Example 9

The system receives insulin delivery data up to five hours old and insulin time-action profile data and BGC data up to five hours old and patient $R_{BGC/I}$ data.

From the insulin delivery data and the insulin time-action profile data, the system calculates a past amount and/or rate of PDIUE expenditure from insulin delivery.

The system calculates a past BGC-neutral amount and/or rate of PDIUE expenditure from the BGC data up to five hours old and the patient $R_{BGC/I}$ data and the past amount and/or rate of PDIUE expenditure from insulin delivery.

The system communicates the past BGC-neutral amount and/or rate of PDIUE expenditure to the user.

If the user prompts the system to do so, then the system executes a user-specified algorithm to suggest a BGC-neutral amount and/or rate of PDIUE expenditure that is based on the past BGC-neutral amount and/or rate of PDIUE expenditure.

If the user adopts a BGC-neutral amount and/or rate of PDIUE expenditure suggested by the system, then the same becomes a predicted BGC-neutral amount and/or rate of PDIUE expenditure.

If the user has not adopted a suggested amount and/or rate of PDIUE expenditure, then the user independently predicts a BGC-neutral amount and/or rate of PDIUE expenditure.

The system receives an independently predicted BGC-neutral amount and/or rate of PDIUE expenditure from the user or incorporates a predicted BGC-neutral amount and/or rate of PDIUE expenditure that was suggested by the system and adopted by the user.

From the insulin delivery data and the insulin time-action profile data, the system calculates an anticipated amount and/or rate of PDIUE expenditure from insulin delivery.

The system predicts a BGC based on a comparison of the predicted BGC-neutral amount and/or rate of PDIUE expenditure with the anticipated amount and/or rate of PDIUE expenditure from insulin delivery and patient $R_{BGC/I}$ data.

The user adjusts insulin delivery and/or takes other action as necessary.

Return to step 1.

Example 10

Note—all of the time functions in this example are continuous time functions.

The system receives a command to generate a tentative insulin delivery scenario that results in an approximation of a desired rate of PDIUE expenditure from insulin delivery over time function.

The system receives insulin delivery data up to five hours old and an insulin time-action profile function.

The system truncates the insulin delivery data to exclude the delivery of insulin not yet infused.

From the truncated insulin delivery data up to five hours old and the insulin time-action profile function, the system calculates a minimal anticipated rate of PDIUE expenditure from insulin delivery over time function.

The system subtracts the minimal anticipated rate of PDIUE expenditure from insulin delivery over time function from the desired rate of PDIUE expenditure from insulin delivery over time function to calculate a target rate of PDIUE expenditure from insulin delivery over time function.

From the target rate of PDIUE expenditure from insulin delivery over time function and the insulin time-action profile function, the system calculates a tentative rate of insulin delivery over time function that provides a tentative rate of PDIUE expenditure from insulin delivery over time function that most closely approximates the target rate of PDIUE expenditure from insulin delivery over time function.

The system subtracts the tentative rate of PDIUE expenditure from insulin delivery over time function from the target rate of PDIUE expenditure from insulin delivery over time function to calculate a rate of PDIUE expenditure from insulin delivery over time error function.

If the rate of PDIUE expenditure from insulin delivery over time error function exceeds a predefined limit, then the system displays an error message.

If the rate of PDIUE expenditure from insulin delivery over time error function does not exceed the predefined limit, then the system displays the tentative rate of PDIUE expenditure from insulin delivery over time function, which along with insulin already infused, defines a tentative insulin delivery scenario.

The user examines the tentative insulin delivery scenario in test mode.

Example 11

Note—all of the time functions in this example are continuous time functions.

As a game feature related to test mode, the system displays an insulin time-action profile function and a randomly chosen target rate of PDIUE expenditure from insulin delivery over time function.

The user creates a tentative insulin delivery scenario from a menu of insulin delivery elements that he believes may result in an approximation of the target rate of PDIUE expenditure from insulin delivery over time function.

From the tentative insulin delivery scenario and the insulin time-action profile function, the system calculates a tentative rate of PDIUE expenditure from insulin delivery over time function.

The system subtracts the tentative rate of PDIUE expenditure from insulin delivery over time function from the target rate of PDIUE expenditure from insulin delivery over time function to calculate a rate of PDIUE expenditure from insulin delivery over time error function.

The system integrates over time the absolute value of the rate of PDIUE expenditure from insulin delivery over time error function to calculate a game score.

The system displays the tentative rate of PDIUE expenditure from insulin delivery over time function and the rate of PDIUE expenditure from insulin delivery over time error function and the game score.

If the game score is below a predefined value, then the user has won the game and the game is over.

If the game score is above the predefined value, then the user may modify the tentative insulin delivery scenario and prompt the system to evaluate it.

From the modified tentative insulin delivery scenario and the insulin time-action profile function, the system calculates a modified tentative rate of PDIUE expenditure from insulin delivery over time function.

The system subtracts the modified tentative rate of PDIUE expenditure from insulin delivery over time function from the target rate of PDIUE expenditure from insulin delivery over time function to calculate a modified rate of PDIUE expenditure from insulin delivery over time error function.

The system integrates over time the absolute value of the modified rate of PDIUE expenditure from insulin delivery over time error function to calculate a modified game score.

The system displays the modified tentative rate of PDIUE expenditure from insulin delivery over time function and the modified rate of PDIUE expenditure from insulin delivery over time error function and the modified game score.

If the modified game score is below the predefined value, then the user has won the game and the game is over.

If the modified game score is above the predefined value, then the user has lost the game and the game is over.

The present invention should not be considered to be limited to the particular examples described above, but rather should be understood to cover all aspects of the invention as fairly set out in the attached claims. Various modifications to, and equivalents and alternative forms of, the specifics described above fall within the scope and spirit of the present invention, as will be readily apparent to those having skill in the art to which the invention is directed. The claims are intended to cover all such modifications, equivalents, and alternative forms.

In the appended claims, reference to an element in the singular is not intended to mean "one and only one" unless explicitly so stated, but rather "one or more". It is not necessary for a device or method to address each and every problem sought to be solved by the present invention for it to be encompassed by the present claims.

I claim:

1. A device for managing blood glucose concentration comprising:
    a means for inputting at least two recent past blood glucose concentration data items, each data item comprising a blood glucose concentration value and a time-of-measurement value;
    a means for inputting insulin delivery data items, each data item comprising an insulin dosage amount and a time-of-delivery value;
    a means for inputting insulin time-action profile data;
    a means for inputting patient $R_{BGC/I}$ data, the responsiveness of the patient's blood glucose concentration to insulin, optionally as a function of time of day;
    a means for inputting BGC-neutral phamacodynamic insulin unit equivalent expenditure data,
    the data selected from the group consisting of:
        BGC-neutral d(PDIUE)/dt data, a BGC-neutral rate of pharmacodynamic insulin unit equivalent expenditure; and
        BGC-neutral $$\int_{t1}^{t2} [d(PDIUE)/dt]dt \text{ data,}$$

a BGC-neutral amount of pharmacodynamic insulin unit equivalent expenditure between times $t_1$ and $t_2$, where $t_1$ precedes $t_2$;
    a microprocessor connected to the input means;
    the microprocessor connected to a digital memory;
    the microprocessor connected to wired or wireless communication means;
    the microprocessor configured to perform calculations based upon
        inputted recent past blood glucose concentration data;
        inputted insulin delivery data;
        inputted insulin time-action profile data;
        inputted patient $R_{BGC/I}$ data;
        at least one of:
            inputted BGC-neutral d(PDIUE)/dt data, a BGC-neutral rate of pharmacodynamic insulin unit equivalent expenditure; and
            inputted BGC-neutral $$\int_{t1}^{t2} [d(PDIUE)/dt]dt \text{ data,}$$

a BGC-neutral amount of pharmacodynamics insulin unit equivalent expenditure between times $t_1$ and $t_2$, where $t_1$ precedes $t_2$;
    the microprocessor configured to calculate blood glucose concentration;
    a display connected to the microprocessor;
        for displaying blood glucose concentration.

2. The device of claim 1 further comprising at least one of:
    a glucose meter connected to the microprocessor;
    an insulin pump connected to the microprocessor.

3. A device for managing blood glucose concentration comprising:
    a means for inputting BGC-neutral phamacodynamic insulin unit equivalent expenditure data,
    the data selected from the group consisting of:
        BGC-neutral d(PDRIE)/dt data, a BGC-neutral rate of pharmacodynamic insulin unit equivalent expenditure; and
        BGC-neutral $$\int_{t1}^{t2} [d(PDIUE)/dt]dt \text{ data,}$$

a BGC-neutral amount of pharmacodynamic insulin unit equivalent expenditure between times $t_1$ and $t_2$, where $t_1$ precedes $t_2$;
    a microprocessor connected to the input means;
    the microprocessor connected to a digital memory;

the microprocessor connected to wired or wireless communication means;
the microprocessor configured to perform calculations based upon
at least one of:
inputted BGC-neutral d(PDIUE)/dt data, a BGC-neutral rate of pharmacodynamic insulin unit equivalent expenditure; and
inputted BGC-neutral $$\int_{t1}^{t2} [d(PDIUE)/dt]dt \text{ data},$$

a BGC-neutral amount of pharmacodynamics insulin unit equivalent expenditure between times $t_1$ and $t_2$, where $t_1$ precedes $t_2$;
the microprocessor configured to calculate an item selected from the
group consisting of:
past BGC-neutral d(PDIUE)/dt, a past BGC-neutral rate of pharmacodynamic insulin unit equivalent expenditure; and
predicted BGC-neutral d(PDIUE)/dt, a predicted BGC-neutral rate of pharmacodynamic insulin unit equivalent expenditure; and
past BGC-neutral $$\int_{t1a}^{t2a} [d(PDIUE)/dt]dt,$$

a past BGC-neutral amount of pharmacodynamic insulin unit equivalent expenditure between times $t_{1a}$ and $t_{2a}$, where $t_{1a}$ precedes $t_{2a}$; and
predicted BGC-neutral $$\int_{t1a}^{t2a} [d(PDIUE)/dt]dt,$$

a predicted BGC-neutral amount of pharmacodynamic insulin unit equivalent expenditure between times $t_{1a}$ and $t_{2a}$, where $t_{1a}$ precedes $t_{2a}$;
a display connected to the microprocessor;
for displaying at least one of;
past BGC-neutral d(PDIUE)/dt; and
predicted BGC-neutral d(PDRIE)/dt; and
past BGC-neutral $$\int_{t1a}^{t2a} [d(PDIUE)/dt]dt;$$

and
predicted BGC-neutral $$\int_{t1a}^{t2a} [d(PDIUE)/dt]dt.$$

4. The device of claim 3 further comprising at least one of:
a glucose meter connected to the microprocessor;
an insulin pump connected to the microprocessor.

5. A device for managing blood glucose concentration comprising:
a means for inputting insulin delivery data items, each data item comprising
an insulin dosage amount and a time-of-delivery value;
a means for inputting insulin time-action profile data;
a means for inputting BGC-neutral phamacodynamic insulin unit equivalent expenditure data, the data selected from the group consisting of:
BGC-neutral d(PDIUE)/dt data, a BGC-neutral rate of pharmacodynamic insulin unit equivalent expenditure; and
BGC-neutral $$\int_{t1}^{t2} [d(PDIUE)/dt]dt \text{ data},$$

a BGC-neutral amount of pharmacodynamic insulin unit equivalent expenditure between times $t_1$ and $t_2$, where $t_1$ precedes $t_2$;
a microprocessor connected to the input means;
the microprocessor connected to a digital memory;
the microprocessor connected to wired or wireless communication means;
the microprocessor configured to perform calculations based upon
inputted insulin delivery data;
inputted insulin time-action profile data;
at least one of:
inputted BGC-neutral d(PDIUE)/dt data, a BGC-neutral rate of pharmacodynamic insulin unit equivalent expenditure; and
inputted BGC-neutral $$\int_{t1}^{t2} [d(PDIUE)/dt]dt \text{ data},$$

a BGC-neutral amount of pharmacodynamics insulin unit equivalent expenditure between times $t_1$ and $t_2$, where $t_1$ precedes $t_2$;
the microprocessor configured to calculate an item selected from the group consisting of:
the difference between inputted BGC-neutral d(PDIUE)/dt values and
d/(PDIUE)/dt values calculated from inputted insulin delivery data items; and
the difference between inputted BGC-neutral $$\int_{t1}^{t2} [d(PDIUE)/dt]dt$$

values and $$\int_{t1}^{t2} [d(PDIUE)/dt]dt$$

values calculated from inputted insulin delivery data items, calculated between times $t_1$ and $t_2$, where $t_1$ precedes $t_2$
a display connected to the microprocessor.

6. The device of claim 5 further comprising an insulin pump connected to the microprocessor.

7. A device for managing blood glucose concentration comprising:
- a means for inputting at least two recent past blood glucose concentration data items, each data item comprising a blood glucose concentration value and a time-of-measurement value;
- a means for inputting insulin delivery data items, each data item comprising an insulin dosage amount and a time-of-delivery value;
- a means for inputting insulin time-action profile data;
- a means for inputting patient $R_{BGC/I}$ data, the responsiveness of the patient's blood glucose concentration to insulin, optionally as a function of time of day;
- a microprocessor connected to the input means;
- the microprocessor connected to a digital memory;
- the microprocessor connected to wired or wireless communication means;
- the microprocessor configured to perform calculations based upon:
  - inputted recent past blood glucose concentration data;
  - inputted insulin delivery data;
  - inputted insulin time-action profile data;
  - inputted patient $R_{BGC/I}$ data;
- the microprocessor configured to calculate an item selected from the group consisting of:
  - BGC-neutral d(PDHJE)/dt, a BGC-neutral rate of pharmacodynamic insulin unit equivalent expenditure; and
  - BGC-neutral
  $$\int_{t1a}^{t2a} [d(PDIUE)/dt]dt,$$
  a BGC-neutral amount of pharmacodynamic insulin unit equivalent expenditure between times $t_{1a}$ and $t_{2a}$, where $t_{1a}$ precedes $t_{2a}$;
- a display connected to the microprocessor;
  - for displaying at least one of:
    - BGC-neutral d(PDIUE)/dt; and
    - BGC-neutral
    $$\int_{t1a}^{t2a} [d(PDIUE)/dt]dt.$$

8. The device of claim 7 further comprising at least one of:
- a glucose meter connected to the microprocessor;
- an insulin pump connected to the microprocessor.

9. A device for managing blood glucose concentration comprising:
- a means for inputting insulin time-action profile data;
- a means for inputting BGC-neutral phamacodynamic insulin unit equivalent expenditure data,
  the data selected from the group consisting of:
  - BGC-neutral d(PDIUE)/dt data, a BGC-neutral rate of pharmacodynamic insulin unit equivalent expenditure; and
  - BGC-neutral
  $$\int_{t1}^{t2} [d(PDIUE)/dt]dt \text{ data},$$
  a BGC-neutral amount of pharmacodynamic insulin unit equivalent expenditure between times $t_1$ and $t_2$, where $t_1$ precedes $t_2$;
- a microprocessor connected to the input means;
- the microprocessor connected to a digital memory;
- the microprocessor configured to perform calculations based upon inputted insulin time-action profile data;
- at least one of:
  - inputted BGC-neutral d(PDIUE)/dt data, a BGC-neutral rate of pharmacodynamic insulin unit equivalent expenditure; and
  - inputted BGC-neutral
  $$\int_{t1}^{t2} [d(PDIUE)/dt]dt \text{ data},$$
  a BOG-neutral amount of pharmacodynamic insulin unit equivalent expenditure between times $t_1$ and $t_2$, where $t_1$ precedes $t_2$;
- the microprocessor configured to calculate an insulin delivery-over-time function;
- a display connected to the microprocessor.

10. The device of claim 9 further configured to output an insulin delivery-over-time function to an insulin pump.

11. The device of claim 9 wherein the microprocessor is connected to wired or wireless communication means.

* * * * *